US012577236B2

(12) United States Patent
Bollu et al.

(10) Patent No.: US 12,577,236 B2
(45) Date of Patent: Mar. 17, 2026

(54) PROCESSES FOR PREPARATION OF TEZACAFTOR

(71) Applicant: LAURUS LABS LIMITED, Hyderabad (IN)

(72) Inventors: Ravindra Babu Bollu, Hyderabad (IN); Venkateswar Rao Challagonda, Hyderabad (IN); Prasanta Dalasingh, Hyderabad (IN); Ananth Reddy Manda, Hyderabad (IN); Srikanth Konda, Hyderabad (IN); Narender Satu, Hyderabad (IN); Uma Maheswer Rao Vasireddi, Hyderabad (IN)

(73) Assignee: LAURUS LABS LIMITED, Hyderabad (IN)

( * ) Notice: Subject to any disclaimer, the term of this patent is extended or adjusted under 35 U.S.C. 154(b) by 827 days.

(21) Appl. No.: 17/780,268

(22) PCT Filed: Feb. 5, 2021

(86) PCT No.: PCT/IB2021/050949
§ 371 (c)(1),
(2) Date: May 26, 2022

(87) PCT Pub. No.: WO2021/156811
PCT Pub. Date: Aug. 12, 2021

(65) Prior Publication Data

US 2023/0057246 A1 Feb. 23, 2023

(30) Foreign Application Priority Data

Feb. 5, 2020 (IN) ............................ 202041005023

(51) Int. Cl.

| | |
|---|---|
| ***C07D 405/12*** | (2006.01) |
| ***C07D 317/28*** | (2006.01) |
| ***C07D 405/06*** | (2006.01) |
| ***C07D 405/14*** | (2006.01) |
| ***C07D 407/12*** | (2006.01) |
| ***C07D 491/052*** | (2006.01) |

(52) U.S. Cl.
CPC ......... *C07D 405/12* (2013.01); *C07D 317/28* (2013.01); *C07D 405/06* (2013.01); *C07D 405/14* (2013.01); *C07D 407/12* (2013.01); *C07D 491/052* (2013.01)

(58) Field of Classification Search
CPC .................................................. C07D 405/12
See application file for complete search history.

(56) References Cited

U.S. PATENT DOCUMENTS

| | | | | |
|---|---|---|---|---|
| 7,645,789 | B2 | 1/2010 | Ruah et al. | |
| 9,035,072 | B2 | 5/2015 | Belmont et al. | |
| 2009/0131492 | A1 | 5/2009 | Ruah et al. | |
| 2011/0257223 | A1* | 10/2011 | Goor | A61K 31/4709 514/304 |
| 2013/0324743 | A1 | 12/2013 | Belmont et al. | |
| 2020/0223832 | A1 | 7/2020 | Emmett et al. | |

FOREIGN PATENT DOCUMENTS

| | | |
|---|---|---|
| CN | 110437125 A | 11/2019 |
| CN | 111763198 | 10/2020 |
| IN | 2018/21027014 | 1/2019 |
| WO | WO 2010/053471 A1 | 5/2010 |

OTHER PUBLICATIONS

CAS Registry No. 1342896-75-6, which entered STN on Nov. 9, 2011 (Year: 2011).*

David L. Hughes, Patent Review of Synthetic Routes and Crystalline Forms of the CFTR-Modulator Drugs Ivacaftor, Lumacaftor, Tezacaftor, and Elexacaftor, Org. Process Res. Dev., 2019, 23, 11, 2302-2322, Sep. 19, 2019 (Sep. 19, 2019), https://pubs.acs.org/doi/10.1021/acs.oprd.9b00326.

* cited by examiner

*Primary Examiner* — Matthew P Coughlin
(74) *Attorney, Agent, or Firm* — Blank Rome LLP

(57) ABSTRACT

The present invention generally relates to processes for preparation of Tezacaftor and pharmaceutical composition comprising the same. The present invention also encompasses novel intermediates of tezacaftor, processes for its preparation and use of said intermediates in the preparation of tezacaftor.

20 Claims, 4 Drawing Sheets

PROCESSES FOR PREPARATION OF TEZACAFTOR

CROSS-REFERENCE TO RELATED APPLICATIONS

This is a national phase application that is based on and claims the benefit of International Application No. PCT/IB2021/050949, filed on Feb. 5, 2021, which is based on and claims the benefit under Indian Provisional Application No. 202041005023, filed on Feb. 5, 2020, entitled "Novel processes for preparation of tezacaftor," the content of each of which are incorporated by reference herein.

FIELD OF THE INVENTION

The present invention generally relates to processes for preparation of Tezacaftor and pharmaceutical composition comprising the same. The present invention also encompasses novel intermediates of tezacaftor, processes for its preparation and use of said intermediates in the preparation of tezacaftor.

BACKGROUND OF THE INVENTION

Cystic fibrosis is a genetic disease caused by mutations in the cystic fibrosis transmembrane conductance regulator (CFTR) gene which results in construction of a defective CFTR protein. The tunnel-shaped CFTR protein is a chloride channel responsible for controlling the transport of anions and water into and out of epithelial cells. The most frequent mutation, found in about 70% of cystic fibrosis patients, results in deletion of phenylalanine at position 508 of the CFTR amino acid sequence, referred to as F508del-CFTR. This defective protein is unable to fold correctly, hindering its ability to exit the endoplasmic reticulum and migrate to the cell surface. In addition to reduced mobility, the defective protein also has impaired channel gating. The reduced number of CFTR proteins at the cell membrane plus defective gating results in decreased anion secretion and an imbalance of ion and fluid flux. In the lungs, a defective CFTR protein in epithelial cells results in the buildup of thick mucus that can cause lung infections and lung damage.

As a treatment for cystic fibrosis, Vertex Pharmaceuticals has developed two types of drugs to modulate the function of the defective CFTR protein. The drugs termed correctors facilitate transport of protein to the cell surface while those termed potentiators help facilitate chloride trafficking at the cell surface by increasing the time the gate of the protein is open. The two types of drugs can work in tandem to improve overall chloride transport, resulting in healthier lung function.

Symdeko is a combination of tezacaftor and Ivacaftor. Tezacaftor is a cystic fibrosis transmembrane conductance regulator (CFTR) corrector while Ivacaftor is a CFTR potentiator. Tezacaftor moves the defective CFTR protein onto the cell surface, while ivacaftor helps to facilitate the opening of the chloride channel on the cell surface to increase chloride transport.

Symdeko is specifically indicated for the treatment of patients with cystic fibrosis (CF) aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence.

Further Tezacaftor was approved along with other medicaments such as Elexacaftor and Ivacaftor under the brand name Trikafta.

Tezacaftor is chemically designated as (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide. The structural Formula of Tezacaftor is represented as follows:

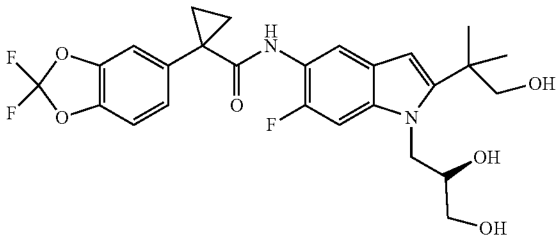

Tezacaftor

Tezacaftor and its process for the preparation was first disclosed in U.S. Pat. No. 7,645,789 ("the '789 patent"). The '789 patent process involves the preparation of Tezacaftor by reaction of aryl bromide with alkyne followed by cyclization to form nitro indole compound. Alkylation of the indole nitrogen with tosylate compound affords mixture of compounds which upon reduction produced alcohol compound.

Hydrogenation of the nitro group produced amine compound and coupling of the resulting amine compound with an acid chloride produced protected Tezacaftor which upon deprotection gives Tezacaftor. The obtained crude Tezacaftor was purified by column chromotography. The process disclosed in the '789 patent is schematically represented as follows:

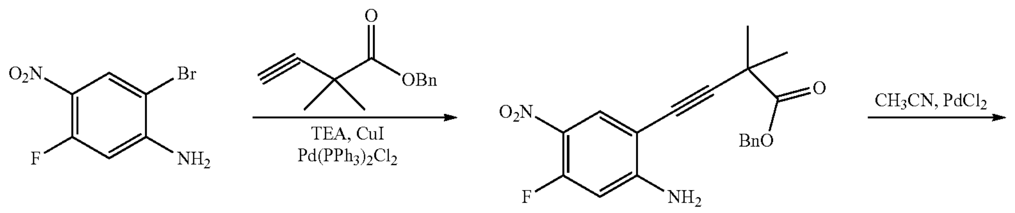

-continued

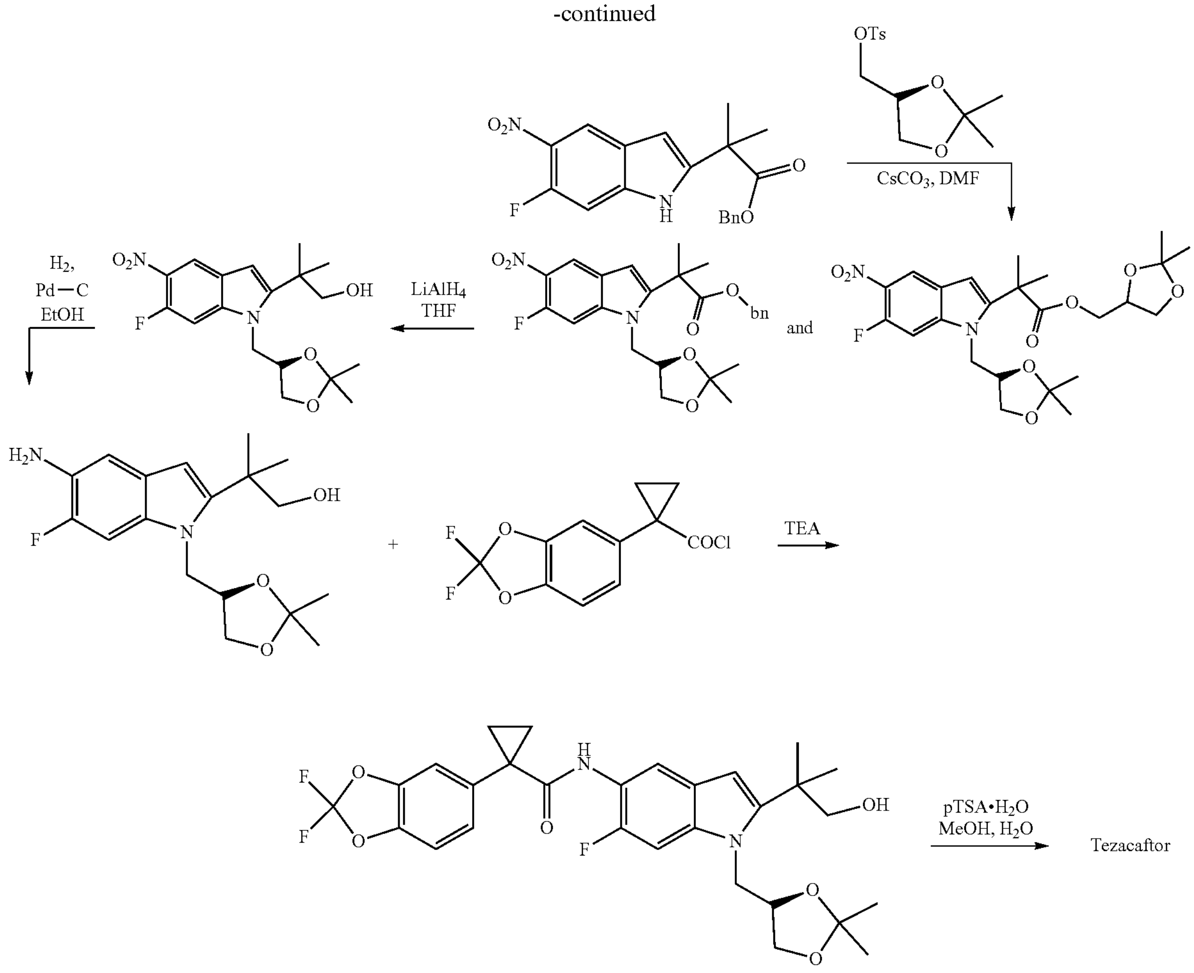

U.S. Pat. No. 9,035,072 ("the '072 patent") disclosed an alternate process for preparation of Tezacaftor by alkylation of amine group of aryl bromide with benzyl glycidyl ether followed by hydrogenation of nitro group to afford amine compound. The resulting amine compound was reacted with alkyne followed by cyclization to afford indole amine compound which upon coupling with an acid chloride provided Benzyl protected Tezacaftor. Hydrogenation of the benzyl protected Tezacaftor provides Tezacaftor which was crystallized from IPA/heptane. The process disclosed in the '072 patent is schematically represented as follows:

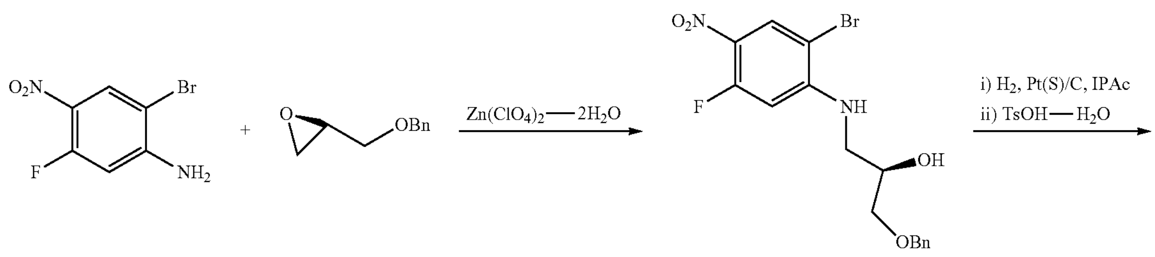

-continued
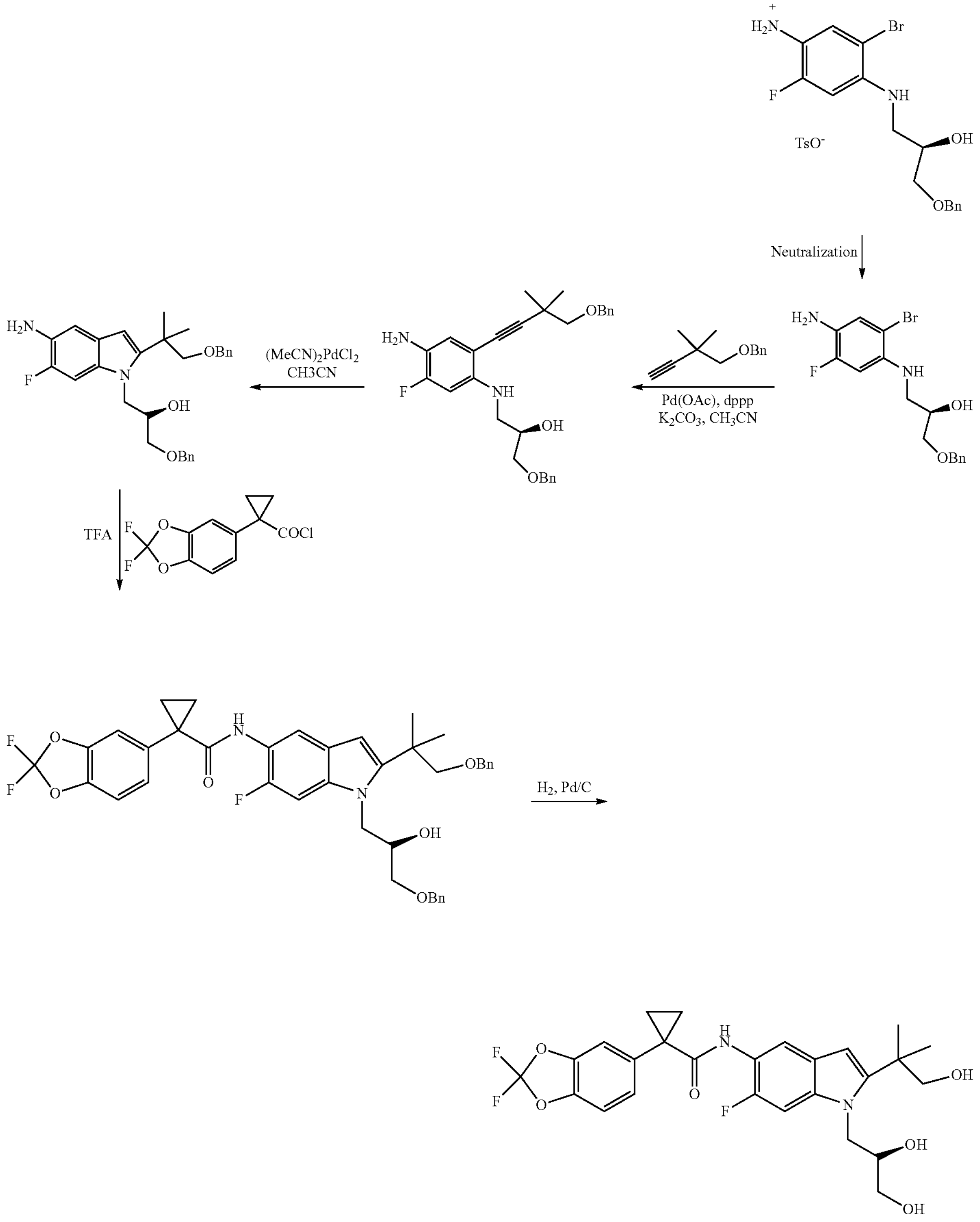
Tezacaftor

Indian patent publication No. 2018/21027014 ("the 014 publication") disclosed a process for the preparation of Tezacaftor by isolating dibenzyl protected Tezacaftor as a solid.

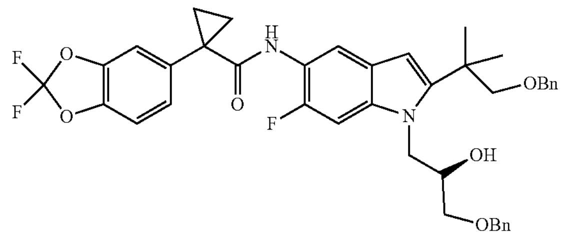

US Publication No. 2020/223832 ("the '832 publication") disclosed an alternate process for preparation of Tezacaftor by coupling of an acid chloride compound with 2-bromo-5-fluoro-4-nitroaniline; alkylation of amine group of resulting aryl bromide with benzyl glycidyl ether, reaction of resulting aryl bromide with alkyne followed by cyclization to obtain protected Tezacaftor which upon deprotection gives Tezacaftor as follows:

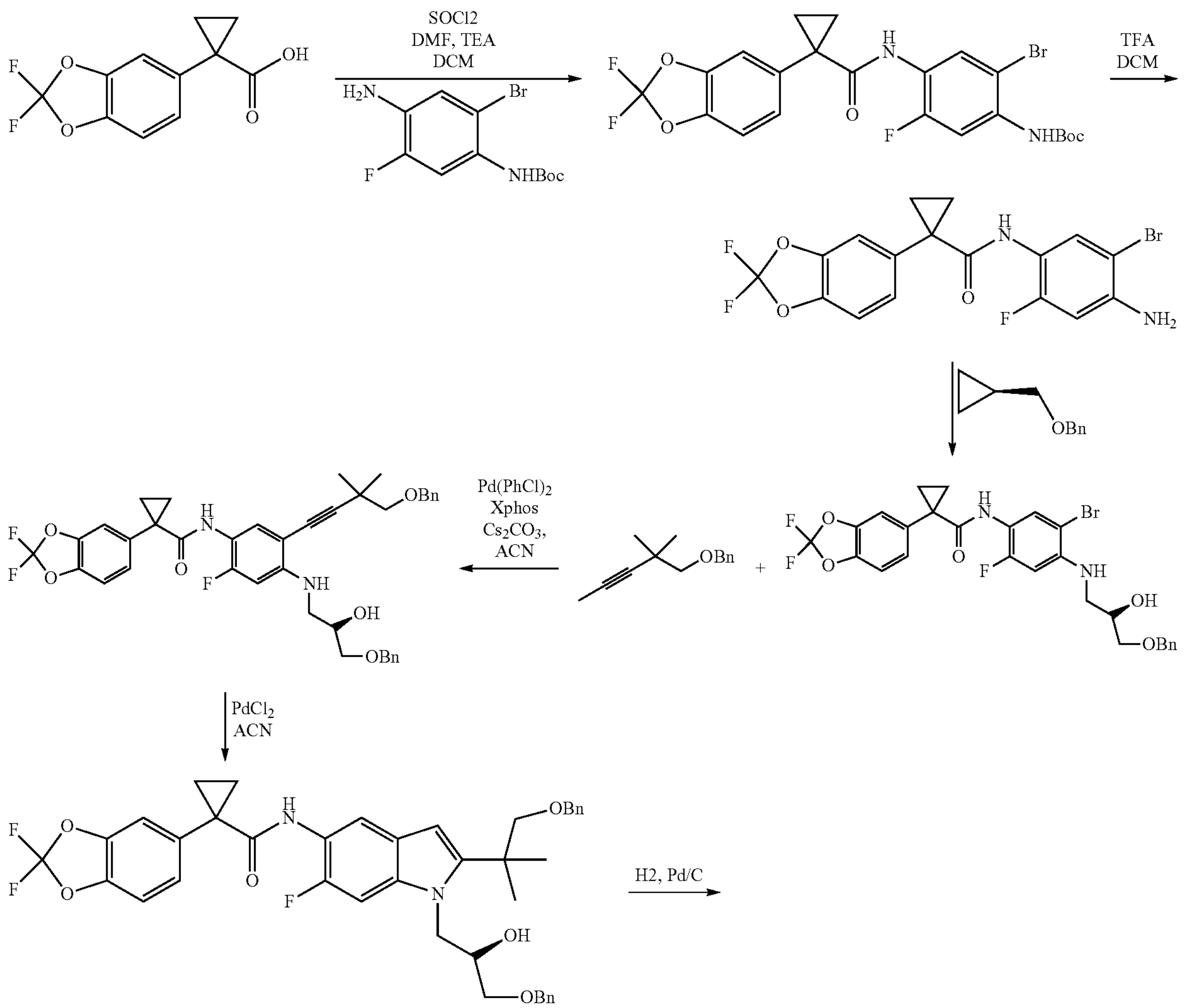

-continued

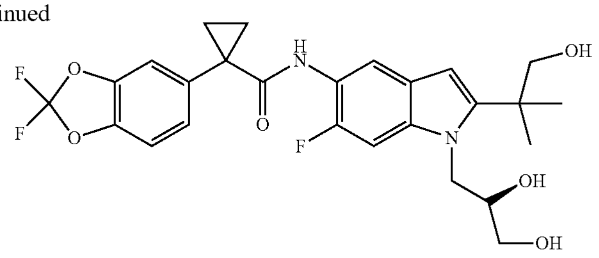

Tezacaftor

Chinese patent publication No. 111763198 ("the '198 publication") disclosed an alternate process for preparation of Tezacaftor by replacement of halo group of 2-nitro-4-fluoro-5-halogenated phenylacetonitrile with amine group, an amidation reaction, a dehydration condensation reaction, a reductive cyclization followed by elimination reaction, ring-opening substitution reaction and finally by a catalytic hydrogenolysis reaction gives Tezacaftor as follows:

Though various processes existed for the preparation of Tezacaftor and its intermediates, there remains a need for an alternative processes for the preparation of Tezacaftor producing high yields and high purity, which is suitable on an industrial scale.

Thus, the present invention provides novel processes for the preparation of Tezacaftor of Formula I by using novel intermediates.

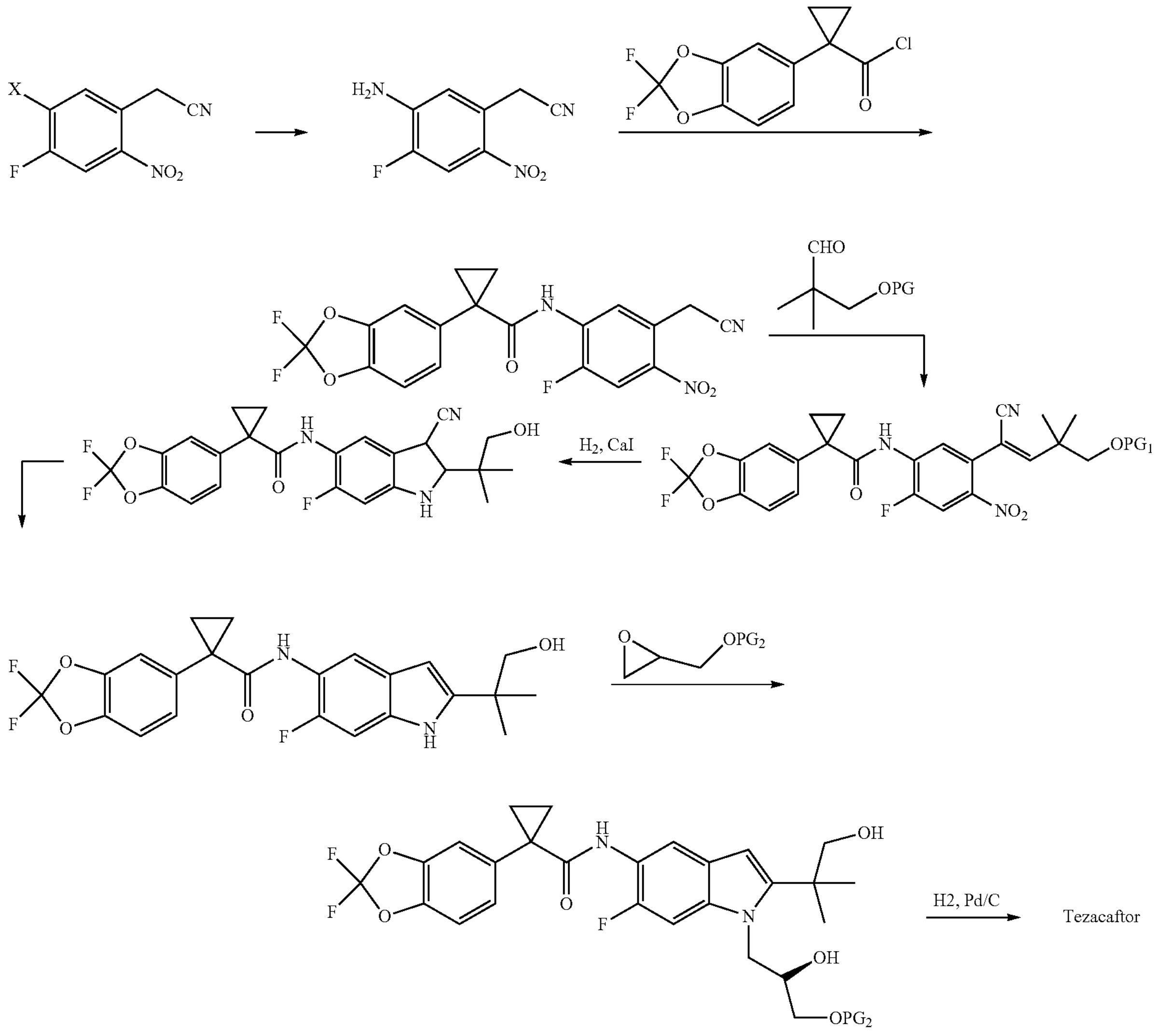

SUMMARY OF THE INVENTION

Accordingly, the present invention provides processes for preparation of Tezacaftor of Formula I.

In accordance with one embodiment, the present invention provides a process for preparation of Tezacaftor of Formula I;

Formula I

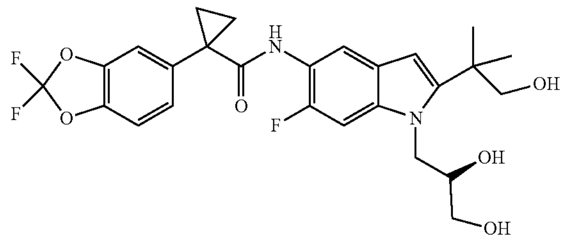

comprising:

a) reacting a compound of Formula II with an alkyne of Formula III to obtain a compound of Formula IV Formula II

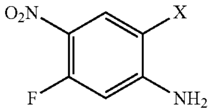

Formula III

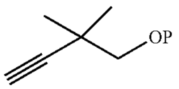

wherein "X" represents a suitable leaving group and "P" represents hydrogen or a suitable hydroxyl protecting group;

Formula IV

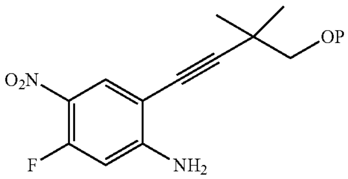

b) treating the compound of Formula IV with a compound of Formula V to obtain a compound of formula VI, Formula V

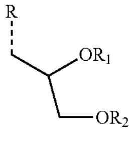

-continued

Formula VI

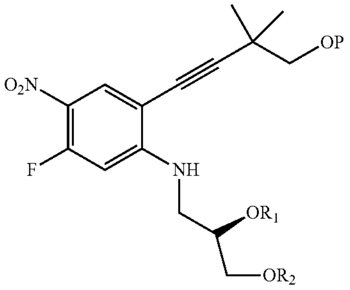

wherein "P" represents hydrogen or a suitable hydroxyl protecting group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group;

c) cyclizing the compound of Formula VI to obtain a compound of Formula VII followed by reduction with a suitable reducing agent to obtain an amine compound of Formula VIII or a salt thereof, or, reducing the compound of Formula VI with a suitable reducing agent to obtain a compound of Formula VII' followed by cyclization to obtain an amine compound of Formula VIII or a salt thereof, Formula VII

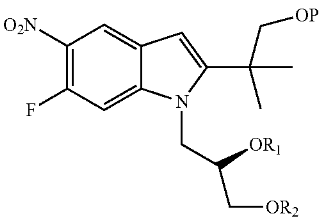

Formula VII'

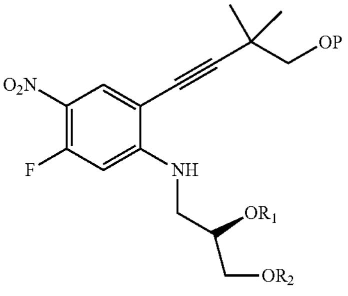

Formula VIII

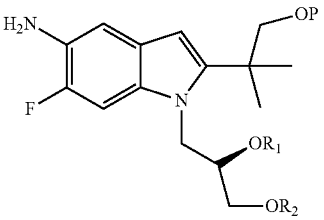

wherein "P" "R1" and "R2" are defined as above;

d) coupling the amine compound of formula VIII or a salt thereof with an acid compound of Formula IX or its reactive derivative thereof to obtain a compound of Formula X;

Formula IX

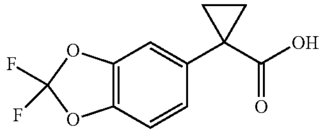

Formula X

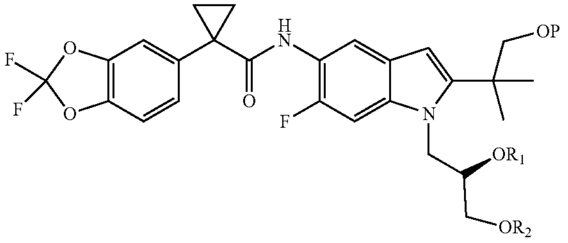

wherein "P" "R1" and "R2" are defined as above; and e) optionally deprotecting the compound of Formula X with a suitable deprotecting agent to obtain Tezacaftor of Formula I.

In accordance with another embodiment, the present invention provides a process for preparation of a compound of Formula IV by reacting a compound of Formula II with an alkyne of Formula III to obtain a compound of Formula IV, wherein "X" represents a suitable leaving group and "P" represents hydrogen or a suitable hydroxyl protecting group.

In accordance with another embodiment, the present invention provides a process for preparation of Tezacaftor of Formula I, comprising:

a) reacting a compound of Formula II with an alkyne of Formula III to obtain a compound of Formula IV, wherein "X" represents a suitable leaving group and "P" represents hydrogen or a suitable hydroxyl protecting group; and b) converting the compound of Formula IV into Tezacaftor of Formula I.

In accordance with another embodiment, the present invention provides a process for preparation of a compound of Formula VI, comprising:

a) reacting a compound of Formula II with an alkyne of Formula III to obtain a compound of Formula IV, wherein "X" represents a suitable leaving group and "P" represents hydrogen or a suitable hydroxyl protecting group; and b) treating the compound of Formula IV with a compound of Formula V to obtain a compound of formula VI, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

In accordance with another embodiment, the present invention provides a process for preparation of a compound of Formula VI, comprising:

a) treating a compound of formula II with a compound of Formula V to obtain a compound of Formula XIII, Formula XIII

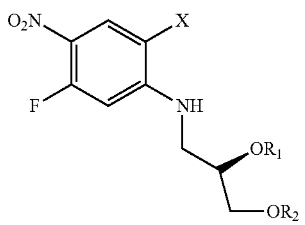

wherein "X" represents a suitable leaving group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group; and b) reacting the compound of Formula XIII with an alkyne of Formula III to obtain a compound of Formula VI, wherein "P" represents hydrogen or a suitable hydroxyl protecting group and "R1" and "R2" are defined as above.

In accordance with another embodiment, the present invention provides a process for purification of a compound of Formula VI, comprising:

a) treating a compound of Formula VI with a suitable solvent, and b) isolating the pure compound of Formula VI.

In accordance with another embodiment, the present invention provides a process for purification of a compound of Formula VI having more than 0.1% of each of Impurity A, Impurity B, Impurity C or Impurity D, comprising:

a) treating a compound of Formula VI with a suitable solvent, and b) isolating the pure compound of Formula VI.

In accordance with another embodiment, the present invention provides a process for preparation of Tezacaftor of Formula I, comprising:

a) preparing the compound of Formula VI, obtained by the processes as described above embodiments, wherein "R", "R1", "R2" and "P" are defined as above; and b) converting the compound of Formula VI into Tezacaftor of Formula I.

In accordance with another embodiment, the present invention provides a process for preparation of an indole compound of Formula VII, comprising: cyclizing a compound of Formula VI to obtain an indole compound of Formula VII, wherein "P" "R1" and "R2" are defined as above.

In accordance with another embodiment, the present invention provides a process for preparation of an indole compound of Formula VII, comprising:

a) reacting a compound of Formula II with an alkyne of Formula III to obtain a compound of Formula IV, wherein "X" represents a suitable leaving group and "P" represents hydrogen or a suitable hydroxyl protecting group;

b) treating the compound of Formula IV with a compound of Formula V to obtain a compound of formula VI, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above; and c) cyclizing the compound of Formula VI to obtain an indole compound of Formula VII, wherein "P" "R1" and "R2" are defined as above.

In accordance with another embodiment, the present invention provides a process for preparation of an indole compound of Formula VII, comprising:

a) treating a compound of formula II with a compound of Formula V to obtain a compound of Formula XIII, wherein "X" represents a suitable leaving group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group; and b) reacting the compound of Formula XIII with an alkyne of Formula III to obtain a compound of Formula VI, wherein "P" represents hydrogen or a suitable hydroxyl protecting group and "R1" and "R2" are defined as above, and c) cyclizing the compound of Formula VI to obtain an indole compound of Formula VII, wherein "P" "R1" and "R2" are defined as above.

In accordance with another embodiment, the present invention provides a process for preparation of an indole compound of Formula VII, comprising:

a) cyclizing a compound of Formula IV to obtain a compound of Formula XII,

Formula XII

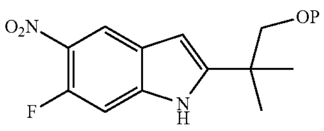

wherein "P" represents hydrogen or a suitable hydroxyl protecting group; and b) treating the compound of Formula XII with a compound of Formula V to obtain an indole compound of formula VII, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

In accordance with another embodiment, the present invention provides a process for preparation of Tezacaftor of Formula I, comprising:

a) preparing an indole compound of formula VII, obtained by the processes as described above embodiments, wherein "R", "R1", "R2" and "P" are defined as above; and b) converting the compound of Formula VII into Tezacaftor of Formula I.

In accordance with another embodiment, the present invention provides a process for preparation of a compound of Formula VII' or a salt thereof, comprising: reducing the compound of Formula VI with a suitable reducing agent to obtain a compound of Formula VII' or a salt thereof, wherein "P" "R1" and "R2" are defined as above.

In accordance with another embodiment, the present invention provides a process for preparation of a compound of Formula VII' or a salt thereof, comprising:

a) reacting a compound of Formula II with an alkyne of Formula III to obtain a compound of Formula IV, wherein "X" represents a suitable leaving group and "P" represents hydrogen or a suitable hydroxyl protecting group;

b) treating the compound of Formula IV with a compound of Formula V to obtain a compound of formula VI, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above; and c) reducing the compound of Formula VI with a suitable reducing agent to obtain a compound of Formula VII' or a salt thereof, wherein "P" "R1" and "R2" are defined as above.

In accordance with another embodiment, the present invention provides a process for preparation of a compound of Formula VII', comprising:

a) treating a compound of formula II with a compound of Formula V to obtain a compound of Formula XIII, wherein "X" represents a suitable leaving group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group;

b) reacting the compound of Formula XIII with an alkyne of Formula III to obtain a compound of Formula VI, wherein "P" represents hydrogen or a suitable hydroxyl protecting group and "R1" and "R2" are defined as above, and c) reducing the compound of Formula VI with a suitable reducing agent to obtain a compound of Formula VII' or a salt thereof, wherein "P" "R1" and "R2" are defined as above.

In accordance with another embodiment, the present invention provides a process for preparation of a compound of Formula VII' or a salt thereof, comprising:

a) reacting a compound of Formula II' with an alkyne of Formula III to obtain a compound of Formula IV', Formula II'

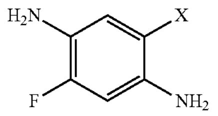

Formula IV'

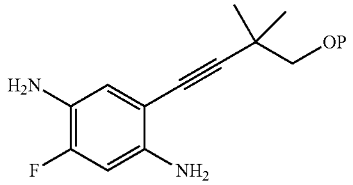

wherein "X" represents a suitable leaving group and "P" represents hydrogen or a suitable hydroxyl protecting group; and b) treating the compound of Formula IV' with a compound of Formula V to obtain a compound of formula VII' or a salt thereof, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

In accordance with another embodiment, the present invention provides a process for preparation of a compound of Formula VII' or a salt thereof, comprising:

a) reacting a compound of Formula II' with a compound of Formula V to obtain a compound of Formula XIII', Formula XIII'

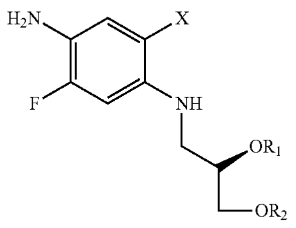

wherein "X" represents a suitable leaving group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group; and b) treating the compound of formula XIII' with an alkyne of Formula III to obtain a compound of formula VII' or a salt thereof, wherein "P" represents hydrogen or a suitable hydroxyl protecting group and "R1" and "R2" are defined as above.

In accordance with another embodiment, the present invention provides a process for preparation of Tezacaftor of Formula I, comprising:

a) preparing the compound of Formula VII' or a salt thereof, obtained by the processes as described above embodiments, wherein "R", "R1", "R2" and "P" are defined as above; and b) converting the compound of Formula VII' into Tezacaftor of Formula I.

In accordance with another embodiment, the present invention provides a process for preparation of a compound of Formula VIII or a salt thereof, comprising: reducing an indole compound of Formula VII with a suitable reducing agent, wherein "P" "R1" and "R2" are defined as above.

In accordance with another embodiment, the present invention provides a process for preparation of a compound of Formula VIII or a salt thereof, comprising: cyclizing a compound of Formula VII', wherein "P" "R1" and "R2" are defined as above.

In accordance with another embodiment, the present invention provides a process for preparation of a compound of Formula VIII or a salt thereof, comprising:

a) reacting a compound of Formula II with an alkyne of Formula III to obtain a compound of Formula IV, wherein "X" represents a suitable leaving group and "P" represents hydrogen or a suitable hydroxyl protecting group;

b) treating the compound of Formula IV with a compound of Formula V to obtain a compound of formula VI, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above; and c) cyclizing the compound of Formula VI to obtain an indole compound of Formula VII followed by reduction with a suitable reducing agent to obtain an amine compound of Formula VIII or a salt thereof, wherein "P" "R1" and "R2" are defined as above.

In accordance with another embodiment, the present invention provides a process for preparation of a compound of Formula VIII or a salt thereof, comprising:

a) reacting a compound of Formula II with an alkyne of Formula III to obtain a compound of Formula IV, wherein "X" represents a suitable leaving group and "P" represents hydrogen or a suitable hydroxyl protecting group;

b) treating the compound of Formula IV with a compound of Formula V to obtain a compound of formula VI, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above; and c) reducing the compound of Formula VI with a suitable reducing agent to obtain a compound of Formula VII' followed by cyclization to obtain an amine compound of Formula VIII or a salt thereof, wherein "P" "R1" and "R2" are defined as above.

In accordance with another embodiment, the present invention provides a process for preparation of a compound of Formula VIII or a salt thereof, comprising:

a) cyclizing a compound of Formula IV to obtain a compound of Formula XII, wherein "P" represents hydrogen or a suitable hydroxyl protecting group;

b) treating the compound of Formula XII with a compound of Formula V to obtain an indole compound of formula VII, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above; and c) reducing the indole compound of formula VII with a suitable reducing agent to obtain an amine compound of Formula VIII or a salt thereof; wherein "P" "R1" and "R2" are defined as above.

In accordance with another embodiment, the present invention provides a process for preparation of a compound of Formula VIII or a salt thereof, comprising:

a) cyclizing a compound of Formula IV' to obtain an indole compound of Formula XV or a salt thereof, Formula XV

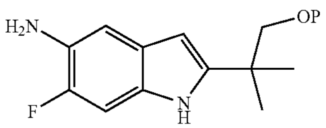

wherein "P" represents hydrogen or a suitable hydroxyl protecting group; and b) treating the compound of Formula XV with a compound of Formula V to obtain a compound of Formula VIII or a salt thereof, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

In accordance with another embodiment, the present invention provides a process for preparation of an acid salt of an amine compound of Formula VIII, comprising:

a) providing a solution of compound of Formula VIII in one or more organic solvents, b) adding a suitable acid to the step a) solution, and c) isolating the compound of Formula VIII as an acid salt.

In accordance with another embodiment, the present invention provides a process for isolation of amine compound of Formula VIII, comprising:

a) providing a solution of compound of Formula VIII in one or more organic solvents, b) adding a suitable acid to the step a) solution, c) isolating the compound of Formula VIII as an acid salt, d) neutralizing the acid salt of compound of Formula VIII with a suitable base, and e) isolating the amine compound of Formula VIII.

In accordance with another embodiment, the present invention provides a process for preparation of Tezacaftor of Formula I, comprising:

a) preparing the compound of Formula VIII or a salt thereof, obtained by the processes as described above embodiments, wherein "R", "R1", "R2" and "P" are defined as above; and b) converting the compound of Formula VIII into Tezacaftor of Formula I.

In accordance with another embodiment, the present invention provides a process for preparation of Tezacaftor of Formula I, comprising:

a) coupling an amine compound of formula VIII or a salt thereof with an acid compound of Formula IX or its reactive derivative thereof to obtain a compound of Formula X, wherein "P" represents hydrogen or a suitable hydroxyl protecting group and "R1" and "R2" may be same or different and represents a hydrogen or an alcoholic protecting group or "R1" and "R2" are taken together to form a diol protecting group; and b) optionally deprotecting the compound of Formula X with a suitable deprotecting agent to obtain Tezacaftor of Formula I.

In accordance with another embodiment, the present invention provides a process for preparation of Tezacaftor of Formula I, comprising:

a) coupling a compound of Formula VII' or a salt thereof with an acid compound of Formula IX or its reactive derivative thereof to obtain a compound of Formula XIV, Formula XIV

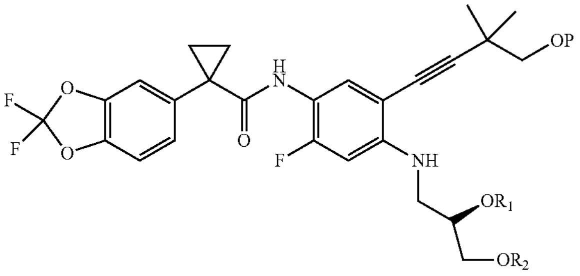

wherein "P" represents hydrogen or a suitable hydroxyl protecting group and "R1" and "R2" may be same or different and represents a hydrogen or an alcoholic protecting group or "R1" and "R2" are taken together to form a diol protecting group;

b) cyclizing the compound of Formula XIV to obtain compound of formula X, wherein "P" "R1" and "R2" are defined as above; and c) optionally deprotecting the compound of Formula X with a suitable deprotecting agent to obtain Tezacaftor of Formula I.

In accordance with another embodiment, the present invention provides a process for purification of a compound of Formula X, comprising:

a) treating a compound of Formula X with one or more organic solvents, and b) isolating the pure compound of Formula X.

In accordance with another embodiment, the present invention provides a process for purification of Tezacaftor Formula I, comprising:

a) treating crude Tezacaftor of Formula I with a suitable organic solvent, and b) isolating the pure Tezacaftor of Formula I.

In accordance with another embodiment, the present invention provides a compound of Formula IV:

Formula IV

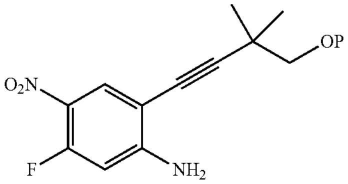

wherein the "P" represents hydrogen or a suitable hydroxyl protecting group.

In accordance with another embodiment, the present invention provides a compound of Formula IV:

Formula IV

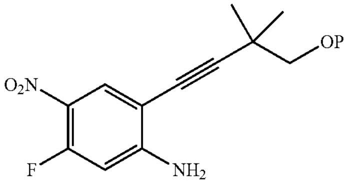

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

In accordance with another embodiment, the present invention provides a compound of Formula IVa.

Formula IVa

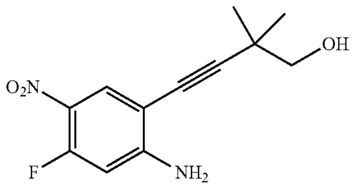

In accordance with another embodiment, the present invention provides a compound of formula IVb.

Formula IVb

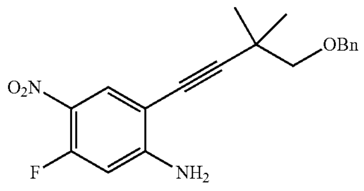

In another embodiment, the present invention provides crystalline compound of Formula IVb.

In another embodiment, the present invention provides compound of Formula IVb characterized by X-Ray powder diffraction (PXRD) pattern substantially in accordance with FIG. 1.

In accordance with another embodiment, the present invention provides a compound of Formula IV':

Formula IV'

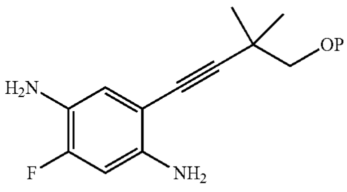

wherein the "P" represents hydrogen or a suitable hydroxyl protecting group.

In accordance with another embodiment, the present invention provides a compound of Formula IV':

Formula IV'

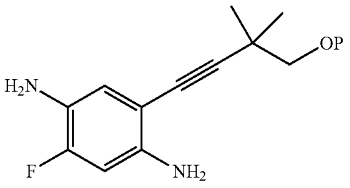

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

In accordance with another embodiment, the present invention provides a compound of Formula IV'a.

Formula IV'a

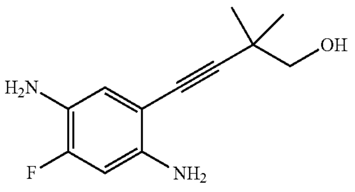

In accordance with another embodiment, the present invention provides a compound of formula IV'b.

Formula IV'b

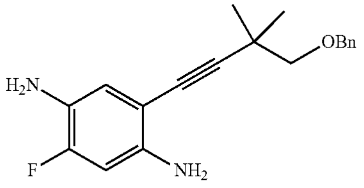

In accordance with another embodiment, the present invention provides a compound of Formula VI:

Formula VI

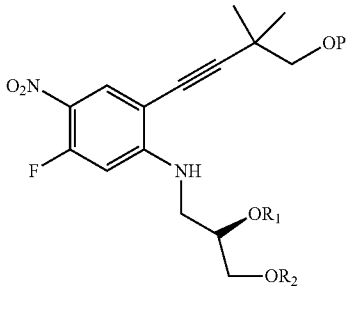

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In accordance with another embodiment, the present invention provides a compound of Formula VI:

Formula VI

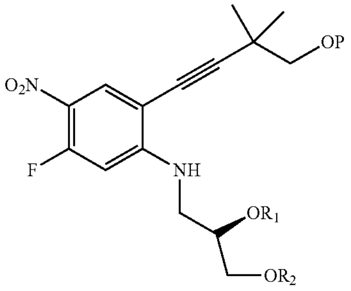

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

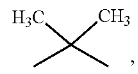 , 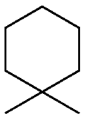 ,

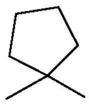 and 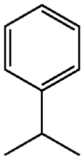 .

In accordance with another embodiment, the present invention provides a compound of Formula VIa.

Formula VIa

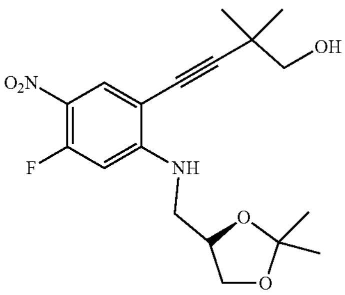

In accordance with another embodiment, the present invention provides a compound of formula VIb.

Formula VIb

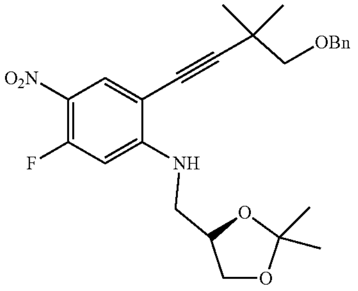

In another embodiment, the present invention provides crystalline compound of Formula VIb.

In another embodiment, the present invention provides compound of Formula VIb characterized by X-Ray powder diffraction (PXRD) pattern substantially in accordance with FIG. 2.

In accordance with another embodiment, the present invention provides a compound of Formula VI':

Formula VI'

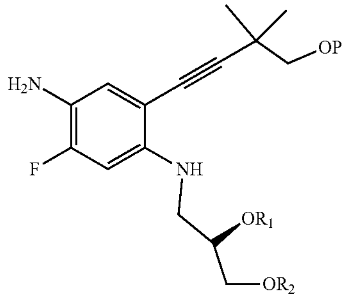

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In accordance with another embodiment, the present invention provides a compound of Formula VI':

Formula VI'

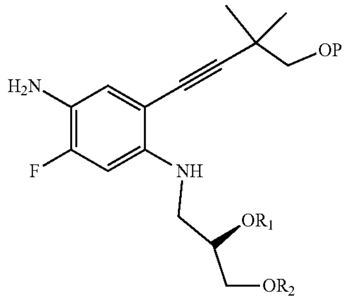

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

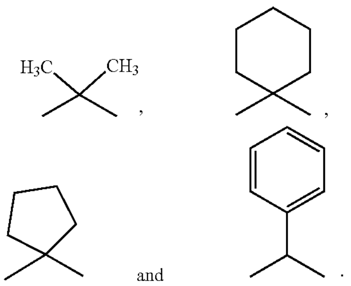

,  ,  and  .

In accordance with another embodiment, the present invention provides a compound of Formula VI'a or a compound of formula VI'b.

Formula VI'a

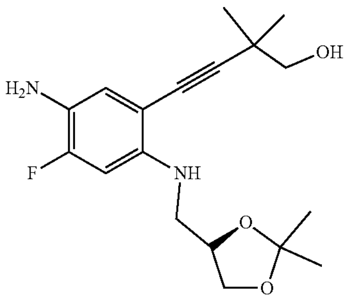

Formula VI'b

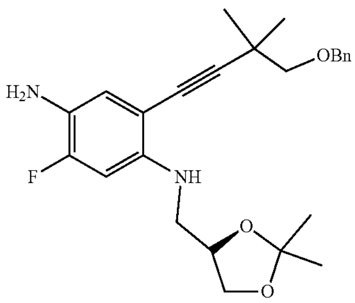

In accordance with another embodiment, the present invention provides a compound of Formula VII:

Formula VII

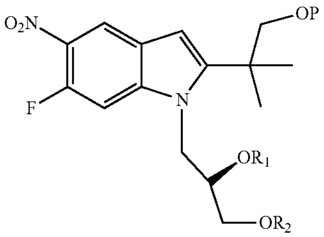

wherein the "P" represents hydrogen or a suitable hydroxyl protecting group and "R1" and "R2" may be same or different and represents a hydrogen or an alcoholic protecting group or "R1" and "R2" are taken together to form a diol protecting group. In accordance with another embodiment, the present invention provides a compound of Formula VII:

Formula VII

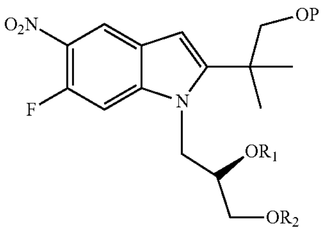

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

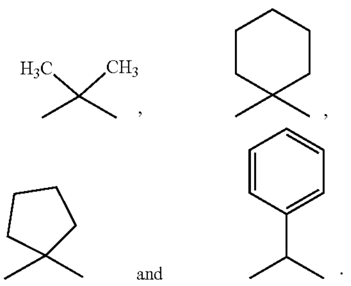

,  ,  and  .

In accordance with another embodiment, the present invention provides a compound of Formula VIIa or a compound of formula VIIb.

Formula VIIa

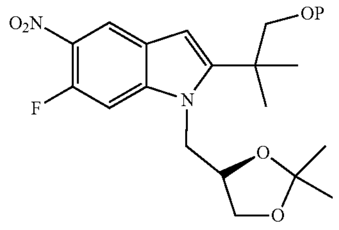

Formula VIIb

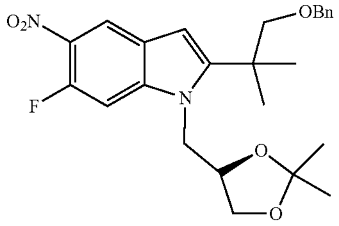

In accordance with another embodiment, the present invention provides a compound of Formula VII':

Formula VII'

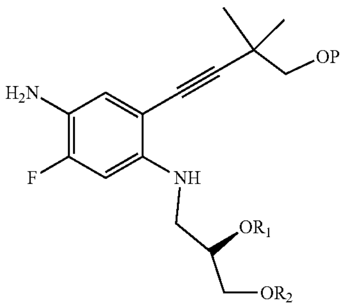

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In accordance with another embodiment, the present invention provides a compound of Formula VII':

Formula VII'

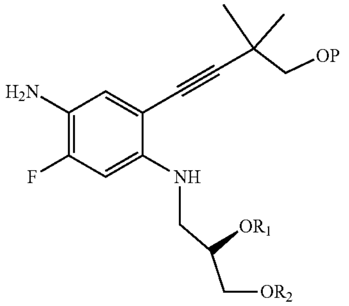

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

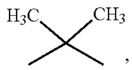 ,
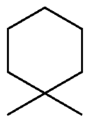 ,
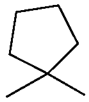 and 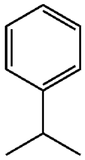 .

In accordance with another embodiment, the present invention provides a compound of Formula VII'a or a compound of formula VII'b.

Formula VII'a

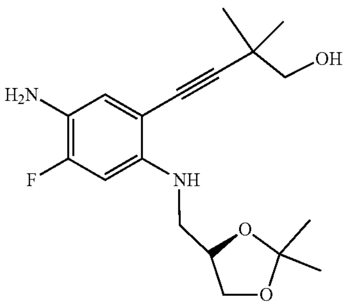

Formula VII'b

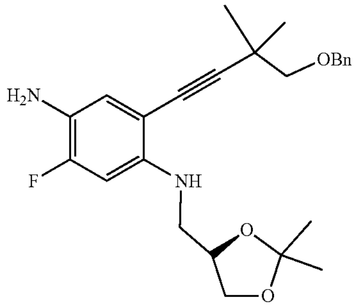

In accordance with another embodiment, the present invention provides a compound of Formula VIII:

Formula VIII

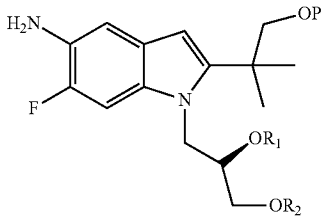

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In accordance with another embodiment, the present invention provides a compound of Formula VIII:

Formula VIII

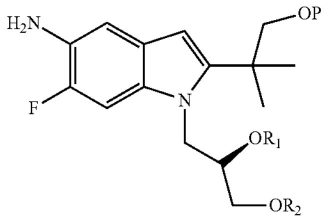

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

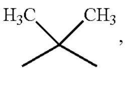, 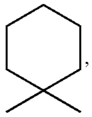, 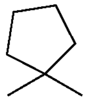 and 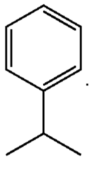.

In accordance with another embodiment, the present invention provides a compound of Formula VIIIa.

Formula VIIIa

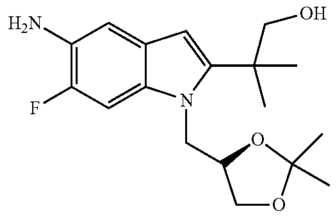

In accordance with another embodiment, the present invention provides a compound of formula VIIIb.

Formula VIIIb

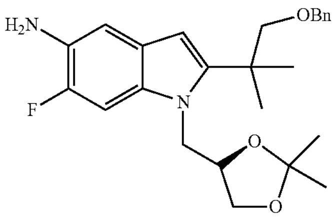

In accordance with another embodiment, the present invention provides acid salt of an amine compound of Formula VIIIb.

In accordance with another embodiment, the present invention provides oxalic acid salt of an amine compound of Formula VIII.

In accordance with another embodiment, the present invention provides oxalic acid salt of an amine compound of Formula VIII characterized by an X-ray powder diffraction pattern substantially in accordance with FIG. 3.

In another embodiment, the present invention provides oxalic acid salt of an amine compound of Formula VIIIb characterized by X-ray powder diffraction pattern peaks at about 3.9, 6.8, 7.7, 8.7, 9.3, 10.9, 11.5, 13.2, 13.5, 14.5, 16.0, 16.4, 16.6, 17, 17.5, 18.6, 19.4, 20.0, 22.0, 22.2, 23.2, 25.0, 26.7, 28.1 and 29.2±0.2° 2θ.

In accordance with another embodiment, the present invention provides a compound of Formula X:

Formula X

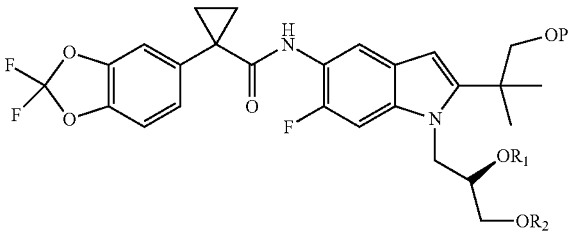

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In accordance with another embodiment, the present invention provides a compound of Formula X:

Formula X

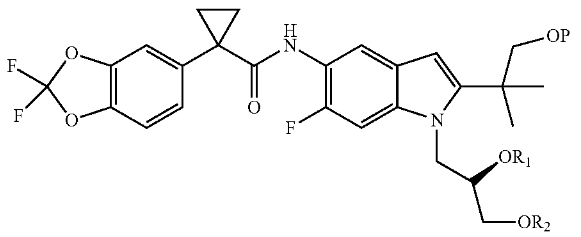

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

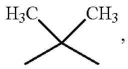, 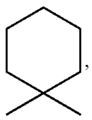, 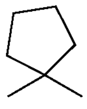 and 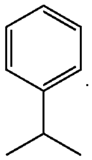.

In accordance with another embodiment, the present invention provides a compound of Formula Xa.

Formula Xa

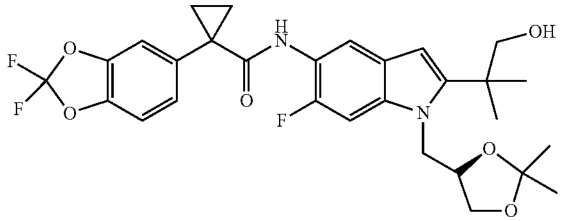

In accordance with another embodiment, the present invention provides a compound of Formula Xb.

Formula Xb

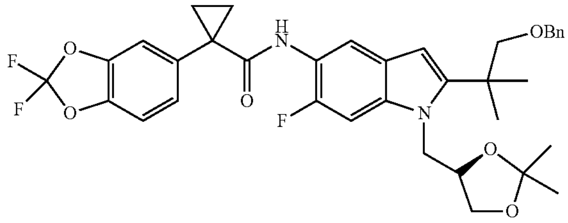

In another embodiment, the present invention provides crystalline compound of Formula Xb.

In another embodiment, the present invention provides compound of Formula Xb characterized by X-Ray powder diffraction (PXRD) pattern substantially in accordance with FIG. 4.

In accordance with another embodiment, the present invention provides a compound of Formula XI:

Formula XI

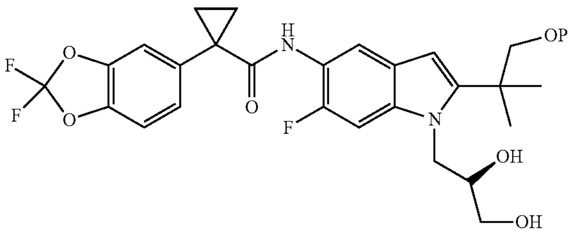

wherein the "P" represents hydrogen or a suitable hydroxyl protecting group.

In accordance with another embodiment, the present invention provides a compound of Formula XI:

Formula XI

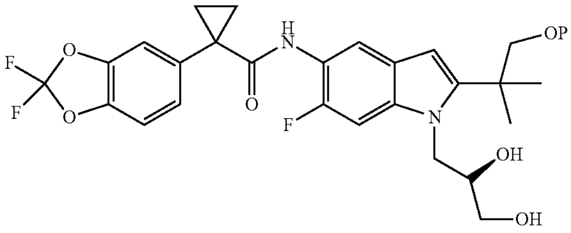

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

In accordance with another embodiment, the present invention provides a compound of Formula XIb.

Formula XIb

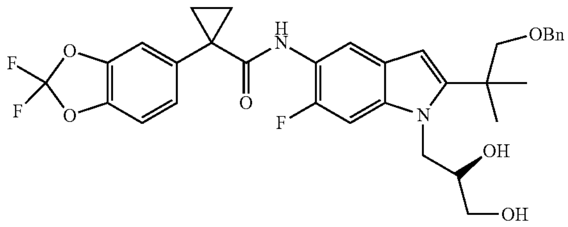

In accordance with another embodiment, the present invention provides a compound of Formula XII.

Formula XII

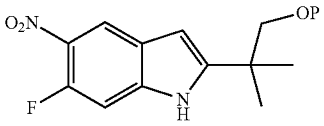

wherein the "P" represents hydrogen or a suitable hydroxyl protecting group.

In accordance with another embodiment, the present invention provides a compound of Formula XII Formula XII

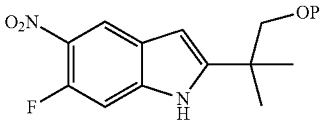

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

In accordance with another embodiment, the present invention provides a compound of Formula XIIa or a compound of Formula XIIb.

Formula XIIa

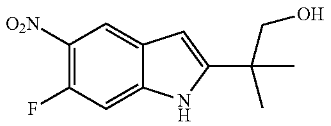

Formula XIIb

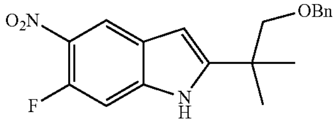

In accordance with another embodiment, the present invention provides a compound of Formula XIII:

Formula XIII

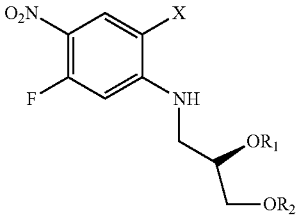

wherein the "X" represents a suitable leaving group and "R1" and "R2" may be same or different and represents a hydrogen or an alcoholic protecting group or "R1" and "R2" are taken together to form a diol protecting group.

In accordance with another embodiment, the present invention provides a compound of Formula XIII:

Formula XIII

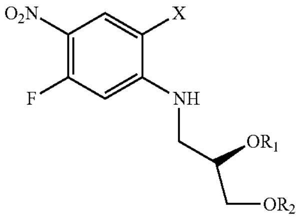

wherein the "X" represents a suitable leaving group selected from the group comprising halogens like fluorine, chlorine, bromine, iodine, methanesulfonyloxy, p-toluenesulfonyloxy, trifluoromethanesulfonyloxy, (4-bromo-benzene) sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, (4-methoxy-benzene)sulfonyloxy, and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

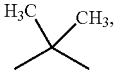 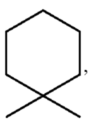, 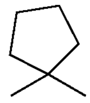 and 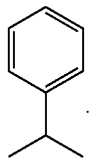.

In accordance with another embodiment, the present invention provides a compound of Formula XIIIa.

Formula XIIIa

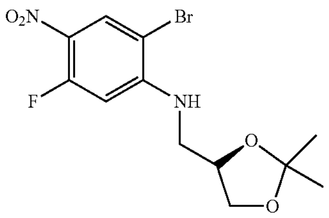

In accordance with another embodiment, the present invention provides a compound of Formula XIII':

Formula XIII'

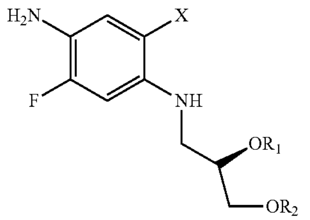

wherein the "X" represents a suitable leaving group and "R1" and "R2" may be same or different and represents a hydrogen or an alcoholic protecting group or "R1" and "R2" are taken together to form a diol protecting group.

In accordance with another embodiment, the present invention provides a compound of Formula XIII':

Formula XIII'

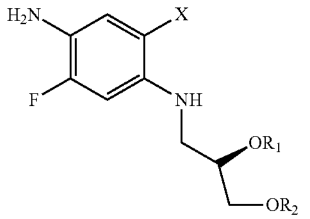

wherein the "X" represents a suitable leaving group selected from the group comprising halogens like fluorine, chlorine, bromine, iodine, methanesulfonyloxy, p-toluenesulfonyloxy, trifluoromethanesulfonyloxy, (4-bromo-benzene) sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, (4-methoxy-benzene)sulfonyloxy, and the like and "R1" and "R2" may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or "R1" and "R2" are taken together to form a diol protecting group independently selected from

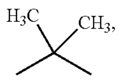 , 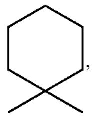 , 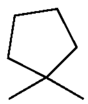 and 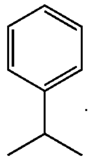 .

In accordance with another embodiment, the present invention provides a compound of Formula XIII'a.

Formula XIII'a

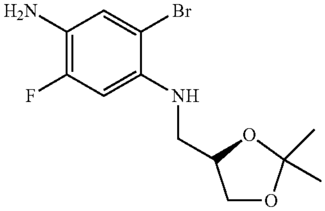

In accordance with another embodiment, the present invention provides a compound of Formula XIV:

Formula XIV

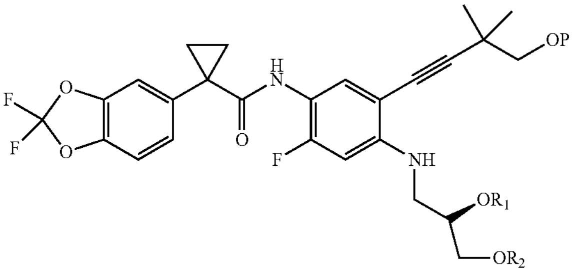

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In accordance with another embodiment, the present invention provides a compound of Formula XIV:

Formula XIV

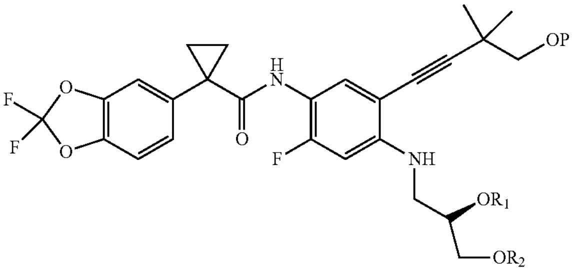

wherein the "P" represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like and “R1” and “R2” may be same or different and represents a hydrogen or an alcoholic protecting group selected from the group comprising tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups or “R1” and “R2” are taken together to form a diol protecting group independently selected from

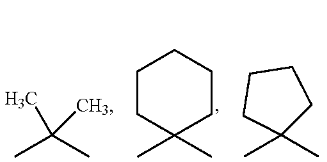

and

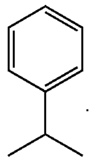

.

and

In accordance with another embodiment, the present invention provides a compound of Formula XIVa or a compound of Formula XIVb.

Formula XIVa

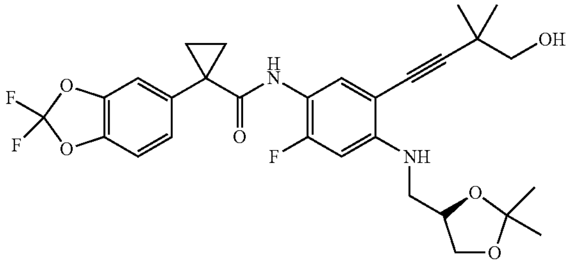

Formula XIVb

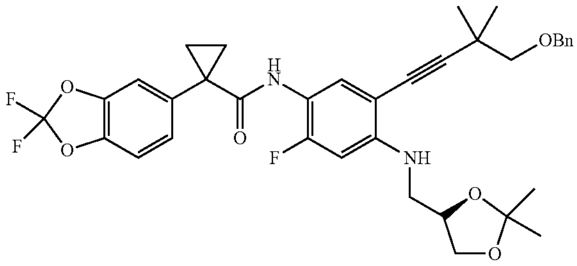

In accordance with another embodiment, the present invention provides a compound of Formula XV:

Formula XV

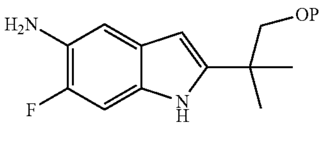

wherein the “P” represents hydrogen or a suitable hydroxyl protecting group.

In accordance with another embodiment, the present invention provides a compound of Formula XV:

Formula XV

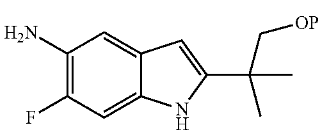

wherein the “P” represents hydrogen or a suitable hydroxyl protecting group selected from the group comprising alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

In accordance with another embodiment, the present invention provides a compound of Formula XVa or a compound of Formula XVb.

Formula XVa

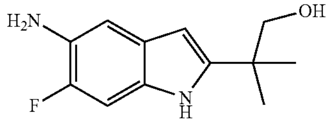

Formula XVb

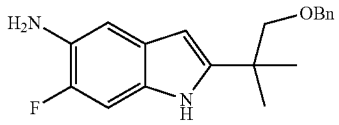

In accordance with another embodiment, the present invention provides a process for preparation of Tezacaftor of Formula I;

Formula I

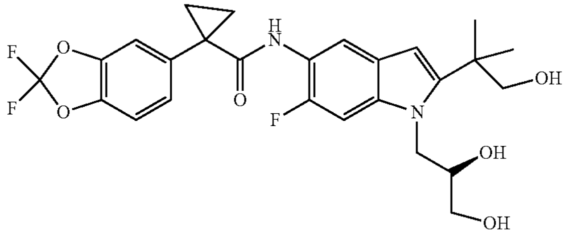

comprising:

a) reacting a compound of Formula IIa

Formula IIa

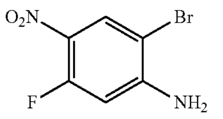

with alkyne of Formula IIb to obtain a compound of Formula IVb;

Formula IIIb

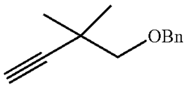

Formula IVb

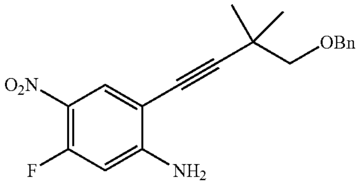

b) treating the compound of Formula IVb with a compound of Formula Va to obtain a compound of formula VIb;

Formula Va

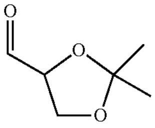

Formula VIb

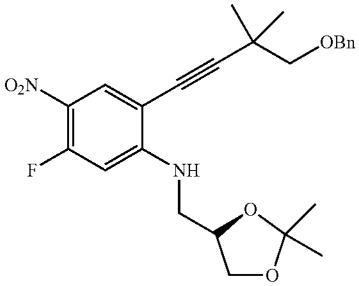

c) cyclizing the compound of Formula VIb to obtain an indole compound of Formula VIIb;

Formula VIIb

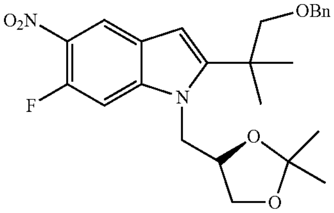

d) reducing the compound of Formula VIIb with a suitable reducing agent to obtain an amine compound of Formula VIIIb or a salt thereof, Formula VIIIb

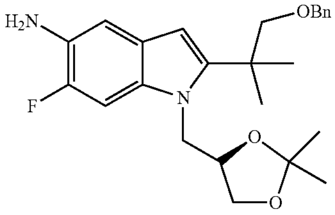

e) coupling the amine compound of formula VIIb or a salt thereof with an acid compound of Formula IX or its reactive derivative thereof to obtain a compound of Formula Xb; and Formula IX

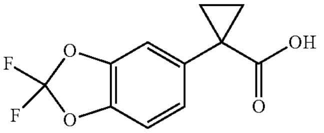

Formula Xb

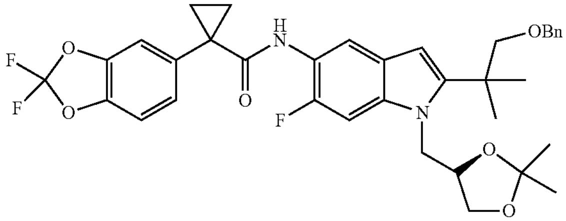

f) deprotecting the compound of Formula Xb with a suitable deprotecting agent to obtain Tezacaftor of Formula I.

In accordance with another embodiment, the present invention provides a process for preparation of Tezacaftor of Formula I;

Formula I

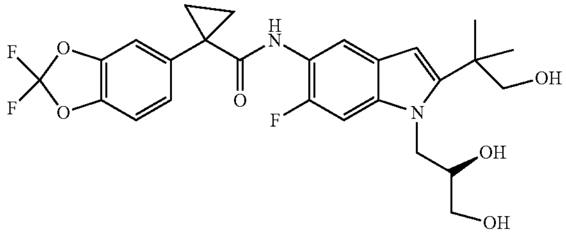

comprising:

a) reacting a compound of Formula IIa

Formula IIa

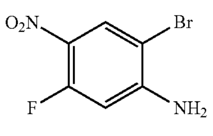

with alkyne of Formula IIIb to obtain a compound of Formula IVb;

Formula IIIb

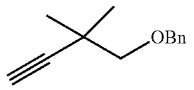

Formula IVb

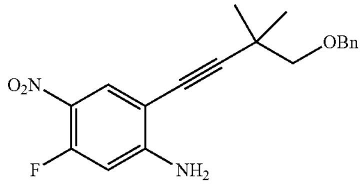

b) treating the compound of Formula IVb with a compound of Formula Va to obtain a compound of formula VIb;

Formula Va

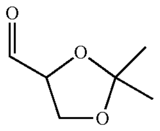

Formula VIb

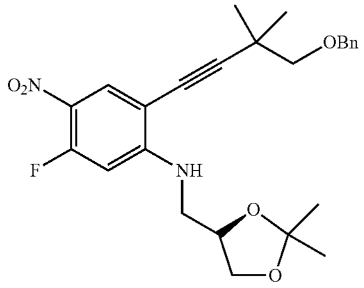

c) reducing the compound of Formula VIb with a suitable reducing agent to obtain a compound of Formula VII'b;

Formula VII'b

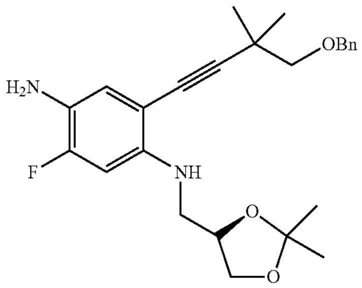

d) cyclizing the compound of Formula VII'b to obtain an amine compound of Formula VIIIb or a salt thereof, Formula VIIIb

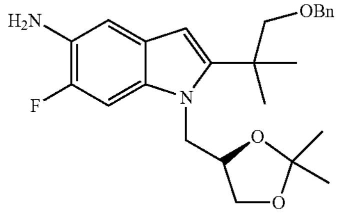

e) coupling the amine compound of formula VIIIb or a salt thereof with an acid compound of Formula IX or its reactive derivative to obtain a compound of Formula Xb; and Formula IX

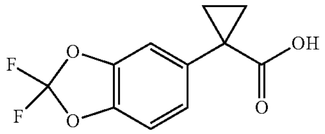

Formula Xb

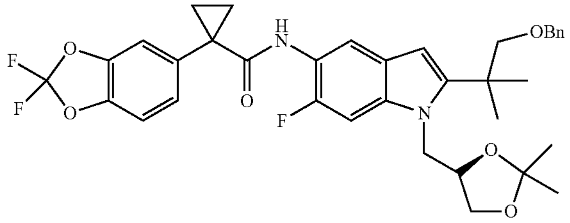

f) deprotecting the compound of Formula Xb with a suitable deprotecting agent to obtain Tezacaftor of Formula I.

In accordance with another embodiment, the present invention provides a process for preparation of Tezacaftor of Formula I;

Formula I

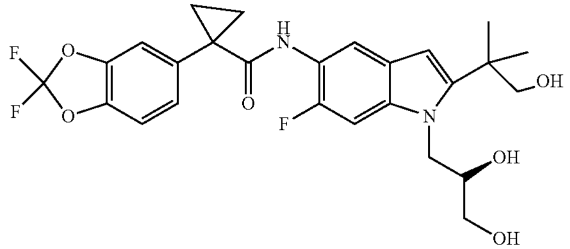

comprising:

a) cyclizing a compound of Formula IVb to obtain a compound of Formula XIIb;

Formula XIIb

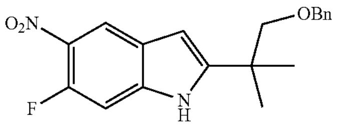

b) treating the compound of Formula XIIb with a compound of Formula Va or Vb or Vc to obtain an indole compound of formula VIIb; and c) converting the indole compound of Formula VIIb in to Tezacaftor of Formula I.

In accordance with another embodiment, the present invention provides a process for preparation of Tezacaftor of Formula I;

Formula I

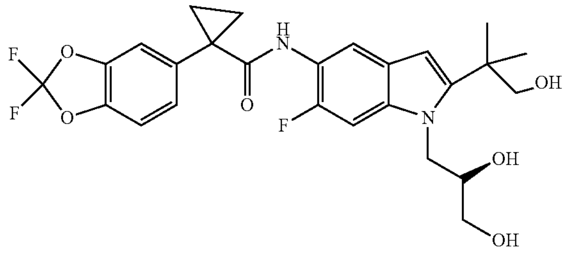

comprising:

a) treating a compound of formula IIa with a compound of Formula Va or Vb or Vc to obtain a compound of Formula XIIIa;

Formula XIIIa

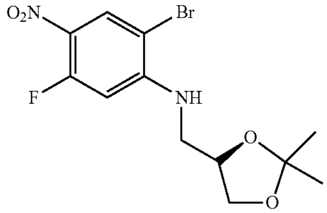

b) reacting the compound of Formula XIIIa with an alkyne of Formula IIIb to obtain a compound of Formula VIb; and c) converting the compound of Formula VIb in to Tezacaftor of Formula I.

In accordance with another embodiment, the present invention provides compound of Formula VIb having less than 0.5% as measured by HPLC of one or more of impurities of Formula A, Formula B, Formula C or Formula D:

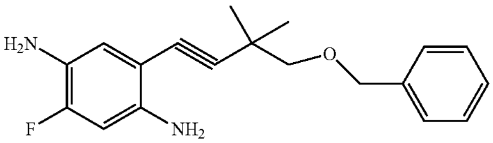

Diamino impurity of Formula A

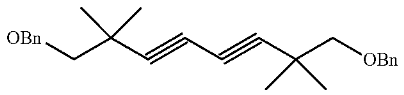

Dimethyl butyne dimer impurity of Formula B

-continued

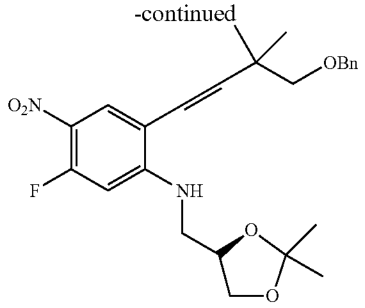

Ene impurity of Formula C

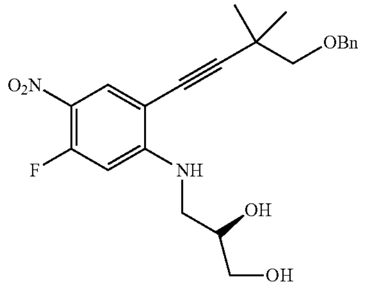

Dioxalane-Diol impurity of Formula D

In accordance with another embodiment, the present invention provides compound of Formula Xb having less than 0.1% des fluoro impurity of Formula E as measured by HPLC:

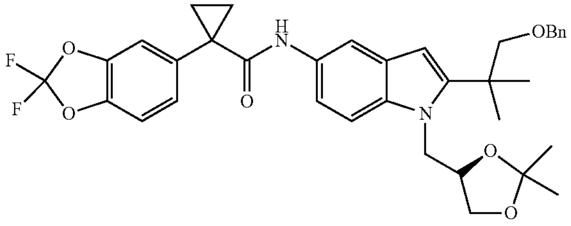

Des fluoro impurity of Formula E

In accordance with another embodiment, the present invention provides Tezacaftor of Formula I contains less than 0.1% of Tetramethyl impurity of Formula F as determined by HPLC.

In accordance with another embodiment, the present invention provides Tezacaftor of Formula I contains less than 0.1% of N-Ethyl impurity of Formula G as determined by HPLC.

In accordance with another embodiment, the present invention provides Tezacaftor of Formula I contains less than 0.1% of Di-hydro impurity of Formula H as determined by HPLC.

In accordance with another embodiment, the present invention provides Tezacaftor of Formula I having a total purity of greater than 99.5%, as measured by HPLC.

In accordance with another embodiment, the present invention provides Tezacaftor of Formula I contains less than 0.1% of each of Tetramethyl impurity of Formula F, N-Ethyl impurity of Formula G and Di-hydro impurity of Formula H as measured by HPLC. In accordance with another embodiment, the present invention provides a compound of Formula A;

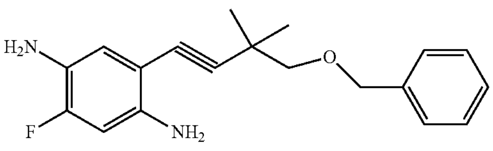

Diamino impurity of Formula A

In accordance with another embodiment, the present invention provides a compound of Formula B;

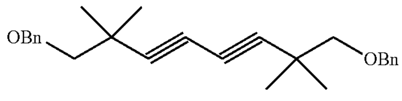

Dimethyl butyne dimer impurity of Formula B

In accordance with another embodiment, the present invention provides a compound of Formula C;

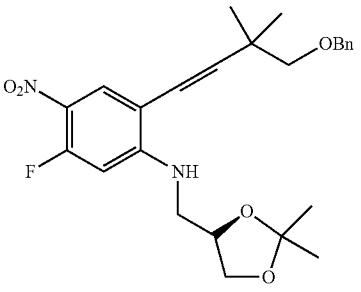

Ene impurity of Formula C

In accordance with another embodiment, the present invention provides a compound of Formula D;

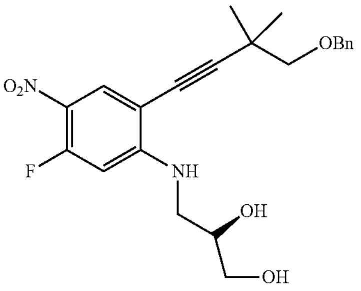

Dioxalane-Diol impurity of Formula D

In accordance with another embodiment, the present invention provides a compound of Formula E;

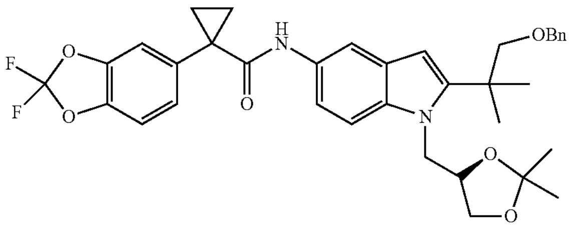

Des fluoro impurity of Formula E

In accordance with another embodiment, the present invention provides a compound of Formula F;

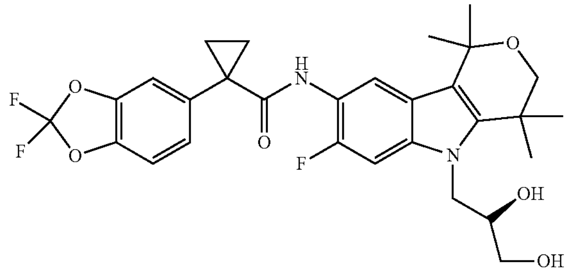

Tetramethyl impurity of Formula F

In accordance with another embodiment, the present invention provides a compound of Formula G;

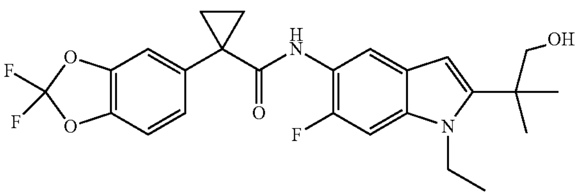

N-Ethyl impurity of Formula G

In accordance with another embodiment, the present invention provides a compound of Formula H;

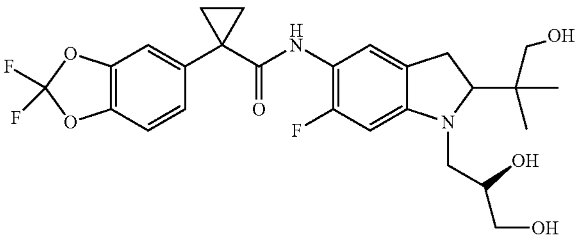

Di-hydro impurity of Formula H

In accordance with another embodiment, the present invention provides a pharmaceutical composition comprising Tezacaftor prepared by the processes of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
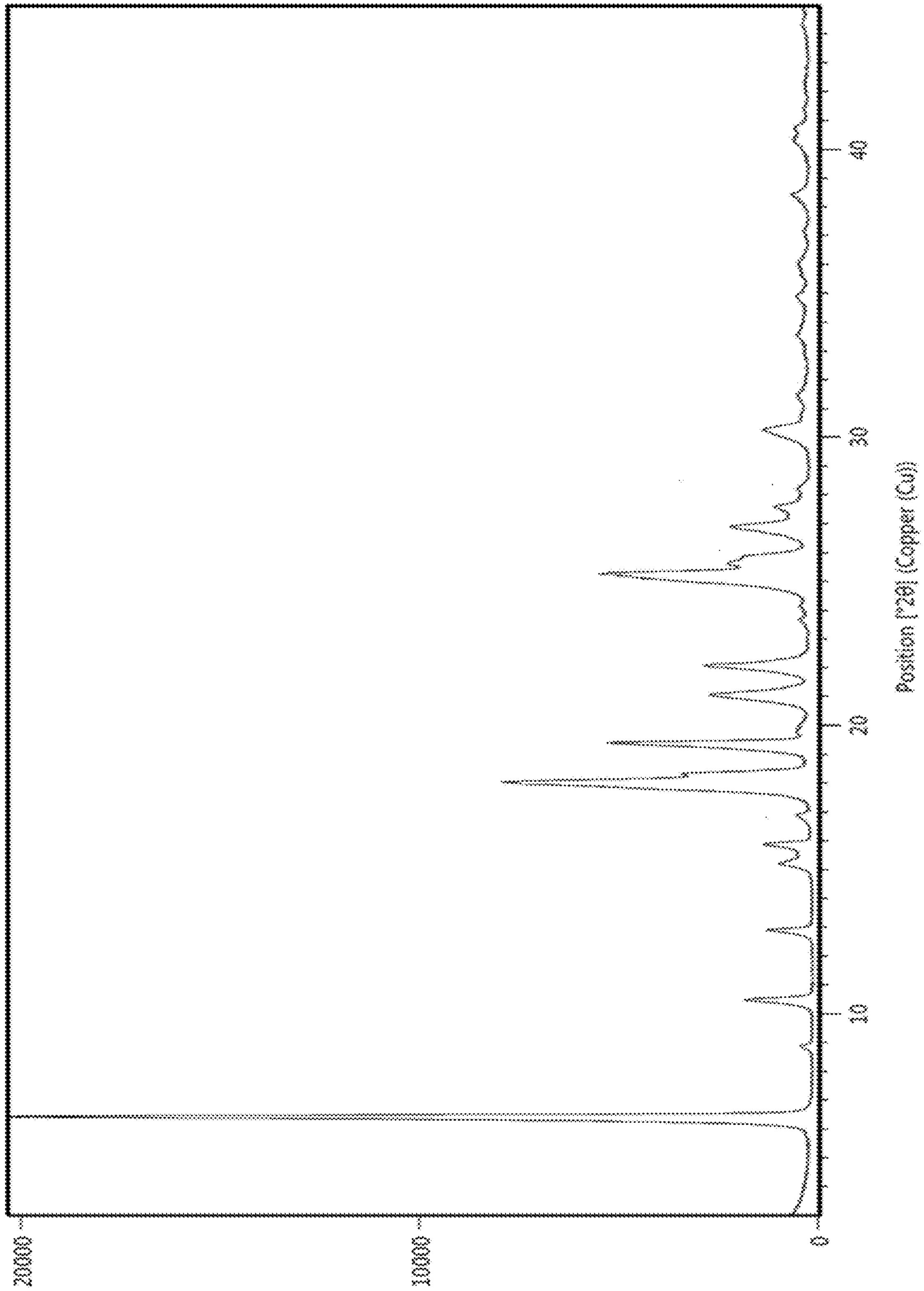
FIG. 1 is the characteristic powder XRD pattern of compound of Formula IVb.

The present invention relates to processes for the preparation of Tezacaftor of Formula I using novel intermediates.

In accordance with one embodiment, the present invention provides a process for preparation of Tezacaftor of Formula I;

Formula I

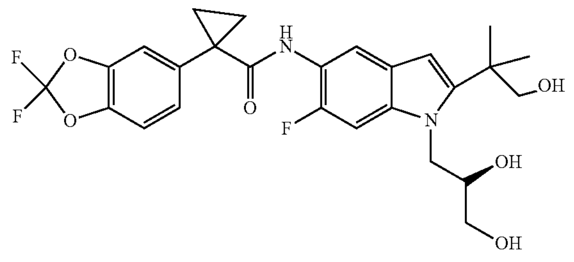

comprising:

a) reacting a compound of Formula II with an alkyne of Formula III to obtain a compound of Formula IV, Formula II

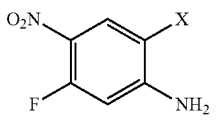

Formula III

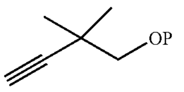

wherein "X" represents a suitable leaving group and "P" represents hydrogen or a suitable hydroxyl protecting group;

Formula IV

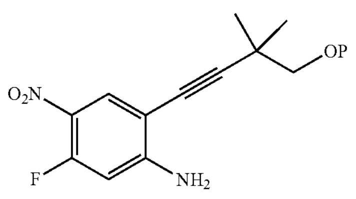

b) treating the compound of Formula IV with a compound of Formula V to obtain a compound of formula VI, Formula V

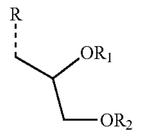

Formula VI

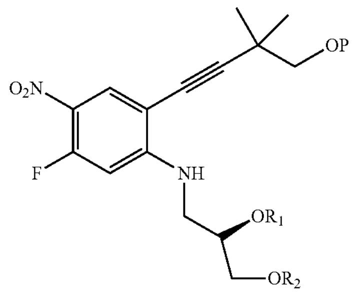

wherein "P" represents hydrogen or a suitable hydroxyl protecting group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group;

c) cyclizing the compound of Formula VI to obtain a compound of Formula VII followed by reduction with a suitable reducing agent to obtain an amine compound of Formula VIII or a salt thereof; or, reducing the compound of Formula VI with a suitable reducing agent to obtain a compound of Formula VII' followed by cyclization to obtain an amine compound of Formula VIII or a salt thereof, Formula VII

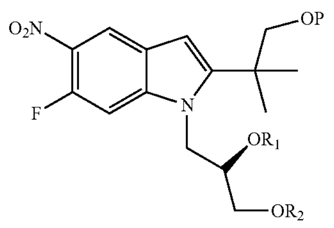

Formula VII'

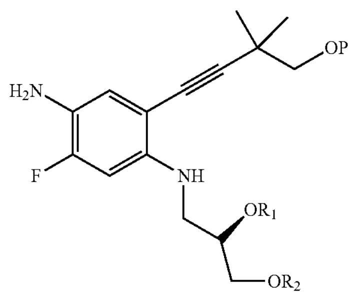

-continued

Formula VIII

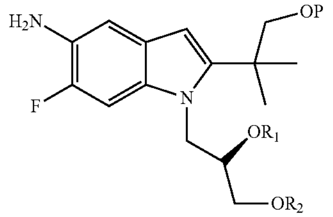

wherein “P” “R1” and “R2” are defined as above;

d) coupling the amine compound of formula VIII or a salt thereof with an acid compound of Formula IX or its reactive derivative thereof to obtain a compound of Formula X;

Formula IX

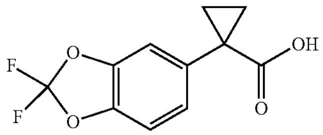

Formula X

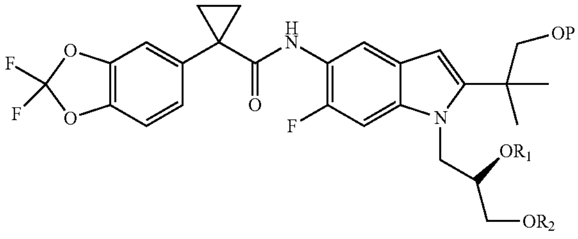

wherein “P” “R1” and “R2” are defined as above; and e) optionally deprotecting the compound of Formula X with a suitable deprotecting agent to obtain Tezacaftor of Formula I.

In another embodiment, the present invention provides a process for preparation of a compound of Formula VIII or a salt thereof;

Formula VIII

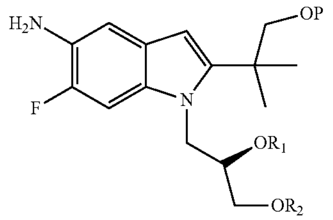

comprising:

a) reacting a compound of Formula II with an alkyne of Formula III to obtain a compound of Formula IV, Formula II

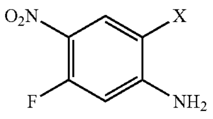

-continued

Formula III

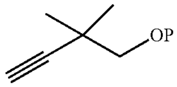

wherein “X” represents a suitable leaving group and “P” represents hydrogen or a suitable hydroxyl protecting group;

Formula IV

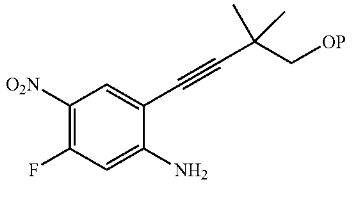

b) treating the compound of Formula IV with a compound of Formula V to obtain a compound of formula VI, Formula V

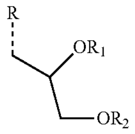

Formula VI

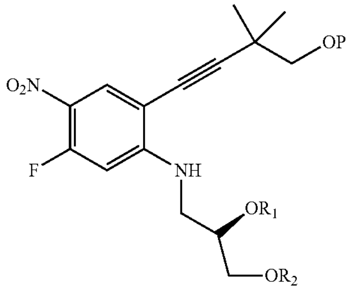

wherein “P” represents hydrogen or a suitable hydroxyl protecting group, “R” represents an oxygen atom or a suitable leaving group and dotted line represents a single bond or a double bond and “R1” and “R2” may be same or different and represents a hydrogen or an alcoholic protecting group or “R1” and “R2” are taken together to form a diol protecting group; and c) cyclizing the compound of Formula VI to obtain a compound of Formula VII followed by reduction with a suitable reducing agent to obtain an amine compound of Formula VIII or a salt thereof; or, reducing the compound of Formula VI with a suitable reducing agent to obtain a compound of Formula VII' followed by cyclization to obtain an amine compound of Formula VIII or a salt thereof, Formula VII

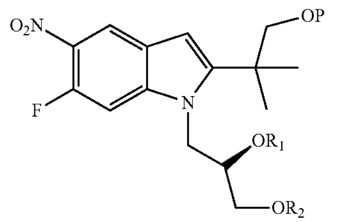

Formula VII'

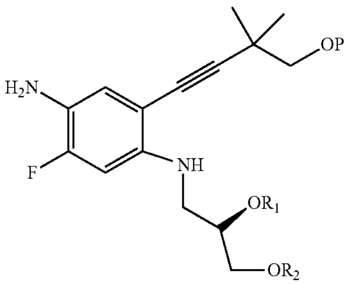

wherein "P" "R1" and "R2" are defined as above.

Unless otherwise specified the term "X" used herein represents a suitable leaving group. Unless otherwise specified the term "R" used herein represents an oxygen atom or a suitable leaving group.

Examples of suitable leaving group include, but are not limited to halogens (e.g., fluorine, chlorine, bromine, iodine), methanesulfonyloxy, p-toluenesulfonyloxy, trifluoromethanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, (4-methoxy-benzene)sulfonyloxy, and the like.

Unless otherwise specified the substituents "P" represents hydrogen or a "suitable hydroxyl protecting group". Examples of hydroxyl protecting groups include, but are not limited, to alkyl, allyl, pivaloyl, acetyl (Ac), tosyl (Ts), mesyl (Ms), silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like.

Unless otherwise specified the substituents "R1" and "R2" may be same or different and represents a hydrogen or an alcoholic protecting group or "R1" and "R2" are taken together to form a diol protecting group. Examples of alcoholic protecting groups include, but are not limited, to tetrahydropyranyl, benzyl, methyl, silyl groups like trimethylsilyl, triethylsilyl, triisopropylsilyl, tertiraybutyldipropyl silyl, t-butyldimethylsilyl and t-butyldiphenyl groups and diol protecting groups include, but are not limited, to

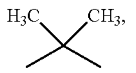, 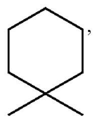, 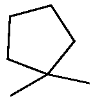 and 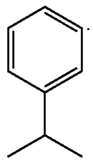.

The starting compounds of Formula II and III are known in the art and are available commercially from various sources or can be prepared by the processes known in the art, for example, U.S. Pat. No. 9,035,072.

The step a) of the aforementioned process involves the reaction of a compound of Formula II, wherein the 'X' represents a suitable leaving group preferably halogen selected from fluorine, chlorine, bromine or iodine, more preferably bromine, with an alkyne compound of Formula III, wherein the "P" represents hydrogen or a suitable hydroxyl protecting group, preferably hydrogen or Benzyl group, to obtain a compound of Formula IV.

Typically, the step a) reaction of the compound of Formula II with the alkyne compound of Formula III may be carried out in presence of a suitable catalyst, a suitable ligand, a suitable base and a suitable solvent.

The suitable catalyst used for step a) reaction include, but is not limited to bis(dibenzylideneacetone)palladium [Pd (dba)2], tris(dibenzylideneacetone) dipalladium [Pd2(dba) 3], Palladium(II) chloride [$PdCl_2$], palladium(II)acetate [Pd (OAc)2], bis(triphenylphosphine)palladium(II) dichloride [$PdCl2(PPh_3)_2$], [1,1'-bis(diphenylphosphino) ferrocene]dichloropalladium(II) [Pd(dppf)$Cl_2$], tetrakis (triphenylphosphine)palladium [Pd(PPh3)4], copper, cuprous bromide, cuprous iodide, 2,2'-bis-diphenylphosphanyl[1,1'] binaphtalenyl (rac-Binap), allylpalladium(II) chloride dimer {$[PdCl(C_3H_5)]_2$} and the like and mixtures thereof; preferably the suitable catalyst is palladium(II)acetate [Pd(OAc) 2], Palladium(II) chloride, tetrakis (triphenylphosphine)palladium [Pd(PPh3)4], cuprous iodide, cuprous bromide; more preferably a combination of palladium(II)acetate [Pd(OAc) 2] and cuprous iodide. The suitable ligand used for step a) reaction include, but is not limited to 1,2-bis(diphenylphosphino)ethane (dppe): 1,4-bis(diphenylphosphino)-butane (dppb), Triphenylphosphine ($PPh_3$), 4,5-bis(diphenylphosphino)-9,9-dimethylxanthene [xantphos], 2,2'-bis(diphenylphosphino)-1,1'-binaphthalene [BINAP], 1,1'-bis(diphenyl phosphine) ferrocene [DPPF], 2-(diphenyl phosphine phenyl) ether [DPEphos], tri-t-butyl phosphine [Fu's salt], 2-dicyclohexylphosphino-2'-(N,N-dimethylamino)biphenyl [DavePhos], 2-di-tert-butylphosphino-2'-(N,N-dimethylamino) biphenyl [t-BuDavePhos], trialkyl phosphines and the like and mixtures thereof; preferably the suitable ligand is 1,4-bis(diphenylphosphino)-butane (dppb).

The suitable base used for step a) reaction include, but is not limited to inorganic bases selected from alkali metal hydroxides such as lithium hydroxide, sodium hydroxide, potassium hydroxide and the like; alkali metal alkoxides such as sodium methoxide, sodium ethoxide, sodium tert-butoxide, potassium tert-butoxide and the like; alkali metal carbonates such as sodium carbonate, potassium carbonate, cesium carbonate and the like; alkali metal bicarbonates such as sodium bicarbonate, potassium bicarbonate and the like; organic bases selected from the group consisting of triethylamine, isopropyl ethylamine, diisopropyl amine, diisopropyl ethylamine, N-methyl morpholine, pyridine and the like and mixtures thereof; preferably the suitable base is sodium hydroxide, sodium methoxide, potassium tert-butoxide, sodium carbonate, potassium carbonate, diisopropyl amine or triethylamine; more preferably potassium carbonate.

The suitable solvent used for step a) reaction include, but is not limited to nitriles, ethers, halogenated hydrocarbons, sulfoxides, ketones, amides and mixtures thereof. The nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform and the like; sulfoxides include, but are not limited to dimethylsulfoxide, diethyl sulfoxide and the like; ketones include, but are not limited to acetone, methyl isobutyl ketone, methyl ethyl ketone and the like; amides include, but are not limited to dimethyl formamide, dimethyl acetamide, N-methyl pyrrolidinone and the like and mixtures thereof; preferably the suitable solvent is methyl tertiary butyl ether, methylene chloride, methyl ethyl ketone, acetonitrile, dimethyl formamide; more preferably acetonitrile.

The step a) reaction is carried out at a temperature of about 15° C. to reflux temperature; preferably at about 15° C. to about 95° C.

The resultant compound of Formula IV thus formed can be isolated or further processed without isolating it in to next reaction by reacting with a compound of Formula V to obtain a compound of Formula VI.

In another embodiment, the compound of Formula IV obtained according to the processes of the invention can be isolated.

The isolation step involves distillation off the solvent completely from the reaction mixture under reduced pressure at below 50° C. and the obtained residue may be dissolved in a suitable solvent and isolating the compound of Formula IV by techniques known in the art, for example, filtration.

The suitable solvent used herein for isolation of compound of Formula IV is selected from the group consisting of alcohols, aromatic hydrocarbons, aliphatic or cyclic hydrocarbons and mixtures thereof. The alcohols include, but are not limited to methanol, ethanol, isopropanol, n-propanol, n-butanol, isobutanol and the like; aromatic hydrocarbons include, but are not limited to toluene, xylene and the like; aliphatic or cyclic hydrocarbons include, but are not limited to n-hexane, n-heptane, cyclohexane, cycloheptane and the like and mixtures thereof; preferably toluene, methanol, n-heptane, cyclohexane; more preferably a mixture of Toluene and cyclohexane.

In another embodiment, the present invention provides a compound of Formula IV:

Formula IV

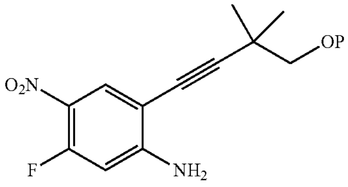

wherein the "P" represents hydrogen or a suitable hydroxyl protecting group.

In a preferred embodiment, the present invention provides a compound of Formula IVa Formula IVa

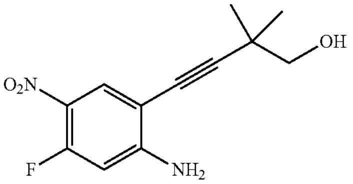

In a preferred embodiment, the present invention provides a compound of formula IVb.

Formula IVb

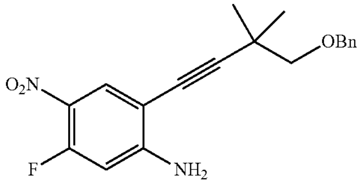

In another embodiment, the present invention provides crystalline compound of Formula IVb.

In another embodiment, the present invention provides compound of Formula IVb characterized by X-Ray powder diffraction (PXRD) pattern substantially in accordance with FIG. 1.

In another embodiment, the present invention provides compound of Formula IVb characterized by X-Ray powder diffraction (PXRD) pattern peaks at about 6.5, 17.8, 18.0, 18.3, 19.4, 21.1, 22.1, 25.0, 253, 25.6 and 26.9 0.2° 2θ

In another embodiment, the compound of Formula IV obtained according to the process of the invention can be used as an intermediate or as a starting material in the preparation of Tezacaftor of Formula I.

The step b) of the aforementioned process involves reaction of the compound of Formula IV, wherein the "P" represents a hydrogen or a suitable hydroxyl protecting group such as benzyl with a compound of formula V to obtain a compound of formula VI at a temperature of about −25° C. to about 55° C.

The compound of Formula V is represented as follows:

Formula V

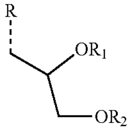

wherein "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group;

In a preferred embodiment, the present invention provides a compound of Formula V specifically represented as Formula Va, Formula Vb or Formula Vc.

Formula Va

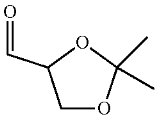

Formula Vb

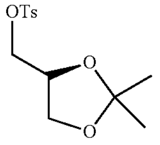

Formula Vc

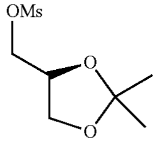

The reaction of the compound of Formula IV with the compound of Formula V may be carried out in presence of an acid, a reducing agent and a solvent to obtain a compound of Formula VI.

The acid used herein includes, but is not limited to formic acid, acetic acid, trichloroacetic acid, trifluoroacetic acid, 2,2,2-triflouroethanol, tin chloride, thiourea, titanium isopropoxide, indium chloride, indium bromide, boric acid, p-toluenesulfonic acid monohydrate, benzoic acid and the like and mixtures thereof; preferably the acid is trifluoroacetic acid.

The reducing agent used herein includes, but is not limited to silanes such as triethylsilane, tri-iso-propylsilane, polymethylhydrosiloxane, phenylsilane, diphenyl silane, triphenyl silane; metal catalysts such as nickel, copper, iron, cobalt, ruthenium, rhodium, palladium, osmium, iridium and platinum or mixtures thereof in presence of hydrogen gas or hydrogen donor such as formic acid; borohydride reagents such as sodium borohydride ($NaBH_4$), sodium cyanoborohydride ($NaCNBH_3$), sodium triacetoxyborohydride ($NaBH(OAc)_3$); 2-picolineborane; α-picoline-borane; decaborane, boric acid and the like and mixtures thereof; preferably the reducing agent is sodium borohydride or sodium triacetoxyborohydride.

The solvent used herein includes, but is not limited to alcohols such as methanol, ethanol, isopropanol and the like; hydrocarbons such as toluene, xylene, chlorobenzene, and the like; haloalkanes such as methylene chloride, chloroform, ethylene dichloride, and the like; esters such as methyl acetate, ethyl acetate, n-propyl acetate, isopropyl acetate, tert-butyl acetate and the like; ethers such as dimethyl ether, diethyl ether, diisopropyl ether, tert-butyl methyl ether, tetrahydrofuran, dioxane and the like and mixtures thereof; preferably the solvent is toluene, tert-butyl methyl ether, methylene chloride or tetrahydrofuran; more preferably toluene or tetrahydrofuran.

In another embodiment, the present invention provides a process for the preparation of compound of Formula VI by reaction of a compound of Formula IV with a compound of formula Va.

In a preferred embodiment, the present invention provides a process for the preparation of compound of Formula VIb by reaction of the compound of Formula IVb with the compound of formula Va.

The resultant compound of Formula VI thus formed can be isolated or further processed without isolating it in to next reaction.

The compound of Formula VI, preferably the compound Formula VIb thus obtained by the process of the present invention may contain Diamino impurity of Formula A, Dimethyl butyne dimer impurity of Formula B, Ene impurity of Formula C and Dioxalane-Diol impurity of Formula D, which are present in the range of about 0.5% to about 5% by HPLC and each impurity represented as follows:

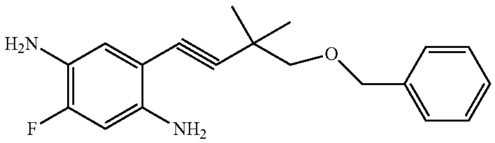

Diamino impurity of Formula A

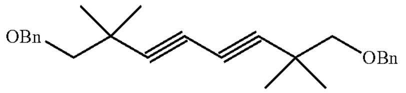

Dimethyl butyne dimer impurity of Formula B

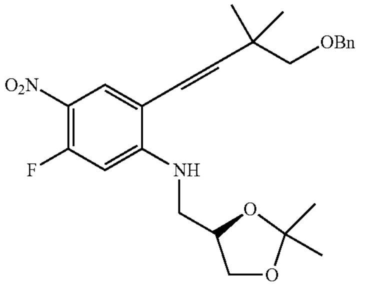

Ene impurity of Formula C

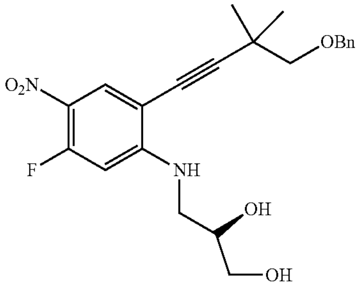

Dioxalane-Diol impurity of Formula D

Without removing these impurities at this stage of the synthesis, the same may carry forward to further steps in subsequent reactions and generates corresponding impurities in each stage up to the final stage formation of Tezacaftor, as a result getting the final product with low product yields and purity. In order to remove these impurities from each stage of the synthesis requires multiple purification processes that make the process lengthy and not viable on commercial scale.

Thus the present invention provides purification of compound of Formula VI, in order to remove impurities at this step effectively and avoid repetitive purifications to separate impurities at each stage of the synthesis up to the final API.

In another embodiment, the present invention provides a process for purification of a compound of Formula VI, wherein the "P" represents hydrogen or a suitable hydroxyl protecting group preferably benzyl using a suitable solvent system.

In another embodiment, the present invention provides a process for purification of a compound of Formula VI, wherein the "P" represents hydrogen or a suitable hydroxyl protecting group preferably benzyl, comprising:

a) treating a compound of Formula VI with a suitable solvent, and b) isolating the pure compound of Formula VI.

In another embodiment, the present invention provides a process for purification of a compound of Formula VI having more than 0.1% of each of Impurity A, Impurity B, Impurity C or Impurity D, comprising:

a) treating a compound of Formula VI with a suitable solvent, and b) isolating the pure compound of Formula VI.

The purification may be carried out by treating the compound of Formula VI with a suitable solvent then the resultant reaction solution may optionally be cooled to less than room temperature for product precipitation followed by isolating the pure compound of Formula VI by techniques known in the art, for example, filtration.

The suitable solvent used herein for purification of compound of Formula IV is selected from the group consisting of water, alcohols, aromatic hydrocarbons, aliphatic or cyclic hydrocarbons and mixtures thereof. The alcohols include, but are not limited to methanol, ethanol, isopropanol, n-propanol, n-butanol, isobutanol and the like; aromatic hydrocarbons include, but are not limited to toluene, xylene and the like; aliphatic or cyclic hydrocarbons include, but are not limited to n-hexane, n-heptane, cyclohexane, cycloheptane and the like a and mixtures thereof; preferably the suitable solvent is methanol, isopropanol, n-heptane, cyclohexane, water and mixtures thereof; more preferably a mixture of isopropanol and water.

The compound of Formula VI; preferably the compound of Formula VIb thus obtained according to purification process of the present invention having less than 0.10% of each of Impurity A, Impurity B, Impurity C or Impurity D as measured by HPLC.

In another embodiment, the present invention provides compound of Formula VIb having less than 0.5% as measured by HPLC of one or more of impurities of Formula A, Formula B, Formula C or Formula D:

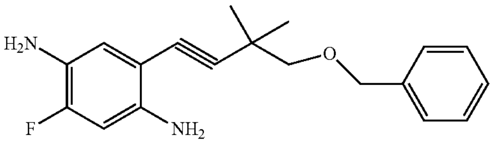

Diamino impurity of Formula A

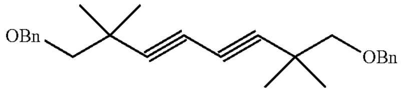

Dimethyl butyne dimer impurity of Formula B

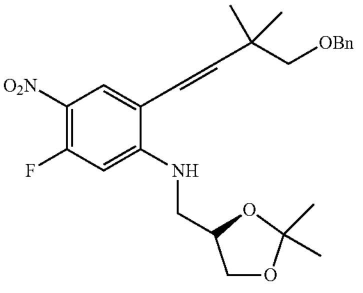

Ene impurity of Formula C

-continued

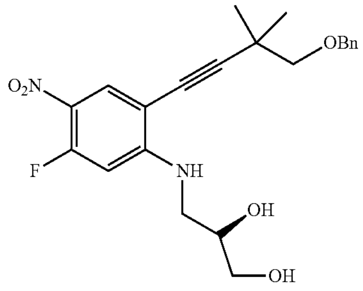

Dioxalane-Diol impurity of Formula D

In another embodiment, the present invention provides a compound of Formula VI:

Formula VI

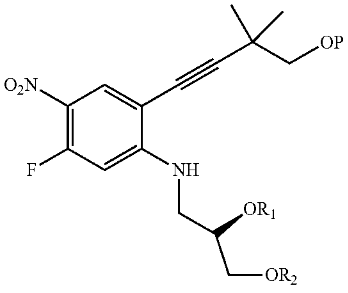

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In a preferred embodiment, the present invention provides a compound of Formula Via.

Formula VIa

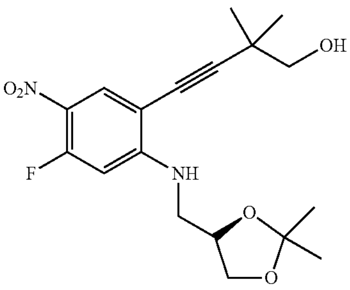

In a preferred embodiment, the present invention provides a compound of formula VIb.

Formula VIb

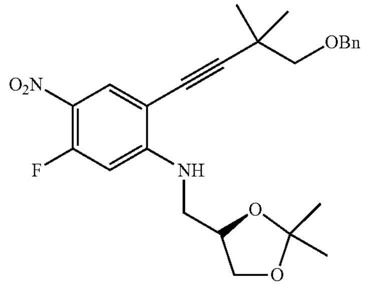

In another embodiment, the present invention provides crystalline compound of Formula VIb.

Figure 2:
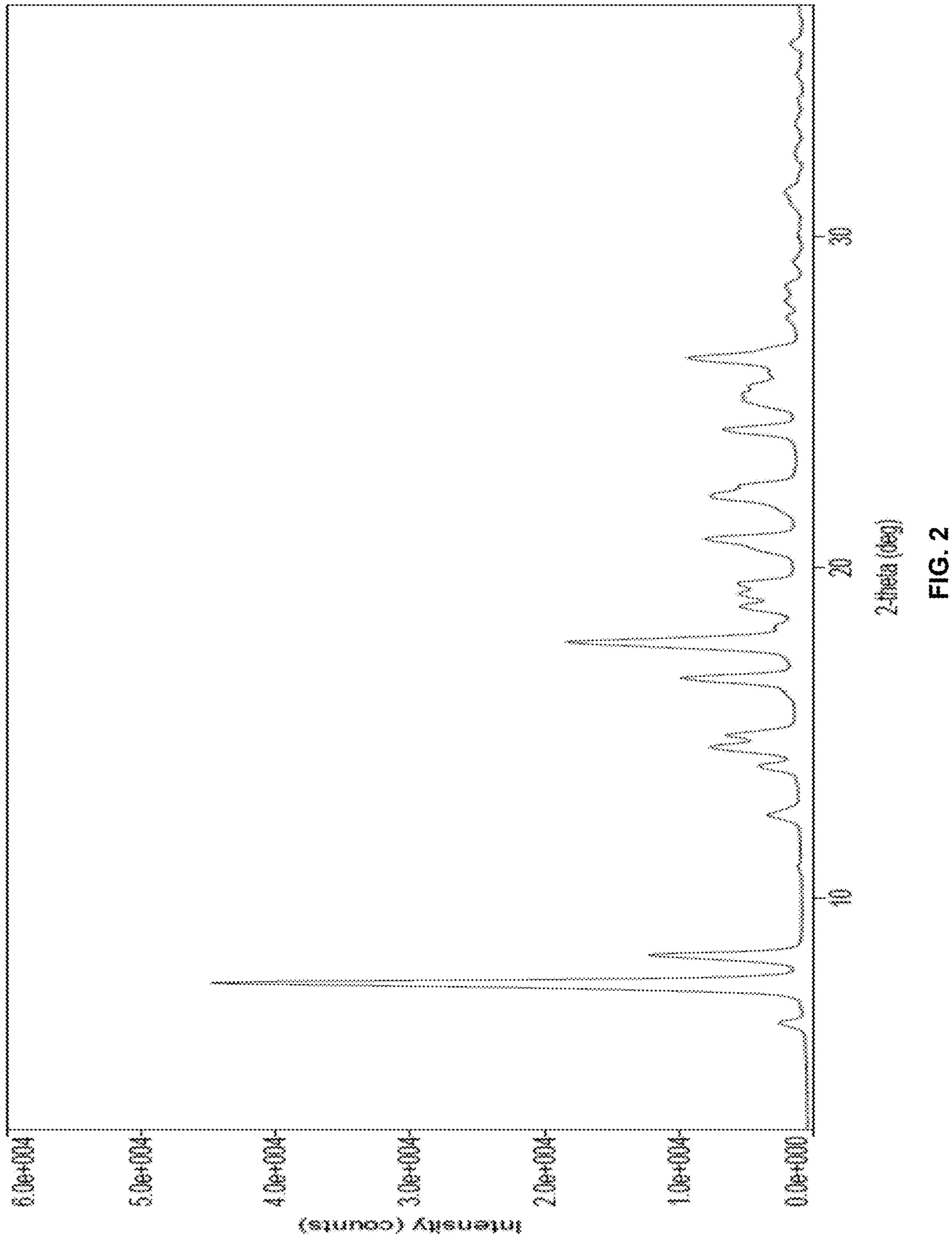
FIG. 2 is the characteristic powder XRD pattern of compound of Formula VIb.

In another embodiment, the present invention provides compound of Formula VIb characterized by X-Ray powder diffraction (PXRD) pattern substantially in accordance with FIG. 2.

In another embodiment, the present invention provides compound of Formula VIb characterized by X-Ray powder diffraction (PXRD) pattern peaks at about 6.3, 7.5, 8.3, 12.5, 14.0, 14.5, 15.0, 16.6, 17.7, 18.8, 19.2, 19.5, 20.6, 20.9, 22.1, 22.5, 24.1, 25.1, 25.7, 26.3, and 38.0±0.2° 2θ.

In another embodiment, the compound of Formula VI, preferably Formula VIa or Formula VIb obtained according to the processes of the invention can be used as an intermediate or as a starting material in the preparation of Tezacaftor of Formula I.

Step c) of the aforementioned process involves cyclization of the compound of Formula VI, wherein the "P" represents hydrogen or a suitable hydroxyl protecting group preferably benzyl and R1 and R2 represents hydrogen or an alcoholic protecting group or both taken together to form a diol protecting group, preferably a diol protecting group, to obtain an indole compound of Formula VII, wherein the "P" represents hydrogen or a suitable hydroxyl protecting group preferably benzyl and R1 and R2 represents hydrogen or an alcoholic protecting group or both taken together to form a diol protecting group, preferably a diol protecting group, followed by reduction with a suitable reducing agent to obtain an amine compound of Formula VIII, wherein the "P" represents hydrogen or a suitable hydroxyl protecting group preferably benzyl and R1 and R2 represents hydrogen or an alcoholic protecting group or both taken together to form a diol protecting group, preferably a diol protecting group or a salt thereof.

The cyclization of compound of formula VI is carried out in presence of a suitable base, a suitable solvent and a suitable catalyst.

The suitable base used herein for cyclization includes, but is not limited to Triethylamine, potassium tertiary butoxide, sodium ethoxide, potassium carbonate, sodium carbonate, cesium carbonate, sodium acetate, potassium acetate and diisopropyl ethyl amine and the like and mixtures thereof; preferably the suitable base is Triethylamine.

The suitable catalysts used herein for cyclization includes, but is not limited to Tetra-n-butylammonium fluoride, bis (dibenzylideneacetone)palladium [Pd(dba)2], tris(dibenzylideneacetone) dipalladium [Pd2(dba)3], palladium(II)acetate [Pd(OAc)2], bis(triphenylphosphine)palladium(II) dichloride [PdCl2($PPh_3)_2$], [1,1'-bis(diphenylphosphino) ferrocene]dichloropalladium(II) [Pd(dppf)$Cl_2$], tetrakis (triphenylphosphine)palladium [Pd(PPh3)4], copper, cuprous bromide, cuprous iodide, 2,2'-bis-diphenylphosphanyl[1,1'] binaphtalenyl (rac-Binap), allylpalladium(II) chloride dimer {[PdCl ($C_3H_5$)]$_2$}, disodium tetrachloropalladate [$Na_2PdCl_4$], palladium(II) chloride [$PdCl_2$], bis(acetonitrile) dichloropalladium(II) [$PdCl_2(MeCN)_2$] and the like and mixtures thereof; preferably the suitable catalyst is bis (acetonitrile)dichloropalladium (II).

The cyclization of compound of Formula VI is carried out in a suitable solvent. The suitable solvent includes but is not limited to ethers, alcohols, aromatic hydrocarbons, amides, sulfoxides, nitriles and mixtures thereof. Preferably ethers include, but are not limited to tetrahydrofuran, 2-methyl tetrahydrofuran, dimethyl ether, methyl tertiary butyl ether and the like; alcohols include, but are not limited to methanol, ethanol, isopropanol and the like; aromatic hydrocarbons include, but are not limited to toluene, xylene and the like; amides include, but are not limited to dimethylformamide, dimethyl acetamide, N-methyl pyrrolidinone and the like; sulfoxides include, but are not limited to dimethylsulfoxide, sulfolane and the like; nitriles include, but are not limited to acetonitrile, propionitrile and the like and mixtures thereof; preferably the suitable solvent is acetonitrile, tetrahydrofuran or dimethylformamide.

The step c) cyclization reaction is carried out at a temperature of about 50° C. to reflux temperature; preferably at about 50° C. to about 100° C.

The resultant compound of Formula VII thus formed can be isolated or further processed without isolating it in to next reaction.

As an embodiment, the compound of formula VII is directly utilized for next reaction without isolation. The process involves the resultant reaction mass containing compound of Formula VII may be treated with water and the aqueous layer extracted with water immiscible organic solvent, wherein the solvent is selected from methylene chloride, ethyl acetate or methyl tert. butyl ether. Thereafter the product containing organic layer may be evaporated under vacuum. The resulting residue may be further dissolved in a suitable solvent and proceed further without isolating the compound of formula VII.

The suitable solvent used herein for dissolution of compound of Formula VII is selected from the group consisting of water, alcohols, ethers, and mixtures thereof. The alcohols include, but are not limited to methanol, ethanol, isopropanol, n-propanol, n-butanol, isobutanol and the like; ethers include, but are not limited to diethyl ether, tetrahydrofuran, dioxane and the like; preferably the suitable solvent is a mixture of methanol and tetrahydrofuran.

In another embodiment, the present invention provides a compound of Formula VII:

Formula VII

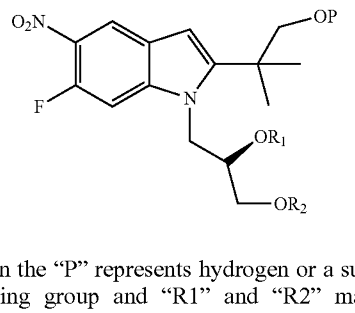

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In a preferred embodiment, the present invention provides a compound of Formula VIIa.

Formula VIIa

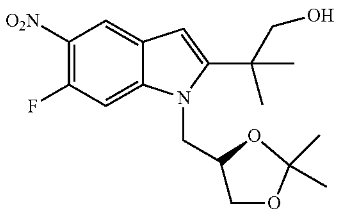

In a preferred embodiment, the present invention provides a compound of formula VIIb.

Formula VIIb

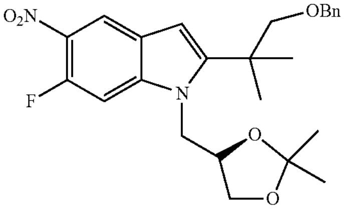

In another embodiment, the compound of Formula VII obtained according to the processes of the invention can be used as an intermediate or as a starting material in the preparation of Tezacaftor of Formula I.

The nitro group of the compound of formula VII is reduced to obtain an amine compound of Formula VIII or a salt thereof.

The reduction of nitro group is carried out by using a suitable reducing agent or by using a suitable catalyst in presence of hydrogen donor and a solvent.

The suitable reducing agent used herein includes but is not limited to sodium borohydride (NaBH4), lithium aluminium hydride (LiAlH4). The suitable catalyst employed herein includes but is not limited to palladium on carbon, $PtO_2$, Raney Nickel, nickel (II) chloride, iridium, ruthenium, rhodium, iron; zinc and the like; and mixtures thereof; and hydrogen source employed herein includes but is not limited to hydrogen gas, hydrazine, silanes, formic acid, sodium formate, ammonium formate, hydrochloric acid, acetic acid and the like and mixtures thereof; preferably the suitable reducing agent is sodium borohydride, sodium borohydride/nickel (II) chloride, palladium on carbon/ammonium formate, Ra Ni/H2 or mixtures thereof.

The reduction of the compound of Formula VII is carried out in a suitable solvent. The suitable solvent includes but is not limited to ethers, alcohols, amides, sulfoxides, water and mixtures thereof. Preferably ethers include, but are not limited to tetrahydrofuran, 2-methyltetrahydrofuran, dimethyl ether, methyl tertiary butyl ether and the like; alcohols include, but are not limited to methanol, ethanol, isopropanol and the like; amides include, but are not limited to dimethylformamide, dimethyl acetamide, N-methyl pyrrolidinone and the like; sulfoxides include, but are not limited to dimethylsulfoxide, sulfolane and the like; water and mixtures thereof; preferably the solvent is tetrahydrofuran or methanol.

The reduction of the compound of Formula VII is carried out at a temperature of about 0° C. to about 80° C.; preferably the reduction reaction was carried out at a temperature of about 20° C. to about 60° C.

The resultant amine compound of Formula VIII thus formed may be isolated or further processed without isolating in to next reaction.

As an embodiment, the reaction mass may be extracted with a water immiscible organic solvent selected from toluene, xylene or methylene chloride or ethyl acetate; separating the unreacted reduction catalyst and other insoluble materials by filtration followed by concentrating the resultant reaction mass. Then, the resultant amine compound of Formula VIII may optionally be isolated by formation an acid salt of compound of Formula VIII as an intermediate.

The present inventors have provided isolation of amine compound of formula VIII by formation of an acid salt of compound of Formula VIII as an intermediate.

In another embodiment, the present invention provides a process for preparation of an acid salt of an amine compound of Formula VIII, wherein the "P" represents hydrogen or a suitable hydroxyl protecting group preferably benzyl and R1 and R2 represents hydrogen or an alcoholic protecting group or both taken together to form a diol protecting group, preferably a diol protecting group, comprising:

a) providing a solution of compound of Formula VIII in one or more organic solvents,
b) adding a suitable acid to the step a) solution, and
c) isolating the compound of Formula VIII as an acid salt.

In another embodiment, the present invention provides a process for isolation of amine compound of Formula VIII, wherein the "P" represents hydrogen or a suitable hydroxyl protecting group preferably benzyl and R1 and R2 represents hydrogen or an alcoholic protecting group or both taken together to form a diol protecting group, preferably a diol protecting group, comprising: formation of an acid salt of compound of Formula VIII as an intermediate, neutralization of the salt, isolating the pure amine compound of Formula VIII and converting it in to Tezacaftor of Formula I.

In another embodiment, the present invention provides a process for isolation of amine compound of Formula VIII, wherein the "P" represents hydrogen or a suitable hydroxyl protecting group preferably benzyl and R1 and R2 represents hydrogen or an alcoholic protecting group or both taken together to form a diol protecting group, preferably a diol protecting group, comprising:

a) providing a solution of compound of Formula VIII in one or more organic solvents,
b) adding a suitable acid to the step a) solution,
c) isolating the compound of Formula VIII as an acid salt,
d) neutralizing the acid salt of compound of Formula VIII with a suitable base, and
e) isolating the amine compound of Formula VIII.

The one or more organic solvents for providing a solution of compound of Formula VIII include, but are not limited to alcohols, ketones, esters, nitriles, ethers, halogenated hydrocarbons, aromatic hydrocarbons and mixtures thereof. The alcohols include, but are not limited to methanol, ethanol, isopropanol, butanol and the like; ketones include, but are not limited to acetone, methyl isobutyl ketone, methyl ethyl ketone and the like; esters include, but are not limited to ethylacetate, isopropyl acetate, butyl acetate and the like; nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform and the like; aromatic hydrocarbons include, but are not limited to toluene, xylene and the like and mixtures thereof, preferably acetonitrile, tetrahydrofuran, 1,4-dioxane, methyl tertiary butyl ether and mixture thereof, more preferably methyl tertiary butyl ether.

The suitable temperature for providing a solution of compound of Formula VIII may be carried out at a temperature of about 25° C. to reflux temperature; preferably at 25° C. to about 45° C.

The acid used herein are selected from the group comprising of organic acid selected form trifluoro acetic acid, hydrochloric acid, methane sulfonic acid, ethane sulfonic acid, benzenesulfonic acid, 4-bromo benzenesulfonic acid, p-toluenesulfonic acid, oxalic acid, tartaric acid, citric acid, fumaric acid, formic acid, dibenzoyl tartaric acid, malic acid, maleic acid, mandelic acid, malonic acid, succinic acid, camphorsulfonic acid and the like; inorganic acid selected from hydrochloric acid, hydrobromic acid, phosphoric acid, sulphuric acid and the like; preferably oxalic acid, tartaric acid, fumaric acid, hydrochloric acid; more preferably oxalic acid.

The compound of Formula VIII as an acid salt can be isolated by any conventional techniques known in the art, for example filtration. If necessary, cooling step may be involved for better precipitation of the product prior to filtration.

The compound of Formula VIII as an acid salt recovered by the purification process described as above is an oxalate salt of compound of Formula VIII. Preferably the oxalate salt of compound of Formula VIII is isolated as a crystalline form.

The step of neutralizing the acid salt of compound of Formula VIII involves treating the resultant acid salt of compound of Formula VIII with a suitable base such as sodium bicarbonate, potassium bicarbonate, sodium hydroxide, potassium hydroxide, ammonium hydroxide and the like and mixture thereof; preferably base is sodium bicarbonate.

The neutralization step may be carried out in a suitable organic solvent at a temperature of about 0° C. to about 50° C. The suitable organic solvent includes, but is not limited to alcohols, ketones, nitriles, ethers, halogenated hydrocarbons and mixtures thereof. The alcohols include, but are not limited to methanol, ethanol, isopropanol and the like; ketones include, but are not limited to acetone, methyl isobutyl ketone, methyl ethyl ketone and the like; nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform and the like and mixture thereof; preferably methanol, 1,4-dioxane or methylene chloride and mixture thereof; more preferably methylene chloride.

Then, the resultant pure amine compound of Formula VIII may be isolated from the reaction mass by methods known in the art, for instance, the product containing organic layer may be separated followed by concentrating the organic layer under vacuum.

The pure amine compound of Formula VIII obtained by the process described above can be used as an intermediate in the preparation of Tezacaftor.

The process of conversion of amine compound of Formula VIII in to Tezacaftor of Formula I can be carried out according to the present invention described herein below.

In another embodiment, the present invention provides an amine compound of Formula VIII or a salt thereof.

Formula VIII

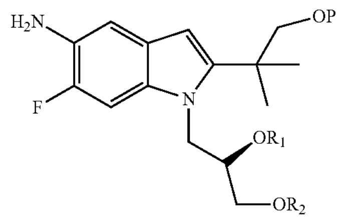

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In another embodiment, the present invention provides a compound of Formula VIIIa or a salt thereof.

Formula VIIIa

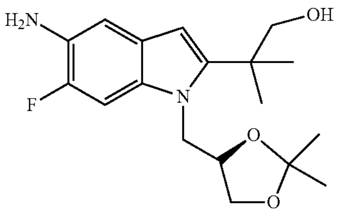

In another embodiment, the present invention provides a compound of formula VIIIb or a salt thereof.

Formula VIIIb

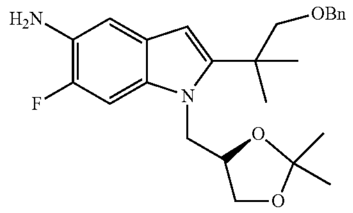

In accordance with another embodiment, the present invention provides an acid salt of an amine compound of Formula VIIIb.

In accordance with another embodiment, the present invention provides oxalic acid salt of an amine compound of Formula VIIIb.

Figure 3:
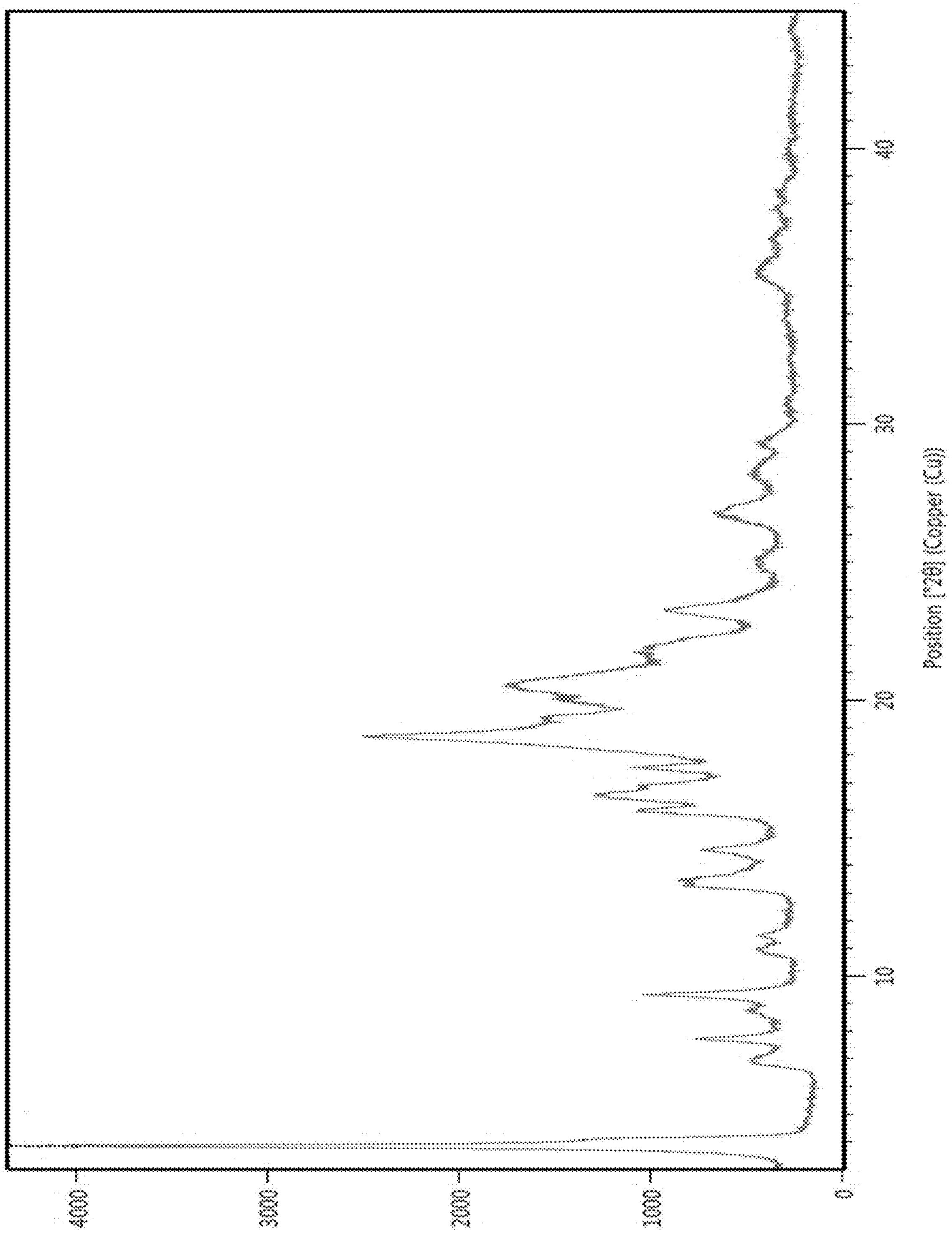
FIG. 3 is the characteristic powder XRD pattern of compound of Formula VIIIb.

In accordance with another embodiment, the present invention provides oxalic acid salt of an amine compound of Formula VIIIb characterized by an X-ray powder diffraction pattern substantially in accordance with FIG. 3.

In another embodiment, the present invention provides oxalic acid salt of an amine compound of Formula VIIIb characterized by X-ray powder diffraction pattern peaks at about 3.9, 6.8, 7.7, 8.7, 9.3, 10.9, 11.5, 13.2, 13.5, 14.5, 16.0, 16.4, 16.6, 17, 17.5, 18.6, 19.4, 20.0, 22.0, 22.2, 23.2, 25.0, 26.7, 28.1 and 29.2±0.2° 2θ.

In another embodiment, the present invention provides an acid salt of an amine compound of Formula VIII, wherein the "P" represents hydrogen or a suitable hydroxyl protecting group preferably benzyl and R1 and R2 represents hydrogen or an alcoholic protecting group or both taken together to form a diol protecting group, preferably a diol protecting group.

In an another embodiment, the amine compound of formula VIII is also prepared by first reduction of compound of Formula VI with a suitable reducing agent to obtain a compound of Formula VII' followed by cyclization to obtain an amine compound of Formula VIII, wherein the "P" represents hydrogen or a suitable hydroxyl protecting group preferably benzyl and R1 and R2 represents hydrogen or an alcoholic protecting group or both taken together to form a diol protecting group, preferably a diol protecting group.

The first step of the process involves nitro group of the compound of formula VI is reduced to obtain an amine compound of Formula VII' or a salt thereof.

The reduction of nitro group of the compound of Formula VI is carried out by using a suitable reducing agent or by using a suitable catalyst in presence of hydrogen donor and a solvent.

The suitable reducing agent used herein includes but is not limited to sodium borohydride (NaBH4), lithium aluminium hydride (LiAlH4). The suitable catalyst employed herein includes but is not limited to palladium on carbon, $PtO_2$, Raney Nickel, nickel (II) chloride, iridium, ruthenium, rhodium, iron; zinc and the like; and mixtures thereof; and hydrogen donor employed herein includes but is not limited to hydrogen gas, hydrazine, silanes, formic acid, sodium formate, ammonium formate, hydrochloric acid, acetic acid and the like and mixtures thereof; preferably the suitable reducing agent is sodium borohydride, sodium borohydride/nickel (II) chloride, palladium on carbon/ammonium formate, Ra Ni/H2 or mixtures thereof.

The reduction of the compound of Formula VI is carried out in a suitable solvent. The suitable solvent includes but is not limited to ethers, alcohols, amides, sulfoxides, water and mixtures thereof. Preferably ethers include, but are not limited to tetrahydrofuran, 2-methyltetrahydrofuran, dimethyl ether, methyl tertiary butyl ether and the like; alcohols include, but are not limited to methanol, ethanol, isopropanol and the like; amides include, but are not limited to dimethylformamide, dimethyl acetamide, N-methyl pyrrolidinone and the like; sulfoxides include, but are not limited to dimethylsulfoxide, sulfolane and the like; water and mixtures thereof; preferably the solvent is tetrahydrofuran or methanol.

The reduction of the compound of Formula VI is carried out at a temperature of about 0° C. to about 80° C.; preferably the reduction reaction was carried out at a temperature of about 20° C. to about 60° C.

In another embodiment, the present invention provides a compound of Formula VII':

Formula VII'

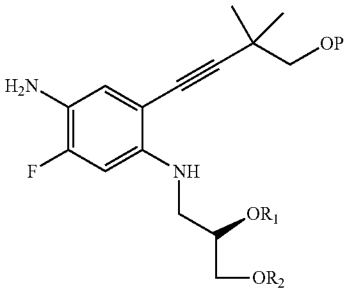

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In another embodiment, the present invention provides a compound of Formula VII'a.

Formula VII'a

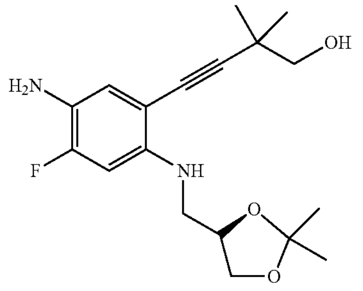

In another embodiment, the present invention provides a compound of formula VII'b.

Formula VII'b

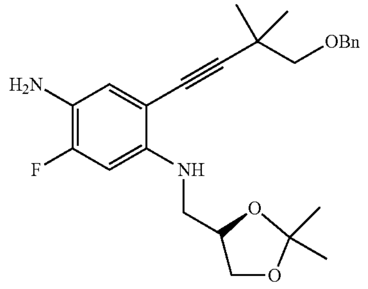

The cyclization of compound of formula VII' is carried out in presence of a suitable base, a suitable solvent and a suitable catalyst at a temperature of about 50° C. to reflux temperature.

The suitable base used herein for cyclization of compound of formula VII' includes, but is not limited to Tetra-n-butylammonium fluoride, Triethylamine, potassium tertiary butoxide, sodium ethoxide, potassium carbonate, sodium carbonate, cesium carbonate, sodium acetate, potassium acetate and diisopropyl ethyl amine and the like and mixtures thereof; preferably the suitable base is Tetra-n-butylammonium fluoride or Triethylamine.

The suitable catalysts used herein for cyclization of compound of formula VII' includes, but is not limited to bis(dibenzylideneacetone)palladium [Pd(dba)2], tris(dibenzylideneacetone) dipalladium [Pd2(dba)3], palladium(II)acetate [Pd(OAc)2], bis(triphenylphosphine)palladium(II) dichloride [PdCl2$(PPh_3)_2$], [1,1'-bis(diphenylphosphino) ferrocene]dichloropalladium(II) [Pd(dppf)$Cl_2$], tetrakis (triphenylphosphine)palladium [Pd(PPh3)4], copper, cuprous bromide, cuprous iodide, 2,2'-bis-diphenylphosphanyl[1,1'] binaphtalenyl (rac-Binap), allylpalladium(II) chloride dimer {[PdCl $(C_3H_5)]_2$}, disodium tetrachloropalladate [$Na_2PdCl_4$], palladium(II) chloride [$PdCl_2$], bis(acetonitrile) dichloropalladium(II) [$PdCl_2(MeCN)_2$] and the like and mixtures thereof; preferably the suitable catalyst is bis (acetonitrile)dichloropalladium (II).

The cyclization of compound of Formula VII' is carried out in a suitable solvent. The suitable solvent includes but is not limited to ethers, alcohols, aromatic hydrocarbons, amides, sulfoxides, nitriles and mixtures thereof. Preferably ethers include, but are not limited to tetrahydrofuran, 2-methyl tetrahydrofuran, dimethyl ether, methyl tertiary butyl ether and the like; alcohols include, but are not limited to methanol, ethanol, isopropanol and the like; aromatic hydrocarbons include, but are not limited to toluene, xylene and the like; amides include, but are not limited to dimethylformamide, dimethyl acetamide, N-methyl pyrrolidinone and the like; sulfoxides include, but are not limited to dimethylsulfoxide, sulfolane and the like; nitriles include, but are not limited to acetonitrile, propionitrile and the like and mixtures thereof; preferably the suitable solvent is acetonitrile, tetrahydrofuran or dimethylformamide.

In another embodiment, the amine compound of Formula VIII obtained according to the processes of the invention can be used as an intermediate or as a starting material in the preparation of Tezacaftor of Formula I.

In another embodiment, the present invention provides a process for preparation of a compound of Formula VI, comprising:

a) treating a compound of Formula II with a compound of Formula V to obtain a compound of Formula XIII, Formula II

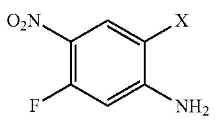

Formula V

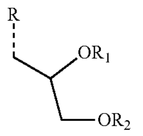

Formula XIII

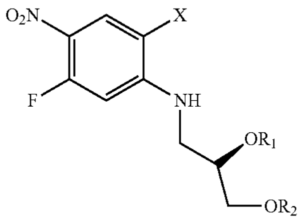

wherein "X" represents a suitable leaving group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group; and b) reacting the compound of Formula XIII with an alkyne of Formula III to obtain a compound of Formula VI, wherein "P" represents hydrogen or a suitable hydroxyl protecting group and "R1" and "R2" are defined as above.

Formula III

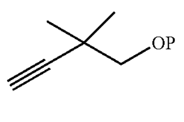

The reaction of the compound of Formula II, wherein "X" represents a suitable leaving group, preferably bromine with a compound of formula V, preferably a compound of Formula Va, Vb or Vc described just as above, to obtain compound of formula XIII.

The reaction of compound of Formula II with compound of Formula V may be carried out in presence of an acid, a reducing agent and a solvent is carried out at a temperature of about −25° C. to about 10° C.

The acid used herein includes, but is not limited to formic acid, acetic acid, trichloroacetic acid, trifluoroacetic acid, 2,2,2-triflouroethanol, tin chloride, thiourea, titanium isopropoxide, indium chloride, indium bromide, boric acid, p-toluenesulfonic acid monohydrate, benzoic acid and the like and mixtures thereof; preferably the acid is trifluoroacetic acid.

The reducing agent used herein includes, but is not limited to silanes such as triethylsilane, tri-iso-propylsilane, polymethylhydrosiloxane, phenylsilane, diphenyl silane, triphenyl silane; metal catalysts such as nickel, copper, iron, cobalt, ruthenium, rhodium, palladium, osmium, iridium and platinum or mixtures thereof in presence of hydrogen gas or hydrogen donor such as formic acid; borohydride reagents such as sodium borohydride ($NaBH_4$), sodium cyanoborohydride ($NaCNBH_3$), sodium triacetoxyborohydride ($NaBH(OAc)_3$); 2-picolineborane; α-picoline-borane; decaborane, boric acid and the like and mixtures thereof; preferably the reducing agent is sodium triacetoxyborohydride.

The solvent used herein includes, but is not limited to hydrocarbons such as toluene, xylene, chlorobenzene, heptane, hexane and the like; haloalkanes such as methylene chloride, chloroform, ethylene dichloride, and the like; esters such as methyl acetate, ethyl acetate, n-propyl acetate, isopropyl acetate, tert-butyl acetate and the like; ethers such as dimethyl ether, diethyl ether, diisopropyl ether, tert-butyl methyl ether, tetrahydrofuran, dioxane and the like and mixtures thereof; preferably the solvent is methylene chloride.

The resultant compound of Formula XIII thus formed can be isolated or further processed without isolating in to next reaction by reacting with an alkyne compound of Formula II to obtain compound of Formula VI.

In another embodiment, the present invention provides a compound of Formula XIII:

Formula XIII

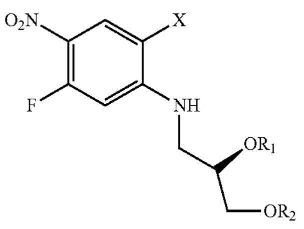

wherein the "X" represents a suitable leaving group and "R1" and "R2" may be same or different and represents a hydrogen or an alcoholic protecting group or "R1" and "R2" are taken together to form a diol protecting group.

In a preferred embodiment, the present invention provides a compound of Formula XIIIa:

Formula XIIIa

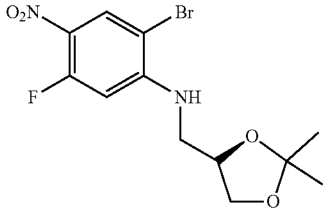

In another embodiment, the compound of Formula XIII obtained according to the processes of the invention can be used as an intermediate or as a starting material in the preparation of Tezacaftor of Formula I.

The step b) reaction of the compound of Formula XIII with the alkyne compound of Formula III may be carried out in presence of a suitable catalyst, a suitable ligand, a suitable base and a suitable solvent.

The suitable catalyst, suitable ligand, suitable base and a suitable solvent used for reaction of compound of Formula XIII with the alkyne compound of Formula III and reaction procedures are same as to those described just as above for the reaction of compound of Formula II with the alkyne compound of Formula III.

The obtained compound of Formula VI can be converted in to Tezacaftor of Formula I according to the procedures described just as above.

In another embodiment, the present invention provides a process for preparation of an indole compound of Formula VII, comprising:

a) cyclizing a compound of Formula IV to obtain a compound of Formula XII,

Formula XII

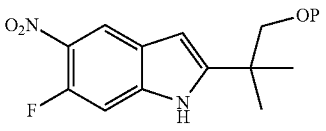

wherein "P" represents hydrogen or a suitable hydroxyl protecting group; and b) treating the compound of Formula XII with a compound of Formula V to obtain an indole compound of formula VII, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

The compound of Formula IV, wherein the "P" represents hydrogen or a suitable hydroxyl protecting group preferably benzyl, used herein can be prepared as per the process described as above embodiments. The cyclization of the compound of Formula IV may be carried out in presence of a suitable base, a suitable catalyst and a suitable solvent.

The suitable base used herein for cyclization of compound of Formula IV includes, but is not limited to Triethylamine, potassium tertiary butoxide, sodium ethoxide, potassium carbonate, sodium carbonate, cesium carbonate, sodium acetate, potassium acetate and diisopropyl ethyl amine and the like and mixtures thereof; preferably the suitable base is or Triethylamine.

The suitable catalysts used herein for the cyclization of compound of Formula IV includes, but is not limited to Tetra-n-butylammonium fluoride, bis(dibenzylideneacetone)palladium [Pd(dba)2], tris(dibenzylideneacetone) dipalladium [Pd2(dba)3], palladium(II)acetate [Pd(OAc)2], bis(triphenylphosphine)palladium(II) dichloride [PdCl2 $(PPh_3)_2$], [1,1'-bis(diphenylphosphino) ferrocene]dichloropalladium(II) [Pd(dppf)$Cl_2$], tetrakis (triphenylphosphine) palladium [Pd(PPh3)4], copper, cuprous bromide, cuprous iodide, 2,2'-bis-diphenylphosphanyl[1,1'] binaphtalenyl (rac-Binap), allylpalladium(II) chloride dimer {[PdCl $(C_3H_5)]_2$}, disodium tetrachloropalladate [$Na_2PdCl_4$], palladium(II) chloride [$PdCl_2$], bis(acetonitrile)dichloropalladium(II) [$PdCl_2(MeCN)_2$] and the like and mixtures thereof; preferably the suitable catalyst is Tetra-n-butylammonium fluoride or bis(acetonitrile)dichloropalladium (II).

The suitable solvent used herein for the cyclization of compound of Formula IV is selected from the group consisting of alcohols include, but are not limited to methanol, ethanol, isopropanol and the like; ethers include, but are not limited to tetrahydrofuran, 2-methyl tetrahydrofuran, dimethyl ether, methyl tertiary butyl ether and the like; aromatic hydrocarbons include, but are not limited to toluene, xylene and the like; amides include, but are not limited to dimethylformamide, dimethyl acetamide, N-methyl pyrrolidinone and the like; sulfoxides include, but are not limited to dimethylsulfoxide, sulfolane and the like; nitriles include, but are not limited to acetonitrile, propionitrile and the like and mixtures thereof; preferably the suitable solvent is acetonitrile, tetrahydrofuran or dimethylformamide.

The cyclization reaction is carried out at a temperature of about 50° C. to reflux; preferably at about 50° C. to about 100° C.

The compound of Formula XII thus formed can be isolated or further processed without isolating in to next reaction by reacting with the compound of V to obtain an indole compound of formula VII.

In another embodiment, the present invention provides a compound of Formula XII:

Formula XII

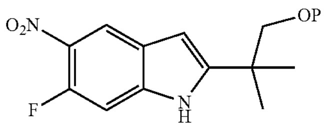

wherein the "P" represents hydrogen or a suitable hydroxyl protecting group.

In a preferred embodiment, the present invention provides a compound of Formula XIIa.

Formula XIIa

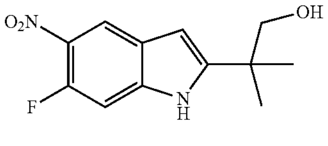

In a preferred embodiment, the present invention provides a compound of Formula XIIb.

Formula XIIb

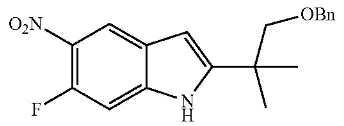

In another embodiment, the compound of Formula XII obtained according to the processes of the invention can be used as an intermediate or as a starting material in the preparation of Tezacaftor of Formula I.

The step b) of the aforementioned process involves reaction of the compound of Formula XII with a compound of Formula V to obtain an indole compound of formula VII in presence of a suitable base and a suitable solvent. Wherein the compound of formula V is any of the compounds of Formula Va, Formula Vb or Formula Vc described just as above.

The suitable base used herein for reaction of compound of Formula XII with a compound of Formula V includes, but is not limited to sodium hydroxide, potassium hydroxide, ammonium hydroxide, sodium methoxide, sodium ethoxide, sodium carbonate, potassium carbonate, cesium carbonate, sodium bicarbonate, potassium bicarbonate and the like and mixtures thereof; preferably the suitable base is cesium carbonate.

The suitable solvent used herein for reaction of compound of Formula XII with a compound of Formula V is selected from the group consisting of alcohols include, but are not limited to methanol, ethanol, isopropanol and the like; ketones include, but are not limited to acetone, methyl-isobutylketone, methylethylketone; amides include, but are not limited to dimethyl formamide, dimethyl acetamide, N-methyl pyrrolidinone; sulfoxides include, but are not limited to dimethyl sulfoxide, diethyl sulfoxide; ethers include, but are not limited to tetrahydrofuran, dimethyl ether, diethyl ether, diisopropyl ether, methyl tertiary butyl ether, 1,4-dioxane and mixtures thereof; preferably the suitable solvent is dimethyl formamide or dimethyl sulfoxide.

The step b) reaction is carried out at a temperature of about 50° C. to reflux; preferably at about 50° C. to about 100° C. The obtained compound of Formula VII can be isolated and converted in to Tezacaftor of Formula I according to the procedures described just as above.

In another embodiment, the present invention provides a process for preparation of a compound of Formula VII' or a salt thereof, comprising:

a) reacting a compound of Formula II' with an alkyne of Formula III to obtain a compound of Formula IV', Formula II'

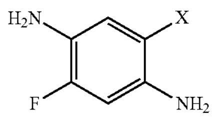

Formula IV'

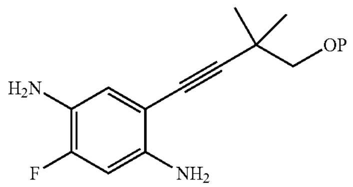

wherein "X" represents a suitable leaving group and "P" represents hydrogen or a suitable hydroxyl protecting group; and b) treating the compound of Formula IV' with a compound of Formula V to obtain a compound of formula VII' or a salt thereof, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

Preferably the compound of Formula II' and Formula IV' wherein the "P" represents hydrogen or a suitable hydroxyl protecting group preferably benzyl and compound of Formula V wherein the R1 and R2 represents hydrogen or an alcoholic protecting group or both taken together to form a diol protecting group, preferably a diol protecting group and the compound of Formula V may be any of Formula Va, Vb or Vc.

The reaction procedures for the reaction of a compound of formula II' with a compound Formula III and for the reaction of a compound of Formula IV' with a compound of formula V are same as to those described as above embodiments for the reaction of a compound of formula II with a compound Formula III and for the reaction of a compound of Formula IV with a compound of formula V respectively.

In another embodiment, the present invention provides a compound of Formula IV':

Formula IV'

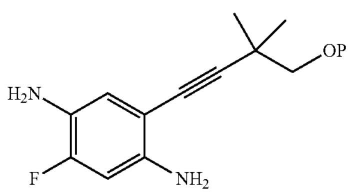

wherein the "P" represents hydrogen or a suitable hydroxyl protecting group.

In a preferred embodiment, the present invention provides a compound of Formula IV'a:

Formula IV'a

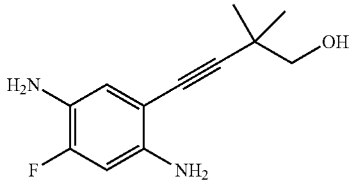

In a preferred embodiment, the present invention provides a compound of formula IV'b:

Formula IV'b

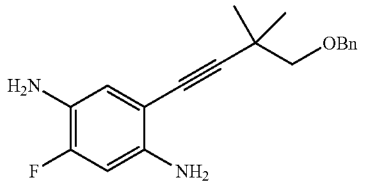

In another embodiment, the obtained compound of Formula VII' from compound of Formula IV' can be isolated and converted in to Tezacaftor of Formula I according to the procedures described just as above.

In another embodiment, the present invention provides a process for preparation of a compound of Formula VII' or a salt thereof, comprising:

a) reacting a compound of Formula II' with a compound of Formula V to obtain a compound of Formula XIII', Formula XIII'

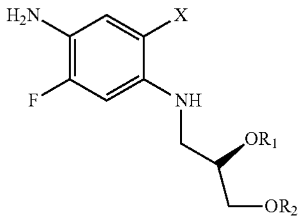

wherein "X" represents a suitable leaving group, "R" represents an oxygen atom or a suitable leaving group and dotted line represents a single bond or a double bond and "R1" and "R2" may be same or different and represents a hydrogen or an alcoholic protecting group or "R1" and "R2" are taken together to form a diol protecting group; and b) treating the compound of formula XIII' with an alkyne of Formula III to obtain a compound of formula VII' or a salt thereof, wherein "P" represents hydrogen or a suitable hydroxyl protecting group and "R1" and "R2" are defined as above.

Preferably the compound of Formula II' and Formula V wherein the "X" represents a suitable leaving group preferably halogen selected from fluorine, chlorine, bromine or iodine, more preferably bromine and compound of Formula V wherein the R1 and R2 represents hydrogen or an alcoholic protecting group or both taken together to form a diol protecting group, preferably a diol protecting group and the compound of Formula V may be any of Formula Va, Vb or Vc.

The reaction procedures for the reaction of a compound of formula II' with a compound Formula V and for the reaction of a compound of Formula XIII' with an alkyne of Formula III are same as to those described as above embodiments for the reaction of a compound of formula II with a compound Formula V and for the reaction of a compound of Formula XIII with an alkyne of Formula III respectively.

In another embodiment, the present invention provides a compound of Formula XIII':

Formula XIII'

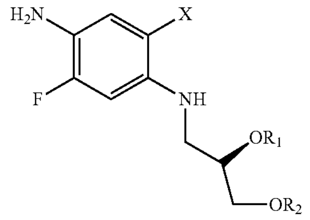

wherein the "X" represents a suitable leaving group and "R1" and "R2" may be same or different and represents a hydrogen or an alcoholic protecting group or "R1" and "R2" are taken together to form a diol protecting group.

In a preferred embodiment, the present invention provides a compound of Formula XIII'a:

Formula XIII'a

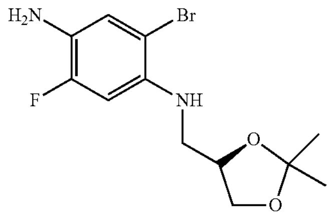

In another embodiment, the compound of Formula VII' or a salt thereof obtained from compound of Formula XIII' according to the processes of the invention can be used as an intermediate or as a starting material in the preparation of Tezacaftor of Formula I.

In another embodiment, the present invention provides a process for preparation of a compound of Formula VIII or a salt thereof, comprising:

a) cyclizing a compound of Formula IV' to obtain an indole compound of Formula XV or a salt thereof, Formula XV

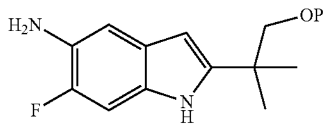

wherein "P" represents hydrogen or a suitable hydroxyl protecting group; and b) treating the compound of Formula XV with a compound of Formula V to obtain a compound of Formula VIII or a salt thereof, wherein "R" represents an oxygen atom or a suitable leaving group and dotted line represents a single bond or a double bond, "R1" and "R2" may be same or different and represents a hydrogen or an alcoholic protecting group or "R1" and "R2" are taken together to form a diol protecting group and "P" is defined as above.

Preferably the compound of Formula IV' wherein the "P" represents hydrogen or a suitable hydroxyl protecting group preferably benzyl and compound of Formula V wherein the R1 and R2 represents hydrogen or an alcoholic protecting group or both taken together to form a diol protecting group, preferably a diol protecting group and the compound of Formula V may be any of Formula Va, Vb or Vc.

The cyclization procedure of a compound of Formula IV' and reaction procedure of compound of Formula XV with a compound Formula V are same as to those described as above embodiment for the cyclization procedure of a compound of Formula IV and for the reaction procedure of compound of Formula XII with a compound Formula V respectively.

In another embodiment, the present invention provides a compound of Formula XV:

Formula XV

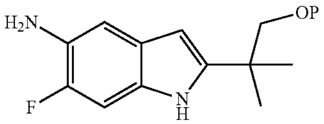

wherein the "P" represents hydrogen or a suitable hydroxyl protecting group.

In a preferred embodiment, the present invention provides a compound of Formula XVa.

Formula XVa

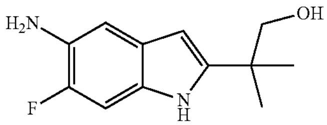

In a preferred embodiment, the present invention provides a compound of Formula XVb.

Formula XVb

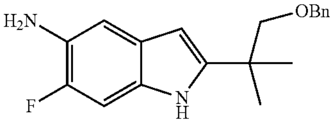

In another embodiment, the compound of Formula VIII or a salt thereof obtained from compound of Formula XV according to the processes of the invention can be used as an intermediate or as a starting material in the preparation of Tezacaftor of Formula I.

In another embodiment, the present invention provides a process for preparation of Tezacaftor of Formula I;

Formula I

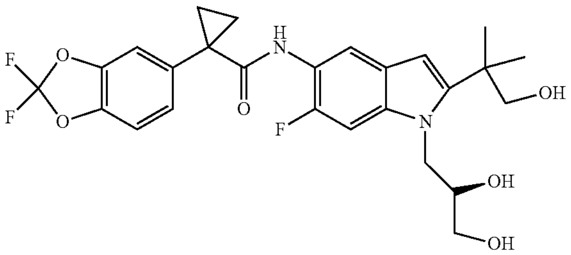

comprising:

a) coupling an amine compound of formula VIII or a salt thereof with an acid compound of Formula IX or its reactive derivative thereof to obtain a compound of Formula X, Formula VIII

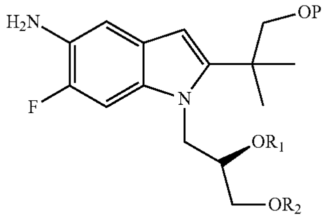

Formula IX

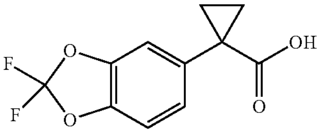

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

Formula X

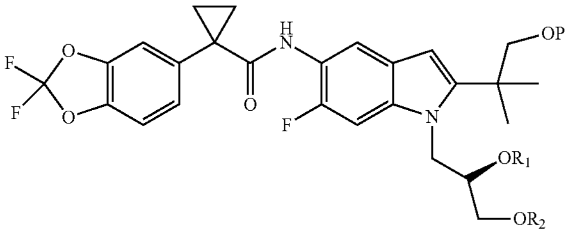

wherein "P" represents hydrogen or a suitable hydroxyl protecting group and "R1" and "R2" may be same or different and represents a hydrogen or an alcoholic protecting group or "R1" and "R2" are taken together to form a diol protecting group; and a) optionally deprotecting the compound of Formula X with a suitable deprotecting agent to obtain Tezacaftor of Formula I.

The amine compound of Formula VIII used herein the process is obtained from processes as described above embodiments and compound of Formula IX used herein is known from U.S. Pat. No. 9,035,072.

Step a) of the aforementioned process involves coupling of an amine compound of formula VIII or a salt thereof with an acid compound of Formula IX or its reactive derivative thereof to obtain a compound of Formula X.

The acid group of compound of Formula IX is first activated with an activating agent in presence of a suitable solvent to obtain activated derivative of compound of Formula IX.

The suitable solvent used herein includes, but is not limited to methylene chloride, chloroform, ethylene dichloride, methyl acetate, ethyl acetate, n-propyl acetate, isopropyl acetate, tert-butyl acetate, acetonitrile; dimethyl formamide; dimethyl sulfoxide; dimethyl acetamide, methyl acetate, ethyl acetate, n-propyl acetate, isopropyl acetate, tert-butyl acetate, water and the like and mixtures thereof; preferably the suitable solvent is a mixture of methylene chloride and dimethyl formamide.

An activated derivative of acid chloride compound is formed by treating the acid compound of Formula IX with chlorinating agent includes, but is not limited to thionyl chloride, oxalyl chloride or an activated derivative of ester compound is generated by contacting the acid compound of formula (IX) with an acid activating agent optionally in the presence of coupling additive.

The acid activating agent used herein is selected from the group consisting of carbonyldiimidazole (CDI), propylphosphonic anhydride (T3P), carbodiimides includes, but is not limited to N,N'-dicyclohexylcarbodiimide (DCC) or diisopropylcarbodiimide (DIPC), 1-ethyl-3-(3-dimethylaminopropyl)-carbodiimide (EDC) and the like; 1-hydroxybenzotriazole based or 1-hydroxy-7-azabenzotriazole based phosphonium salts includes, but is not limited to benzotriazol-1-yl-N-oxy-tris(dimethylamino)phosphonium hexafluoro phosphate (BOP), benzotriazol-1-yl-N-oxy-tris (pyrrolidino)phosphonium hexafluoro phosphate (PyBOP), 7-azabenzotriazol-1-yl-N-oxy-tris(pyrrolidino) phosphonium hexafluorophosphate (PyAOP) and the like; 1-hydroxybenzotriazole based or 1-hydroxy-7-azabenzotriazole based uronium salts includes, but is not limited to N-[(1H-benzotriazol-1-yl)(dimethylamino)methylene]-N-methyl-methan-aminium hexafluorophosphate N-oxide (HBTU), N-[(1H-benzotriazol-1-yl)(dimethylamino)methylene]-N-methylmethanaminium tetrafluoroborate N-oxide (TBTU), N-[(1H-6-chlorobenzotriazol-1-yl)(dimethylamino)-methylene]-N-methylmethanaminium hexafluorophosphate N-oxide (HCTU), N-[(1H-6-chlorobenzotriazol-1-yl)(dimethylamino)methylene]-N-methylmethanaminium tetrafluoroborate N-oxide (TCTU), N-[(dimethylamino)-1H-1,2,3-triazolo[4,5-b]pyridino-aylmethylene]-N-methylmethanaminium hexafluorophosphate (HATU) and the like; halouronium salts includes, but is not limited to bis(tetra-methylene)fluoroformamidinium hexafluorophosphate (BTFFH), 2-chloro-1,3-dimethylimidazolidium hexafluorophosphate and the like; halophosphonium salts includes, but is not limited to bromotris(dimethylamino) phosphonium hexafluorophosphate (BroP), bromotripyrrolidino phosphonium hexafluorophosphate (PyBroP), chlorotripyrrolidino phosphonium hexafluorophosphate (PyCloP) and the like; benzotriazine based uronium and phosphonium salts includes, but is not limited to (3,4-dihydro-4-oxo-1,2,3-benzotriazine-3-yl)-N,N,N',N'-tetramethyluronium tetrafluoroborate (TDBTU), 3-(diethyloxyphosphoryloxy)-1,2,3-benzotriazin-4(3H)-one (DEPBT) and the like and the coupling additive is selected from the group consisting of 1-hydroxybenzotriazole (HOBt), 1-hydroxy-7-azabenzotriazole (HOAt), 3,4-dihydro-3-hydroxy-4-oxo-1,2,3-benzotriazine (DHOBt) and the like and mixtures thereof; preferably the acid compound of Formula IX is activated by treating with chlorinating agent; more preferably the acid compound of Formula IX is activated by treating with thionyl chloride or by oxalyl chloride.

The activation of compound of Formula IX is carried out at a temperature of about −20° C. to reflux; preferably at about 20° C. to about 60° C.

The resulting activated compound of Formula IX is later coupled with the amine compound of formula VIII or a salt thereof to obtain a compound of Formula X.

The coupling reaction is carried out in presence of a base and a suitable solvent.

The base used herein includes, but is not limited to triethylamine (TEA), diisopropylethylamine (DIPEA), N-methylmorpholine, 4-dimethylaminopyridine, pyridine; 2,6-lutidine, 1,4-diazabicyclo[2.2.2]octane (DABCO), trimethylamine, 1,8-Diazabicyclo[5.4.0]undec-7-ene (DBU), 2,6-Di-tert-butyl-4-methylpyridine, di-tert butyl pyridine, 4-dimethylaminopyridine and the like; preferably the base is trimethylamine or diisopropylethylamine.

The suitable solvent used herein includes, but is not limited to haloalkanes such as methylene chloride, chloroform, ethylene dichloride, and the like; esters such as methyl acetate, ethyl acetate, n-propyl acetate, isopropyl acetate, tert-butyl acetate and the like; hydrocarbons such as toluene, xylene, chlorobenzene, heptane, hexane and the like; alcohols such as methanol, ethanol, 1-propanol, 2-propanol, 1-butanol, 2-butanol, 1-pentanol, 1-octanol and the like; acetonitrile; dimethyl formamide; dimethyl sulfoxide; dimethyl acetamide; water; and the like and mixtures thereof, preferably the suitable solvent is methylene chloride.

The coupling reaction is carried out at a temperature of about −20° C. to reflux; preferably at about 20° C. to about 60° C.

The resultant compound of Formula X thus formed can be isolated or further processed without isolating in to next reaction.

The compound of Formula X; preferably the compound of Formula Xb thus obtained by the process of the present invention may contain des fluoro impurity of Formula E which is present in the range of about 0.2% to about 2% by HPLC and the impurity represented as follows:

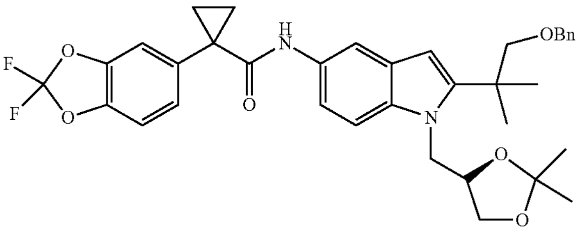

Des fluoro impurity of Formula E

In another embodiment, the present invention provides a process for purification of a compound of Formula X using a suitable solvent system.

In another embodiment, the present invention provides a process for purification of a compound of Formula X, comprising:

c) treating a compound of Formula X with one or more organic solvents, and d) isolating the pure compound of Formula X.

The purification may be carried out by treating the compound of Formula X in one or more organic solvents to obtain a solution at a temperature of about 25° C. to about 35° C., Then, the resultant reaction solution may optionally be cooled to less than room temperature for product precipitation followed by isolating the pure compound of Formula X by techniques known in the art, for example, filtration.

The one or more organic solvents used herein for purification include, but is not limited to alcohols, nitriles, ethers, halogenated hydrocarbons, aromatic hydrocarbons and the like and mixture thereof. The alcohols include, but are not limited to methanol, ethanol, isopropanol, n-propanol, t-butanol and the like; nitriles include, but are not limited to acetonitrile, propionitrile, benzonitrile and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform and the like; aromatic hydrocarbons include, but are not limited to toluene, xylene and the like and mixtures thereof; preferably the one or more organic solvent is Methanol.

The compound of Formula X; preferably the compound of Formula Xb thus obtained according to purification process of the invention having less than 0.1% of compound of Formula E as impurity as measured by HPLC.

In another embodiment, the present invention provides a compound of Formula X:

Formula X

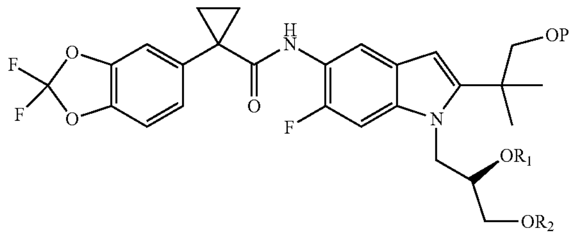

wherein the "P" represents hydrogen or a suitable hydroxyl protecting group and "R1" and "R2" may be same or different and represents a hydrogen or an alcoholic protecting group or "R1" and "R2" are taken together to form a diol protecting group.

In another embodiment, the present invention provides a compound Formula Xa.

Formula Xa

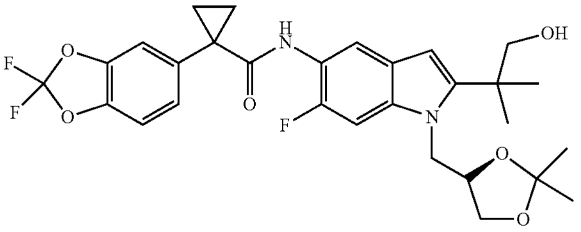

In another embodiment, the present invention provides a compound of Formula Xb.

Formula Xb

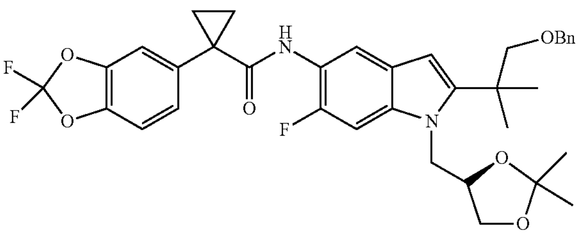

In another embodiment, the present invention provides crystalline compound of Formula Xb.

Figure 4:
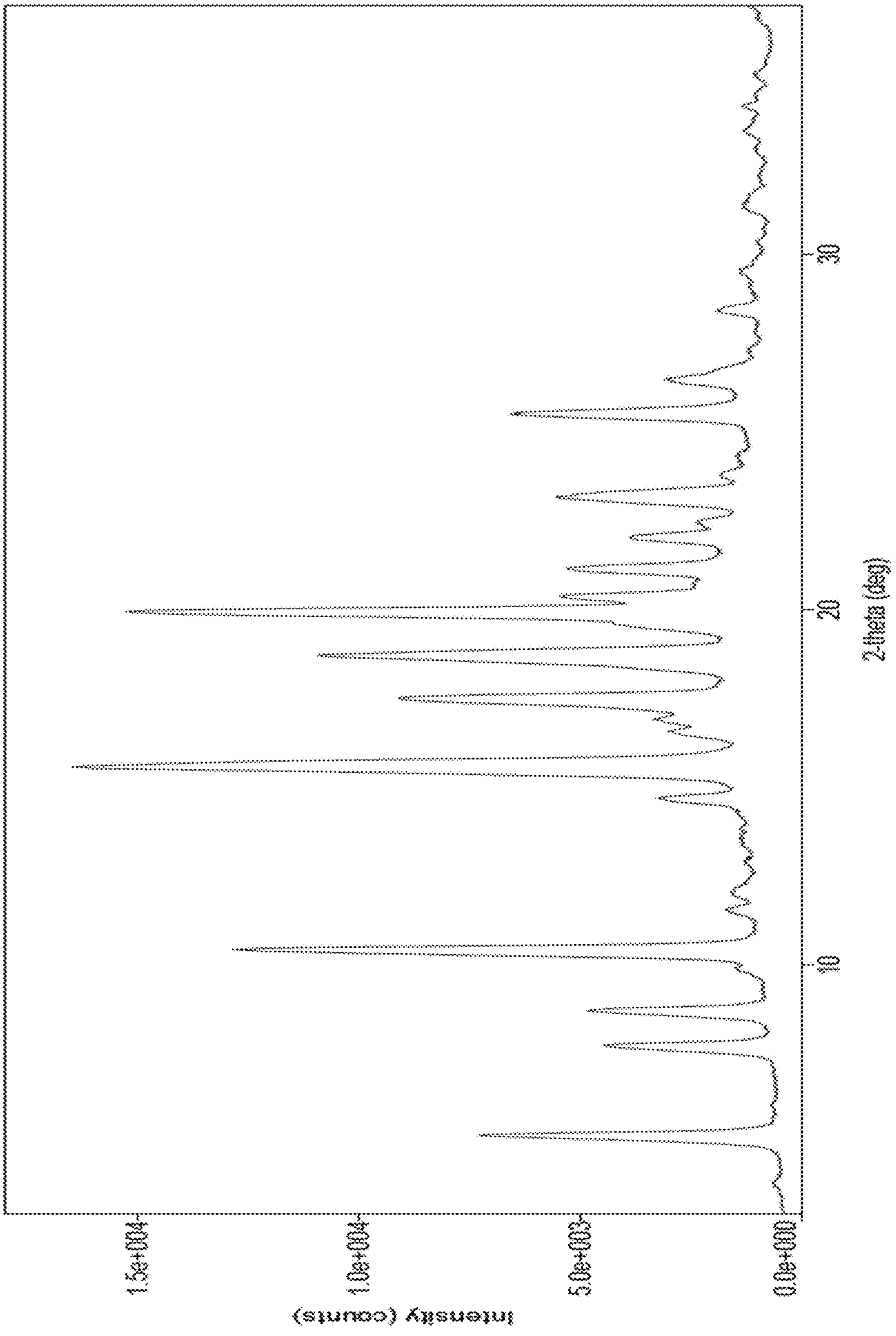
FIG. 4 is the characteristic powder XRD pattern of compound of Formula Xb.

In another embodiment, the present invention provides compound of Formula Xb characterized by X-Ray powder diffraction (PXRD) pattern substantially in accordance with FIG. 4.

In another embodiment, the present invention provides compound of Formula Xb characterized by X-Ray powder diffraction (PXRD) pattern peaks at about 5.2, 7.7, 8.7, 10.4, 14.7, 15.6, 17.0, 17.5, 18.7, 19.5, 19.9, 20.4, 21.1, 22.0, 23.2, 25.5, 26.5, 28.4 and 29.4±0.2° 2θ.

Step b) of the aforementioned process involves optional deprotection of the thus obtained compound of Formula X, wherein when "R1" and "R2" represents a hydrogen or an alcoholic protecting group or both taken together to form a diol protecting group, with a suitable deprotecting agent to obtain Tezacaftor of Formula I.

The deprotection of the compound of Formula X is carried out in presence of a suitable deprotecting agent and a suitable solvent to obtain compound of Formula XI.

Formula XI

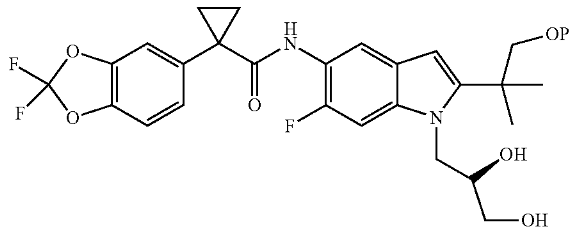

The suitable deprotecting agent used herein for the deprotection of the compound of Formula X includes, but is not limited to organic acid deprotecting agent such as formic acid, acetic acid, propanoic acid, tartaric acid, oxalic acid, maleic acid, mandellic acid, malonic acid, methane sulphonic acid, p-toluene sulphonic acid, trifluoroacetic acid, benzene sulfonic acid and the like and mixture thereof; Inorganic acid deprotecting agent such as hydrochloric acid, hydrobromic acid, hydro iodic acid, sulphuric acid, nitric acid, boric acid, phosphoric acid, chromic acid and the like and mixture thereof; base deprotecting agent such as potassium carbonate, sodium hydroxide, sodium ethoxide and the like and mixture thereof; preferably the suitable deprotecting agent is p-toluene sulphonic acid or hydrochloric acid.

The suitable solvent for deprotection of the compound of Formula X includes but is not limited to water, alcohols, ketones, ethers, amides, sulfoxides and mixtures thereof. The alcohols include, but are not limited to methanol, ethanol, isopropanol and the like; ketones include, but are not limited to acetone, methyl isobutyl ketone, methyl ethyl ketone and the like; ethers include, but are not limited to tetrahydrofuran, 2-methyl tetrahydrofuran, methyl tertiary butyl ether and the like; amides include, but are not limited to dimethyl formamide, dimethyl acetamide, N-methyl pyrrolidinone and the like; sulfoxides include, but are not limited to dimethylsulfoxide, sulfolane and the like; water and the mixtures thereof; preferably the suitable solvent is methanol, water or mixtures thereof.

The deprotection reaction may be carried out at a temperature of about 20° C. to reflux; preferably at about 20° C. to about 60° C.

The resultant compound of Formula XI thus formed can be isolated or further processed without isolating in to next reaction.

Step b) of the aforementioned process also involves optional deprotection of the thus obtained compound of Formula XI, wherein when "P" represents a suitable hydroxyl protecting group, preferably a benzyl with a suitable deprotecting agent to obtain Tezacaftor of Formula I.

The suitable deprotecting agent used herein for the deprotection of the compound of Formula XI, wherein when "P"

represents a suitable hydroxyl protecting group, preferably a benzyl includes but is not limited to palladium on carbon, palladium hydroxide, raney nickel, platinum oxide, cericammoniumnitrate (CAN) in presence of hydrogen source such as ammonium formate, hydrogen gas, acid source such as HCT, HBr, acetic acid, trifluoroacetic acid and the like; preferably the suitable deprotecting agent is palladium on carbon and the hydrogen source is hydrogen gas, hydrochloric acid or mixtures thereof.

The suitable solvent for deprotection of the compound of Formula X wherein when "P" represents a suitable hydroxyl protecting group, includes but is not limited to alcohols, ketones, nitriles, ethers, amides and mixtures thereof. The alcohols include, but are not limited to methanol, ethanol, isopropanol and the like; ketones include, but are not limited to acetone, methyl isobutyl ketone, methyl ethyl ketone and the like; nitriles include, but are not limited to acetonitrile, propionitrile and the like; ethers include, but are not limited to tetrahydrofuran, 2-methyl tetrahydrofuran, dimethyl ether, diisopropyl ether, methyl tertiary butyl ether, 1,4-dioxane and the like; amides include, but are not limited to dimethyl formamide, dimethyl acetamide, N-methyl pyrrolidinone and the like and mixture thereof; preferably the suitable solvent is ethylacetate, tetrahydrofuran, isopropanol or Methanol.

The deprotection reaction may be carried out at a temperature of about 20° C. to reflux temperature; preferably at about 20° C. to about 60° C.

The crude Tezacaftor thus obtained by the process of the present invention may contain Tetramethyl impurity of Formula F, N-Ethyl impurity of Formula G and Di-hydro impurity impurity of Formula H, present in the range of about 0.1% to about 2% by HPLC, which needs to be removed by purification in order to meet regulatory requirements.

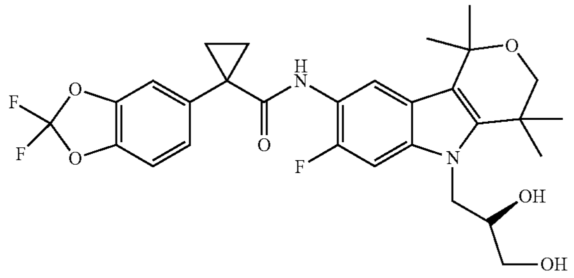

Tetramethyl impurity of Formula F

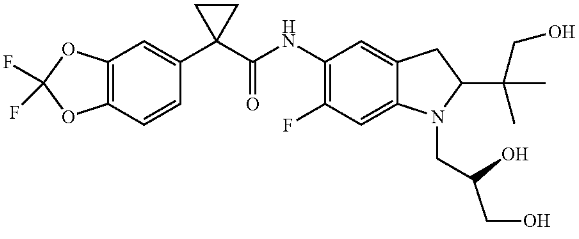

Di-hydro impurity of Formula H

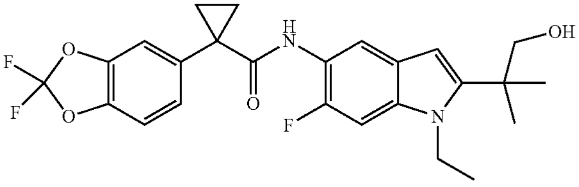

N-Ethyl impurity of Formula G

In another embodiment, the present invention provides a process for purification of Tezacaftor Formula I using a suitable organic solvent system.

In another embodiment, the present invention provides a process for purification of Tezacaftor Formula I, comprising.

a) treating crude Tezacaftor of Formula I with a suitable organic solvent at room temperature to about reflux, and b) isolating the pure Tezacaftor of Formula I.

The suitable organic solvent used herein includes, but is not limited to hydrocarbon solvents, esters, alcohols, ethers, halogenated hydrocarbons; water and mixtures thereof. The hydrocarbon solvents include, but are not limited to toluene, xylene, hexane, heptane, propane, cyclopropane, cyclobutane, cyclopentane, cyclohexane, methyl cyclohexane, cycloheptane, cyclooctane and the like; esters include, but are not limited to ethyl acetate, methyl acetate, isopropyl acetate and the like; alcohols include but are not limited to methanol, ethanol, isopropanol, butanol and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform and the like; water and mixtures thereof; preferably the suitable organic solvent is ethylacetate, isopropanol, cyclohexane, heptane or mixtures thereof; more preferably the suitable solvent is a combination of ethylacetate-heptane or isopropanol-heptane.

The step a) temperature is about room temperature to about reflux, preferably at about room temperature to about 65° C., more preferably at about 45 to 55° C.

The isolation step may be carried out by known techniques such as cooling the solution to precipitation followed by filtration or partial concentrating the reaction solution under vacuum followed by precipitation or complete evaporation of the solvent; preferably the reaction solution may be cooled to less than room temperature and filter the product followed by drying.

In another embodiment, the present invention provides a process for preparation of Tezacaftor of Formula I, comprising:

a) coupling a compound of Formula VII' or a salt thereof with an acid compound of Formula IX or its reactive derivative thereof to obtain a compound of Formula XIV, Formula XIV

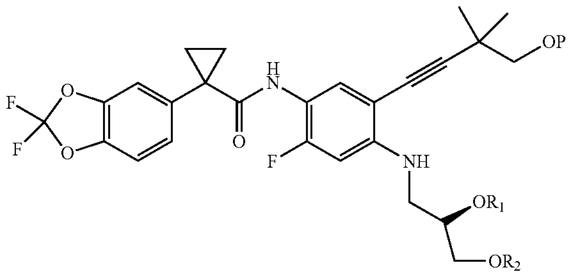

wherein "P" represents hydrogen or a suitable hydroxyl protecting group and "R1" and "R2" may be same or different and represents a hydrogen or an alcoholic protecting group or "R1" and "R2" are taken together to form a diol protecting group;

b) cyclizing the compound of Formula XIV to obtain compound of formula X, wherein “P” “R1” and “R2” are defined as above; and c) optionally deprotecting the compound of Formula X with a suitable deprotecting agent to obtain Tezacaftor of Formula I.

The coupling, cyclization and deprotection processes can be carried out according to the procedures described as above embodiments.

In another embodiment, the present invention provides a compound of Formula XIV:

Formula XIV

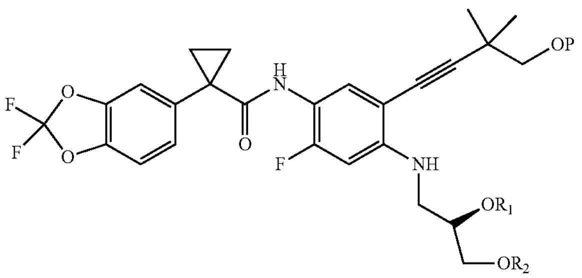

wherein the “P” represents hydrogen or a suitable hydroxyl protecting group and “R1” and “R2” may be same or different and represents a hydrogen or an alcoholic protecting group or “R1” and “R2” are taken together to form a diol protecting group.

In a preferred embodiment, the present invention provides a compound of Formula XIVa:

Formula XIVa

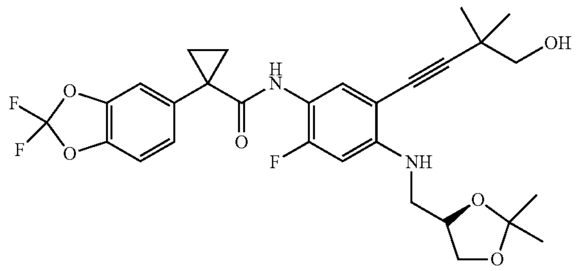

In a preferred embodiment, the present invention provides a compound of Formula XIVb:

Formula XIVb

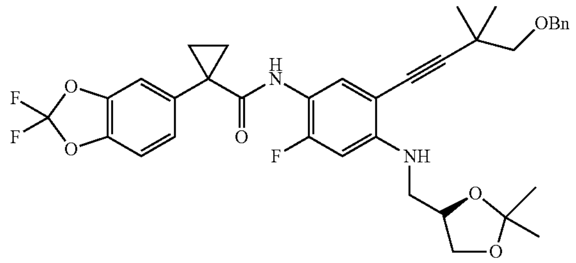

In another embodiment, the present invention provides pure Tezacaftor of Formula I having a total purity greater than 99.5%, as measured by HPLC.

In another embodiment, The present invention provides the pure Tezacaftor of Formula I obtained by above process having chemical purity of at least about 95%, as measured by HPLC, preferably at least about 98%, as measured by HPLC and more preferably at least about 99.5%, as measured by HPLC; and contains less than 0.1% of any impurities, which include Tetramethyl impurity of Formula F, N-Ethyl impurity of Formula G and Di-hydro impurity of Formula H as measured by HPLC.

In accordance with another embodiment, the present invention provides Tezacaftor of Formula I contains less than 0.1% of Tetramethyl impurity of Formula F as determined by HPLC.

In accordance with another embodiment, the present invention provides Tezacaftor of Formula I contains less than 0.1% of N-Ethyl impurity of Formula G as determined by HPLC.

In accordance with another embodiment, the present invention provides Tezacaftor of Formula I contains less than 0.1% of Di-hydro impurity of Formula H as determined by HPLC.

In another embodiment, the present invention provides Tezacaftor of Formula I having less than 0.5% of one or more of process impurities by HPLC.

In another embodiment, the present invention provides a compound of Formula A;

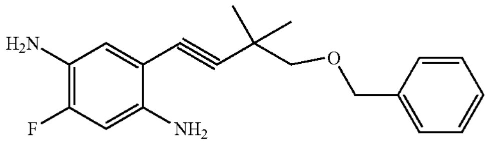

Diamino impurity of Formula A

In another embodiment, the present invention provides a compound of Formula B;

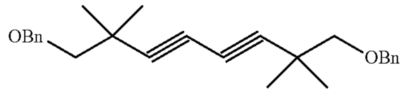

Dimethyl butyne dimer impurity of Formula B

In another embodiment, the present invention provides a compound of Formula C;

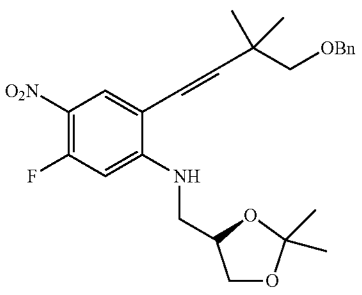

Ene impurity of Formula C

In another embodiment, the present invention provides a compound of Formula D;

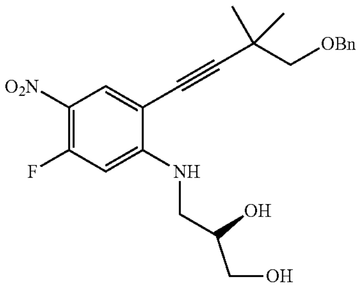

Dioxalane-Diol impurity of Formula D

In another embodiment, the present invention provides a compound of Formula E;

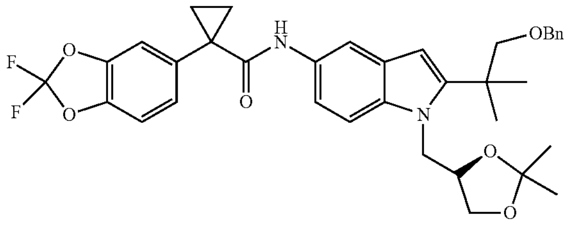

Des fluoro impurity of Formula E

In another embodiment, the present invention provides a compound of Formula F;

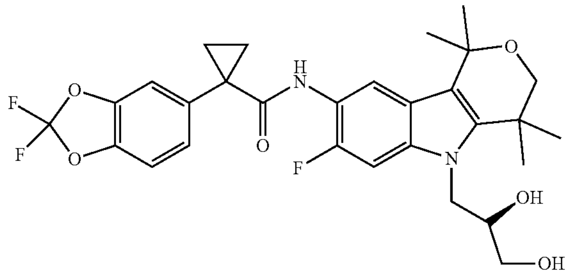

Tetramethyl impurity of Formula F

In another embodiment, the present invention provides a compound of Formula G;

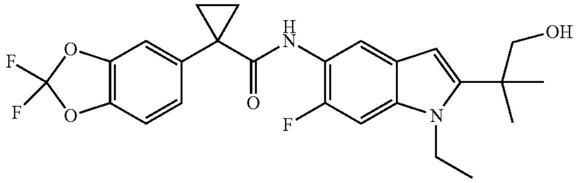

N-Ethyl impurity of Formula G

In another embodiment, the present invention provides a compound of Formula H;

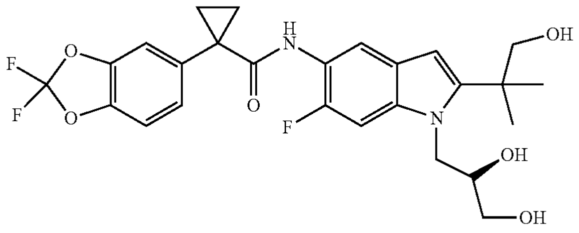

Di-hydro impurity of Formula H

In another embodiment, the present invention provides Tezacaftor of Formula I obtained by the above process and its impurities, were analyzed using high performance liquid chromatography ("HPLC") with the conditions are tabulated below:

| | |
|---|---|
| Column | Zorbax Bonus RP (250 × 4.6) mm |
| Column oven temperature | 40° C. |
| Sample temperature | 5° C. |
| Mobile phase | Mobile phase -A: Buffer: acetonitrile |
| | Mobile phase -B: water: acetonitrile |
| Diluent | Water: acetonitrile |
| Flow rate | 1.0 mL/min |
| Wave length | 210 nm |
| Run time | 60 min |
| Elution mode | Gradient |

Gradient Program:

| Time (min) | Mobile phase-A | Mobile phase-B |
|---|---|---|
| 0 | 30 | 70 |
| 25 | 20 | 80 |
| 35 | 20 | 80 |
| 40 | 10 | 90 |
| 50 | 10 | 90 |
| 52 | 30 | 70 |
| 60 | 40 | 60 |

In another embodiment, the present invention provides a pharmaceutical composition comprising Tezacaftor, prepared by the processes of the present invention and at least one pharmaceutically acceptable excipient.

The process of the present invention is represented schematically in schemes-I & II as follows:

Scheme-I
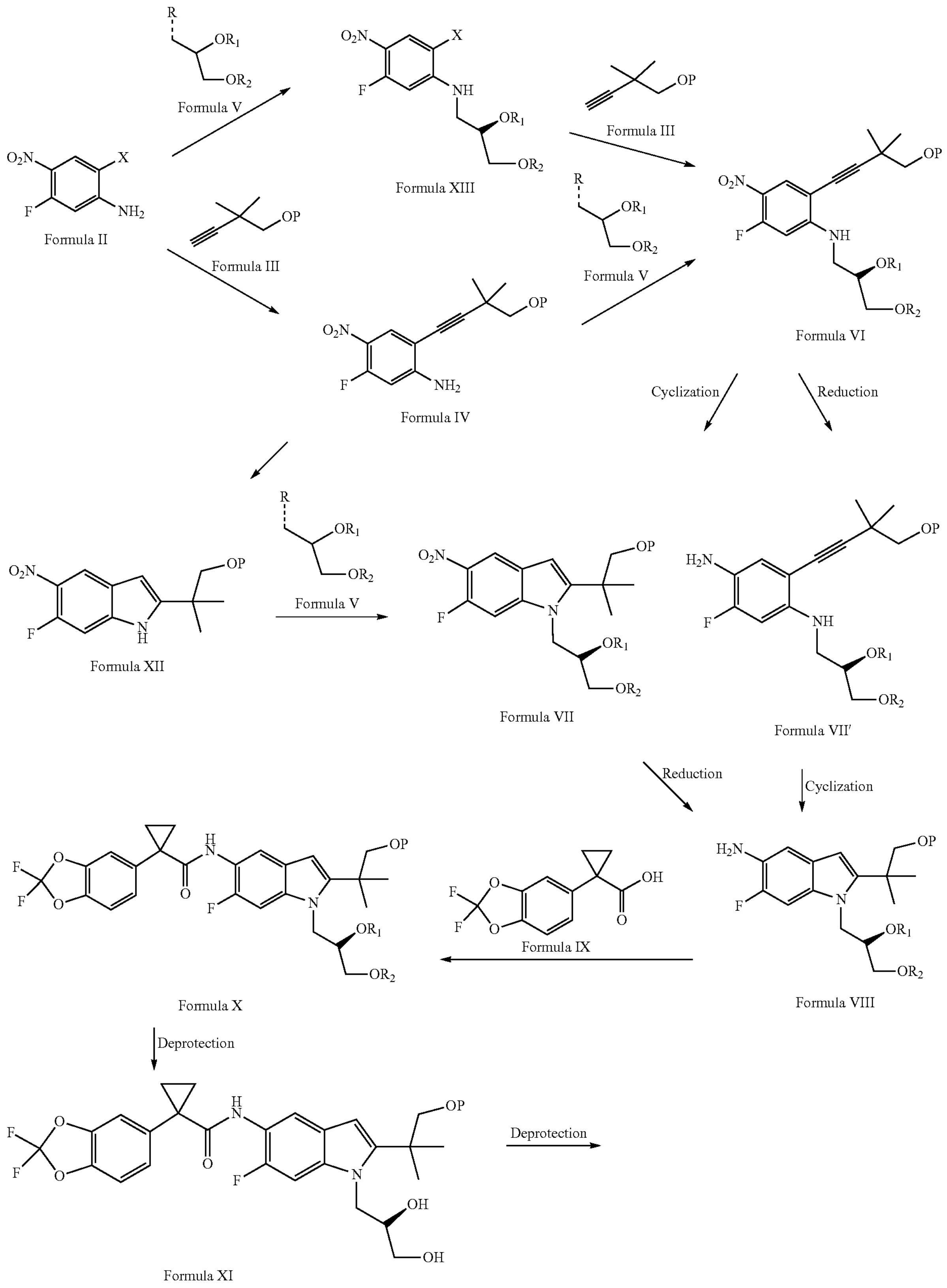
Formula II, Formula XIII, Formula IV, Formula VI, Formula XII, Formula VII, Formula VII', Formula VIII, Formula X, Formula XI -continued
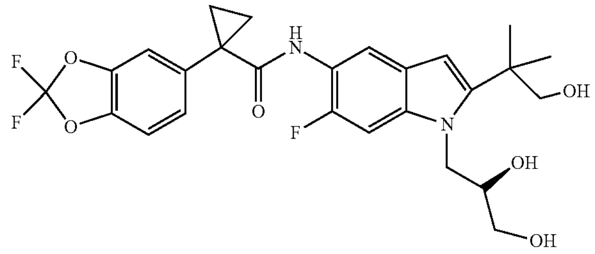
Tezacaftor
Scheme-II
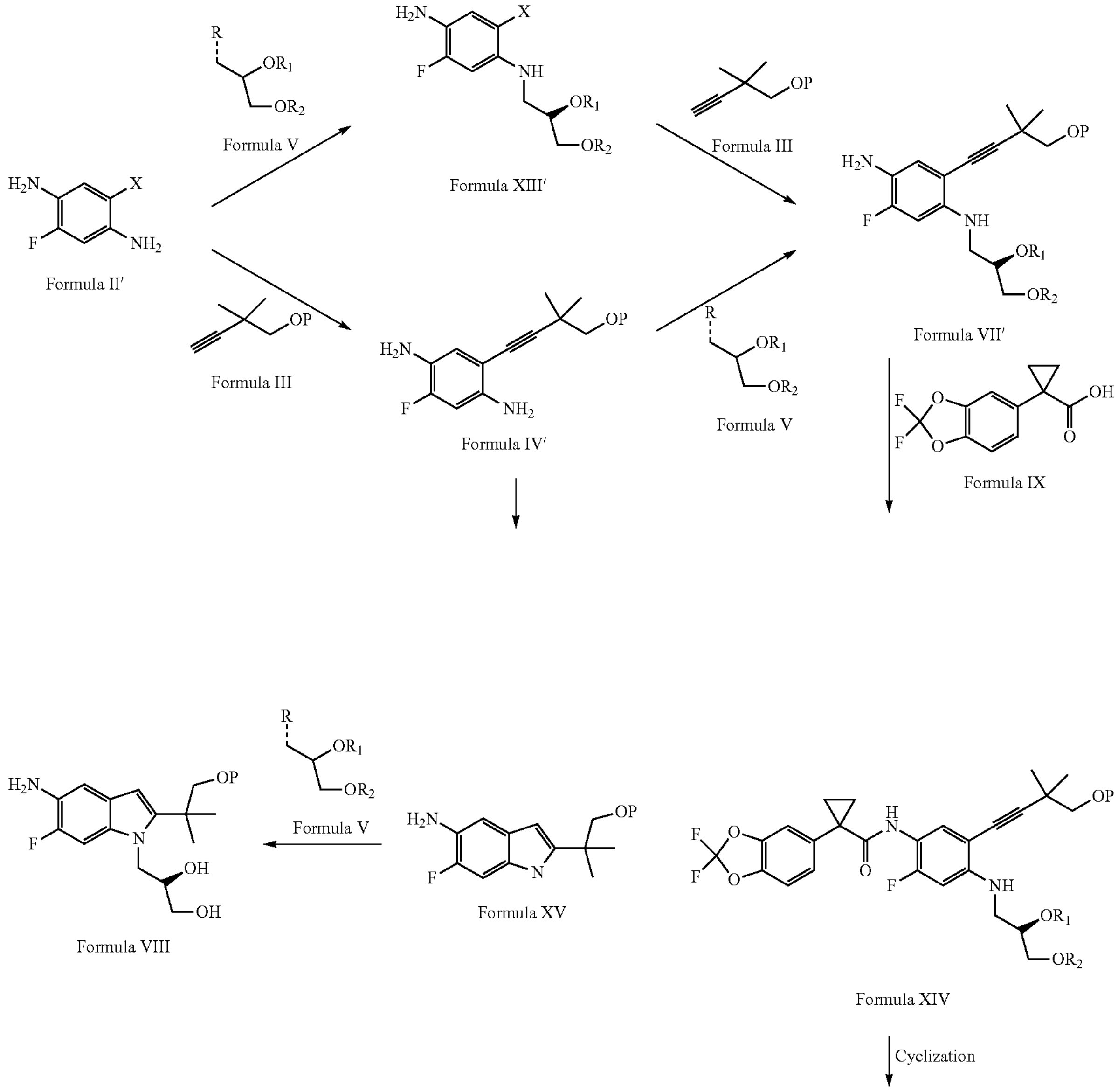

-continued

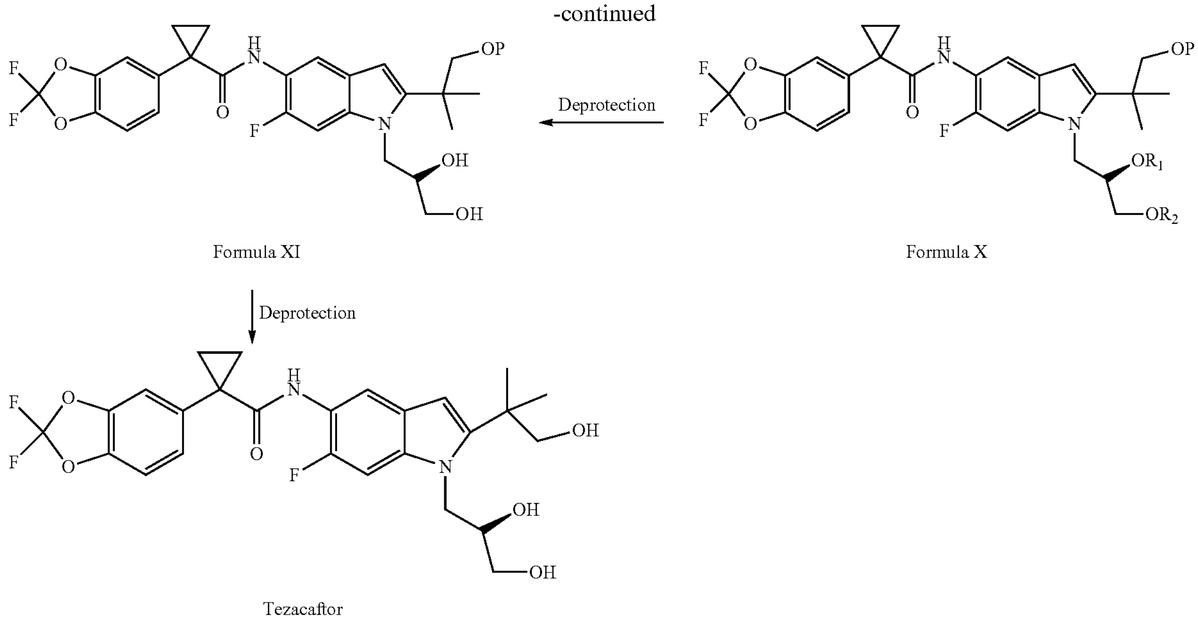

Formula XI

Formula X

Tezacaftor

EXAMPLES

The following non limiting examples illustrate specific embodiments of the present invention. They are not intended to be limiting the scope of the present invention in any way.

Example-1: Preparation of Compound of Formula IVb

Potassium carbonate (44 gms) in acetonitrile (200 mL), Pd(OAc)2 (0.23 gms), 1,4-bis(diphenylphosphino)butane (0.68 gms) and CuI (0.3 gms) were added in to a round bottom flask at 25° C. and stirred for 15 mins. [(2,2-dimethylbut-3-yn-1-yl)oxymethyl]benzene of Formula IIIb (36 gms) and 2-bromo-5-fluoro-4-nitroaniline of Formula IIa (25 gms) were added to the reaction mass and stirred for 60 mins at ambient temperature. The temperature of reaction mass was gradually raised to mild reflux at 80-82° C. and stirred for 2 h at the same temperature. The reaction mass was allowed to cool to ambient temperature and filtered. The filtrate was concentrated under reduced pressure at below 50° C. and the obtained residue was dissolved in ethyl acetate (125 mL), washed with 5% EDTA solution (75 mL) and concentrated under vacuum. Cyclohexane (225 mL) was added to the residue and temperature of the reaction mass was raised to 45-50° C., stirred for 1 h. The reaction mass was cooled to 15-20° C. and maintained for 2 hrs, filtered, washed with cyclohexane (25 mL) and dried the material at 55-60° C. to obtain the title compound. Yield: 33.8 gms; HPLC Purity: 97.0%.

LC-MS m/z: 343.3 (M+1).

$^1$H NMR (300 MHz, DMSO-$d_6$) δ 7.88 (d, J=8.4 Hz, 1H, Ar—H), 7.37-7.26 (m, 5H, Ar—H), 6.84 (brs, 2H, $NH_2$), 6.59 (d, J=14.4 Hz, 1H, Ar—H), 4.59 (s, 2H, Ph-$CH_2$), 3.43 (s, 2H, O—$CH_2$—), 1.30 (s, 6H, $2CH_3$)

Example-2: Preparation of Compound of Formula IVb

Potassium carbonate (176 gms), 2-bromo-5-fluoro-4-nitroaniline of Formula IIa (100 gms), acetonitrile (700 mL), Pd(OAc)2 (0.92 gms), 1,4-bis(diphenylphosphino)butane (2.72 gms) and CuI (1.23 gms) were added in to a round bottom flask and gradually raised to reflux at 77-83° C. [(2,2-dimethylbut-3-yn-1-yl)oxymethyl]benzene of Formula IIIb (112 gms) in acetonitrile (100 mL) was added slowly over a period of 1-2 h. The temperature of reaction mass was maintained at reflux at 77-83° C. and stirred for 5-6 h. The reaction mass was allowed to cool to ambient temperature and filtered. The filtrate was concentrated under reduced pressure at below 50° C. and the obtained residue was dissolved in toluene (1000 mL), washed with 2% EDTA solution (300 mL×2), followed by water (300 mL). The resulting organic layer was distilled until 4 vols are left behind under vacuum while maintaining the temperature below 60° C. Cyclohexane (400 mL) was added to the residue over a period of 30-60 min and temperature of the reaction mass was raised to 47-53° C., stirred for 30-45 mins. The reaction mass was gradually cooled to 17-23° C. over a period of 4-5 hrs and maintained for 4-5 hrs, filtered, washed with cyclohexane (100 mL×2) and dried the material at 25-35° C. to obtain the title compound. Yield: 115 gms. The PXRD is set forth in FIG. 1.

Example-3: Preparation of Compound of Formula IVb

Potassium carbonate (88 gms) in acetonitrile (400 mL), Pd(OAc)2 (0.46 gms), 1,4-bis(diphenylphosphino)butane (0.46 gms) and CuI (0.3 gms) were added in to a round bottom flask at 25° C. and stirred for 20 mins. [(2,2-dimethylbut-3-yn-1-yl)oxymethyl]benzene of Formula IIb (50 gms) and 2-bromo-5-fluoro-4-nitroaniline of Formula IIa (50 gms) were added to the reaction mass and stirred for 60 mins at ambient temperature. The temperature of reaction mass was gradually raised to mild reflux at 80-82° C. and stirred for 2 h at the same temperature. The reaction mass was allowed to cool to ambient temperature and filtered. The filtrate was concentrated under reduced pressure at below 50° C. and the obtained residue was dissolved in ethyl acetate (250 mL), washed with 5% EDTA solution (150 mL) and concentrated under vacuum. Cyclohexane (450 mL) was added to the residue and temperature of the reaction mass was raised to 45-50° C., stirred for 1 h. The reaction mass was cooled to 15-20° C. and maintained for 2 hrs, filtered, washed with cyclohexane (50 mL) and dried the material at 55-60° C. to obtain the title compound. Yield: 66.3 gms; HPLC Purity: 97.0%.

Example-4: Preparation of Compound of Formula Va

D-Mannitol (100 gms), THF (500 ml) and 2,2-dimethoxy propane (143 gms) were added in to a round bottom flask at 25-35° C. and stirred for 20 mins. Stannous chloride dihydrate (0.5 gms) was added to the reaction mass and the temperature of reaction mass was gradually raised to 54-60° C. and stirred for 2-3 hrs at the same temperature. Pyridine was added to the cooled reaction mass at 40-50° C., temperature was raised to 55-65° C. and concentrated. Methylene chloride (100 mL) was added to the residue at 35-45° C., stirred for 20 mins and distill of the solvent at 45° C. Methylene chloride (600 mL) was added to the residue at 25-35° C., stirred for 20-40 mins and filtered. Sodium bicarbonate (5 gms) and water (25 mL) were added to the filtrate. sodium metaperiodate (90 g in 10 equal lots) was added to the resulting biphasic mixture at 12-18° C., the temperature of biphasic mixture was raised to 25-31° C., stirred at the same temp for 3-5 hrs and filtered. Sodium bicarbonate (15 gms) was added to the resulting filtrate at 25-35° C., filtered and distilled out the solvent completely under vacuum at below 50° C. followed by distillation under high vacuum at 45-85° C. to get the title compound. Yield: 55 gms.

Example-5: Preparation of Compound of Formula VIb

Compound of Formula IVb (5 gms) and methylene chloride (50 mL) were added in to a round bottom flask and allowed to cool to −13° C. to −17° C. Trifluoroacetic acid (6.25 mL) and Sodium triacetoxyborohydride (11.1 gms) were added to the reaction mass. (4S)-2,2-dimethyl-1,3-dioxolane-4-carbaldehyde of formula Va solution (4.15 gms in 10 mL of methylene chloride) was added to the reaction mass, stirred for 1 hr at −13° C. to −17° C. The reaction mass was poured into 5% aqueous sodium bicarbonate (25 mL). The layers were separated and the aqueous layer was extracted with methylene chloride (10 mL). The combined organic layer was washed with 5% aqueous sodium bicarbonate (25 mL) and concentrated. The residue obtained was purified by silica gel column chromatography using a gradient of 5-10% ethyl acetate and n-hexane to obtain the title compound as orangish yellow oil. Yield: 4.2 gms; HPLC Purity: 96.5%. LC/MS m/z: 457(M+1).

$^1$H NMR (300 MHz, DMSO-$d_6$) δ 7.91 (d, J=8.7 Hz, 1H, Ar—H), 7.38-7.27 (m, 5H, Ar—H), 6.81 (d, J=15.3 Hz, 1H, Ar—H), 6.27 (t, J=4.9 Hz, 1H, NH), 4.60 (s, 2H, Ph-$CH_2$), 4.26-4.23 (m, 1H, CH), 4.00 (dd, J1J2=6.3 Hz, J2=6.3 Hz, 1H, N—$CH_2$), 3.64 (dd, J1=6.0 Hz, J2=6.0 Hz, 1H, N—$CH_2$), 3.51-3.45 (m, 1H, O—$CH_2$), 3.43 (s, 2H, —$CH_2$OBn, 3.36-3.30 (m, 1H, O—$CH_2$), 1.31 (s, 9H, 3$CH_3$), 1.25 (s, 3H, $CH_3$).

Example-6: Preparation of Compound of Formula VIb

Compound of Formula IVb (100 gms) and tetrahydrofuran (250 mL) were added in to a round bottom flask and allowed to stir at 25° C. to 35° C. for 15-30 mins. Gradually cool the temperature of the reaction mass to 7-13° C. Trifluoroacetic acid (100 mL) and (4S)-2,2-dimethyl-1,3-dioxolane-4-carbaldehyde of formula Va solution (95 gms in 80 mL of tetrahydrofuran) were added while maintaining temperature below 20° C. This reaction mass was added to a mixture of Sodium triacetoxyborohydride (186 gms) in tetrahydrofuran (400 mL) while maintaining temperature below 25° C. The resulting reaction mass was stirred for 2-3 hr at 27° C. to 33° C. The reaction mass was poured into aqueous sodium bicarbonate (200 gms in 2000 mL of water), extracted with methyl tertbutyl ether (1000 mL). The organic layer was washed with aqueous sodium bicarbonate (500 mL×2) and distill of the solvent at 50° C. and co-evaporated with isopropanol (100 mL). HPLC analysis revealed the content of Diamino impurity of Formula A: about 2 to 3%; Dimethyl butyne dimer impurity of Formula B: about 2 to 3%; Ene impurity of Formula C: about 0.5% to 1% and Dioxalane-Diol impurity of Formula D: about 0.5%.

To the resulting residue isopropanol (500 mL) was added, cooled to 25-35° C. and added seed material (0.5 gms). Stirred the reaction mass at 25-35° C. for 3-4 h and water (100 mL) was added over 45-60 min, at 25-35° C. the reaction mass was gradually cooled to 7-13° C., stirred for 8-10 h, filtered, washed with isopropanol (100 mL) and dried the material at 27-33° C. to obtain the title compound.

Yield: 90 gms; HPLC Purity: 98.0%; Diamino impurity of Formula A: about 0.18%; Dimethyl butyne dimer impurity of Formula B: about 0.03%; Ene impurity of Formula C: about 0.08% and Dioxalane-Diol impurity of Formula D: about 0.04%. The PXRD is set forth in FIG. 2.

Example-7: Preparation of Compound of Formula VIb

Compound of Formula IVb (65 gms) and tetrahydrofuran (195 mL) were added in to a round bottom flask and allowed to cool to 7° C. to 13° C. Trifluoroacetic acid (65 mL) and Sodium triacetoxyborohydride (140.5 gms) were added to the reaction mass. (4S)-2,2-dimethyl-1,3-dioxolane-4-carbaldehyde of formula Va solution (62 gms in 65 mL of tetrahydrofuran) was added to the reaction mass, stirred for 1 hr at 7° C. to 13° C. The reaction mass was poured into aqueous sodium bicarbonate (130 gms in 1300 mL). The layers were separated and the aqueous layer was extracted with methyl tert-butyl ether (720 mL). The combined organic layer was washed with 5% aqueous sodium bicarbonate (200 mL) and concentrated and co-evaporated with cyclohexane (2×65 mL). The residue obtained was dissolved in cyclohexane (260 mL) preheated to 42° C. to 48° C., cooled to 7° C. to 13° C. and filtered to afford the title compound as orangish yellow color solid. Yield: 64 gms; HPLC Purity: 93.9%.

Example-8: Preparation of Compound of Formula VIb

Compound of Formula IVb (10 gms) and tetrahydrofuran (80 mL) were added in to a round bottom flask and allowed to cool to −13° C. to −17° C. Trifluoroacetic acid (12.5 mL) and Sodium triacetoxyborohydride (21.6 gms) were added to the reaction mass. (4S)-2,2-dimethyl-1,3-dioxolane-4-carbaldehyde of formula Va solution (8 gms in 20 mL of tetrahydrofuran) was added to the reaction mass, stirred for 3-5 hrs at 17° C. to 23° C. The reaction mass was poured into 5% aqueous sodium bicarbonate (100 mL). The layers were separated and the aqueous layer was extracted with methyl tert-butyl ether (100 mL). The combined organic layer was washed with 5% aqueous sodium bicarbonate (50 mL) and concentrated to afford the title compound as orangish yellow oil. Yield: 13.6 gms.

Example-9: Preparation of Compound of Formula VIb

The procedure described in example 5 was repeated using 15 volumes of tetrahydrofuran instead of 10 volumes of tetrahydrofuran to yield 13.2 gms of the title compound.

Example-10: Preparation of Compound of Formula VIb

The procedure described in example 5 was repeated using 5 volumes of tetrahydrofuran instead of 10 volumes of tetrahydrofuran to yield 13.1 gms of the title compound.

Example-11: Preparation of Compound of Formula VIb

Compound of Formula IVb (10 gms) and tetrahydrofuran (80 mL) were added in to a round bottom flask and allowed to cool to −13° C. to −17° C. (4S)-2,2-dimethyl-1,3-dioxolane-4-carbaldehyde of formula Va solution (8 gms in 10 mL of tetrahydrofuran) and trifluoroacetic acid (12.5 mL) were added to the reaction mass and stirred for 10 mins. Sodium triacetoxyborohydride (21.6 gms) was added to the reaction mass, stirred for 3-5 hrs at 17° C. to 23° C. The reaction mass was poured into 5% aqueous sodium bicarbonate (100 mL). The layers were separated and the aqueous layer was extracted with methyl tert-butyl ether (100 mL). The combined organic layer was washed with 5% aqueous sodium bicarbonate (50 mL) and concentrated to afford the title compound as orangish yellow oil. Yield: 12.8 gms.

Example-12: Preparation of Compound of Formula VIb

Cesium carbonate (33.8 gms) was added to a compound of Formula IVb (2 gms) in dimethylformamide (20 mL) in a round bottom flask at 25° C. (S)-1-O-Tosyl-2,3-O-isopropylidene-glycerol of formula Vb (2 gms) was added to the reaction mass, stirred at 87° C. to 93° C. HPLC analysis revealed significant amount of unreacted starting material even after maintaining for 20 h.

Example-13: Preparation of Compound of Formula VIIb

Compound of Formula VIb (1 gm) was dissolved in dimethylformamide (10 mL) in a round bottom flask at 25° C. Tetra-n-butylammonium fluoride (1M solution in 8 mL THF) was added to the resulting solution, stirred for 1 h at 80° C. and then cooled to ambient temperature. Water (10 mL) was added to the reaction mass and extracted with methyl tert-butyl ether. The organic extracts was washed with 10% sodium chloride (5 mL) solution and concentrated under vacuum to afford the title compound as dark colored oil. Yield: 0.8 gins. HPLC Purity: 95.0%.

LC/MS m/z: 457.5 (M+1).

$^1$H NMR (300 MHz, DMSO-$d_6$) δ 8.35 (d, J=7.5 Hz, 1H, Ar—H), 7.66 (d, J=13.5 Hz, 1H, Ar—H), 7.34-7.23 (m, 5H, Ar—H), 6.58 (s, 1H, ArCH), 4.59-4.34 (m, 5H, Ph-$CH_2$O—CH, O—$CH_2$), 4.09 (dd, J1=6.3 Hz, J2=6.3 Hz, 1H, N—$CH_2$), 3.71-3.57 (m, 3H, BnOCH2, N—$CH_2$), 1.45 (s, 3H, $CH_3$), 1.42 (s, 3H, $CH_3$), 1.40 (s, 3H, $CH_3$), 1.17 (s, 3H, $CH_3$).

Example-14: Preparation of Compound of Formula VIIb

Compound of Formula VIb (70 gms) was dissolved in dimethylformamide (600 mL) in a round bottom flask at 25° C. Tetra-n-butylammonium fluoride (1M solution in 650 mL THF) was added to the resulting solution, stirred for 1 h at 80° C. and then cooled to ambient temperature. Water (840 mL) was added to the reaction mass and extracted with methyl tert-butyl ether. The organic extracts was washed with 10% sodium chloride solution and concentrated under vacuum to afford the title compound as dark colored oil.

Yield: 70 gins.

Example-15: Preparation of Compound of Formula VIIIb

Compound of Formula VIIb (1.5 gms) was dissolved in methanol (15 mL) in a round bottom flask at 25° C. Raney-nickel (0.3 gms) was added to the resulting mass and maintained for 3 h under hydrogen gas atmosphere at ambient temperature. Filtered the catalyst and washed with methanol. The filtrate was concentrated to afford the title compound. Yield: 1.2 gins.

LC/MS m/z: 428(M+1).

$^1$H NMR (300 MHz, DMSO-$d_6$) δ 7.33-7.25 (m, 6H, Ar—H), 7.17 (d, J=12.6 Hz, 1H, Ar—H), 6.76 (d, J=9 Hz, 1H, Ar—H), 6.05 (s, 1H, Ar—H), 4.48 (s, 4H, $NH_2$, Ph-$CH_2$), 4.36-4.23 (m, 2H, N—$CH_2$), 4.02 (q, J=4.5 Hz, 1H, CH), 3.66-3.52 (m, 4H, BnO—$CH_2$, O—$CH_2$), 1.39 (d, J=2.4 Hz, 9H, 3×$CH_3$), 1.18 (s, 3H, $CH_3$).

Example-16: Preparation of Compound of Formula VIIIb as Oxalate Salt

Compound of Formula VIb (100 gm) was dissolved in tetrahydrofuran (300 mL) in a round bottom flask at 25° C. Tetra-n-butylammonium fluoride (1M solution in THF; 350 mL) was added to the resulting solution, stirred for 3 h at 52-58° C. and then cooled to ambient temperature. Water (500 mL) was added to the reaction mass and extracted with methyl tert-butyl ether (800 mL). The organic extracts was washed with water (500 mL×2), evaporated under vacuum and co-evaporated with methanol (100 mL). The resulting residue was dissolved in mixture of Tetrahydrofuran (300 mL) and methanol (100 mL). This reaction mass was added to $NaBH_4$—$NiCl_2$ mixture [prepared by adding Nickel (II) chloride (5.2 g) to $NaBH_4$ (20.7 g) in tetrahydrofuran (100 mL) at 0-3° C.] while maintaining temperature below 20° C. Gradually raised the temperature to 25-35° C. and maintained for 3 h. Water (300 mL) was added to the reaction mass, stirred for 20-30 min at 25-35° C. followed by 5% aq ammonium chloride solution [$NH_4Cl$ (5 g) dissolved in water (100 mL)]. Filter the reaction mass and distil the solvent while maintaining temperature below 60° C. till approx 4 volumes are left behind. Cooled the reaction mass to 25-35° C., extracted with toluene (750 mL), washed organic layer with 10% aq NaCl solution [30 g; dissolved in water (300 mL) and distil of the solvent under vacuum below 60° C. and co-evaporated with methyl tert-butyl ether (100 mL). dissolved the resulting residue in methyl tert-butyl ether (300 mL) and oxalic acid (20 g) was added. The reaction mass was maintained at 25-355° C. for 4-5 h, cooled to 7-13° C., stir for another 3-4 h, filtered, washed with chilled methyl tert-butyl ether (100 mL) followed by cyclohexane (100 mL) and dried the material at 25-35° C. for 1-2 h and at 47-53° C. to afford the title compound. Yield: 85 gms. The PXRD is set forth in FIG. 3.

Example-17: Preparation of Compound of Formula VIIIb

Compound of Formula VIIb (70 gms) was dissolved in methanol (700 mL) in a round bottom flask at 25° C. Raney-nickel (7.3 gms) was added to the resulting mass and maintained for 3 h under hydrogen gas atmosphere at ambient temperature. Filtered the catalyst and washed with methanol. The filtrate was concentrated to afford the title compound. Yield: 60 gms.

Example-18: Preparation of Compound of Formula VIIIb

Compound of Formula VIIb (80 gms) and methanol (960 mL) were added in to a round bottom flask and allowed to cool to 2° C. to 5° C. Nickel chloride (34 gms) and sodium borohydride (19.8 gms) were added to the reaction mass, maintained for 45 min. Water (150 mL) was added to the reaction mass and then concentrated under reduced pressure till 2 volumes left. Ethyl acetate (700 mL) and water (150 mL) were added and the bi-phasic mixture was stirred for 20 min. The organic layer was separated and concentrated under vacuum to afford title compound as oily mass. Yield=74 gms. Purity by HPLC 93%.

Example-19: Preparation of Compound of Formula VIIIb

Compound of Formula VIIb (2 gms) and methanol (60 mL) were added in to a round bottom flask and allowed to cool to 0° C. to 5° C. Sodium borohydride (0.5 gms) was added to the reaction mass, stirred for 2 hrs. Water (10 mL) was added to the reaction mass and then concentrated under reduced pressure. Ethyl acetate (25 mL) and water (25 mL) were added and the bi-phasic mixture was stirred for 10 min. The organic layer was separated and concentrated under vacuum to afford title compound as oily mass. Yield=1.8 gms.

Example-20: Preparation of Compound of Formula VIIIb

Ammonium formate (0.55 gms) and 10% Pd/C (~50% wet; 100 mg) were added to a compound of Formula VIIb (1 gm) in methanol (960 mL) in a round bottom flask at 25° C. The temperature of the reaction mass was raised to 50-55° C. and the mixture aged for 3 hrs. The reaction mass was cooled to room temperature and the catalyst was filtered. Ethyl acetate (20 mL) was added to the filtrate, washed with Brine solution (20 mL) and then concentrated to afford title compound. Yield=0.9 gms.

Example-21: Preparation of Compound of Formula Xb

Dimethyl formamide (1 mL) and a solution of oxalyl chloride (8.6 mL) in methylene chloride (26 mL) were added to a compound of Formula IX (16.1 gms) in methylene chloride (104 mL) in a round bottom flask at 25° C. The temperature of the reaction mass was raised to mild reflux at 38-40° C., aged at the same temperature for 3 h. The reaction mass was cooled to room temperature and a solution of N,N-diisopropylethylamine (28.6 mL) in methylene chloride (52 mL) was added over a period of 1 h. A solution of intermediate VIIIb (26 gms) in methylene chloride (78 mL) was added to the resulting reaction mass. The temperature of the reaction mass was raised to mild reflux at 38-40° C. and aged at the same temperature for 3 hrs. The reaction mass was cooled to ambient temperature, washed with aq 5% $NaHCO_3$ solution (50 mL) and 5% aq NaCl solution (50 mL) and the layers were separated. The organic layer was concentrated under reduced pressure at below 50° C. The resulting residue was purified by silica gel column chromatography using a gradient of 5-20% v/v ethyl acetate and n-hexane to afford title compound. Yield=28.5 gms.

Purity by HPLC: 98%.

LC/MS m/z: 651.6 (M+1).

$^1$H NMR (300 MHz, DMSO-$d_6$) δ 8.31 (s, 1H, NH), 7.53 (s, 1H, Ar—H), 7.52-7.22 (m, 9H, Ar—H), 6.26 (s, 1H, Ar—H), 4.47 (s, 2H, Ph-$CH_2$), 4.41-4.29 (m, 2H, N—$CH_2$), ≈4.03 (t, J=4.6 Hz, CH), 3.63-3.56 (m, 4H, BnO—$CH_2$, O—$CH_2$), 1.46 (t, J=3.2 Hz, 2H, $CH_2$), 1.41 (s, 3H, $CH_3$), 1.40 (s, 3H, $CH_3$), 1.38 (s, 3H, $CH_3$), 1.16-1.13 (m, 5H, $CH_3$, cyclopropyl-$CH_2$).

Example-22: Preparation of Compound of Formula Xb

Compound of Formula VIIIb as oxalate salt (100 g) dissolved in methylene chloride (800 mL) was taken in a round bottom flask and washed with aqueous solution of $NaHCO_3$ (750 mL). The resulting organic layer was washed with water (300 mL) and concentrated. The resulting residue was dissolved in methylene chloride (300 mL) and triethylamine (59.2 g) was added and cooled the solution to 0-3° C. to get the base solution.

Thionyl chloride (24 mL) was added to a mixture of compound of Formula IX (56.4 g), dimethyl formamide (4 mL) in methylene chloride (400 mL) and temperature of the reaction mass was raised to reflux at 36-40° C., aged at the same temperature for 3 h. The reaction mass was distilled till 1.5 volumes are left behind at atmospheric pressure, co-distilled with toluene (200 mL) under vacuum till 1 volume is left behind and methylene chloride (200 mL) was added to get the acid chloride solution.

The acid chloride solution was added to the base solution prepared above while maintain temperature below 15° C. The temperature of the reaction mass was gradually raised to 27-33° C. and aged at the same temperature for 2 hrs. The resulting reaction mass was washed with aq $NaHCO_3$ solution (25 gms dissolved in 500 mL water) and the resulting organic layer was sequentially washed with 2N NaOH solution (40 g dissolved in 500 mL water) and water (300 mL). The organic layer was distilled off the solvent completely while maintaining temp below 40° C. and co-distilled with methanol (100 mL). HPLC analysis revealed the content of desfluoro impurity of Formula E: about 0.2 to 0.5%;

The resulting residue was dissolved in methanol (700 mL) at 47-53° C., gradually cooled to 25-35° C. and stirred for 3-4 h. Further cooled the mixture to 7-13° C., stirred for 2-3 h, filtered, washed with chilled methanol (100 mL) and dried at 25-35° C. for 1-2 h and at 57-63° C. for 6-8 h to afford the title compound. Yield=80 gins. Purity by HPLC: 99%; desfluoro impurity of Formula E: about 0.06%; The PXRD is set forth in FIG. 4.

Example-23: Preparation of Compound of Formula XIb

P-toluenesulfonic acid monohydrate (0.3 gms) and water (8 mL) were added to a compound of Formula Xb (5 gms) in methanol (80 ml) in a round bottom flask at 25° C. The temperature of the reaction mass was raised to 70-75° C. and maintained for 3 hrs. The reaction mass was cooled to 45-50° C. and the solvent was removed under reduced pressure at below 50° C. Ethyl acetate (30 ml) was added to the resulting residue, washed with aq 5% $NaHCO_3$ solution (15 mL), water (15 mL) and 5% aq NaCl solution (15 mL) and the layers were separated. The organic layer was evaporated to dryness and the residue obtained was purified by reverse phase flash chromatography eluted from acetonitrile-water 35:65 v/v to afford title compound. Yield=3.1 gins.

Purity by HPLC 95%

LC/MS m/z: 611.5 (M+1).

$^1$H NMR (300 MHz, DMSO-$d_6$) δ 8.31 (s, 1H, NH), 7.52 (s, 1H, Ar—H), 7.42-7.21 (m, 9H, Ar—H), 6.24 (s, 1H, Ar—H), 4.92 (t, J=5.4 Hz, 2H, 2×OH), 4.47 (s, 2H, Ph-$CH_2$), 4.38 (dd, J1=2.4 Hz, J2=1.8 Hz, 1H, N—$CH_2$), 4.08-4.00 (m, 1H, N—$CH_2$), 3.84 (brs, 1H, CH), 3.63 (q, J=10.0 Hz, 2H, BnO—$CH_2$), 3.45-3.33 (m, 2H, $CH_2$OH), 1.47 (q, J=3.5 Hz, 2H, Cyclopropyl-$CH_2$), 1.41 (s, 6H, 2×$CH_3$), 1.13 (q, J=3.6 Hz, 2H, Cyclopropyl —$CH_2$).

Example-24: Preparation of Compound of Formula XIb

Compound of Formula Xb (1 gm) was dissolved in methanol (10 mL) in a round bottom flask at 25° C. Con HCl (0.3 mL) and water (0.1 mL) were added to the reaction mass, stirred for 3 hrs at ambient temperature. The reaction mass was partitioned between ethyl acetate (10 mL) and water (5 mL) and the layers were separated. The organic layer was washed with 5% aq $NaHCO_3$ (2×20 mL) and 5% aq sodium chloride solution (20 mL) and then concentrated under reduced pressure to afford title compound. Yield=0.8 gins.

Example-25: Preparation of Compound of Formula XIb

Compound of Formula Xb (80 gms) was dissolved in methanol (800 mL) in a round bottom flask at 25° C. P-toluenesulfonic acid monohydrate (10.3 gms) and water (80 mL) were added to the reaction mass. The temperature of the reaction mass was raised to 70-75° C. and maintained for 3 hrs. The reaction mass was cooled to 45-50° C. and the solvent was removed under reduced pressure at below 50° C. Ethyl acetate (480 mL) was added to the resulting residue and washed sequentially with 5% aq $NaHCO_3$ (240 mL), water (240 mL) and 5% aq NaCl solution (240 mL) and the layers were separated. The organic layer was evaporated to dryness to afford title compound. Yield=75 gins.

Example-26: Preparation of Tezacaftor of Formula I

Compound of Formula XIb (7.0 gms) was charged in to an Autoclave. MeOH (50 mL), methanolic HCl (0.7 mL) and 5% Pd/C (~50% wet; 1.0 g) were added to the Autoclave. The autoclave was pressurized with hydrogen gas (4-5 kg/$cm^2$) and the temperature was gradually raised to 50-55° C., maintained for 3 hrs under hydrogen atmosphere. The reaction mass was cooled to ambient temperature and the catalyst was filtered. The filtrate was concentrated under reduced pressure and the obtained residue (foamy solid) was crystallized from a mixture of isopropyl alcohol and heptane to afford Tezacaftor of Formula I. Yield=4.6 gms.

Purity by HPLC 95.7%

LC-MS m/z: 521(M+1).

$^1$H NMR (300 MHz, DMSO-$d_6$) δ 8.31 (s, 1H, NH), 7.52 (d, J=1.5 Hz, 1H, Ar—H), 7.42-7.30 (m, 4H, Ar—H), 6.22 (s, 1H, Ar—H), 5.00 (d, J=5.1 Hz, 1H, —OH), 4.89 (t, J=5.5 Hz, 1H, OH), 4.74 (t, J=5.7 Hz, 1H, OH), 4.40 (dd, J1=3 Hz, J2=2.4 Hz, 1H, N—$CH_2$), 4.14-4.06 (m, 1H, N—$CH_2$), 3.90 (brs, 1H, CH), 3.62-3.57 (m, 2H, Isopropyl-$CH_2$), 3.45-3.39 (m, 2H, $CH_2$OH), 1.46 (q, J=3.6 Hz, 2H,Cyclopropyl-$CH_2$), 1.35 (s, 3H, $CH_3$), 1.32 (s, 3H, $CH_3$) 1.12 (q, J=3.6 Hz, 2H, Cyclopropyl-$CH_2$).

Example-27: Preparation of Tezacaftor of Formula I

Compound of Formula XIb (100 gms), methanol (600 mL) and water (200 mL) were added to round bottom flask and stirred at 25-35° C. for 5-10 mins. The temperature of the reaction mass was gradually raised to 57-63° C. and cooled to 37-43° C. Dil. Hydrochloric acid (50 mL HCl in 200 mL water) was added at 37-43° C. and maintained at the same temperature for 2-3 h. The solvent was distilled till 2 volumes remained in the flask under vacuum while maintaining temperature below 40° C. The resulting residue was dissolved in methylene chloride (800 mL) and water (200 mL) and pH was adjusted to 8.5-9.5° C. with slow addition of aqueous $K_2CO_3$ solution (60 g $K_2CO_3$ dissolved in 600 mL water).

The resulting organic layer was washed with aqueous $K_2CO_3$ solution (300 mL) followed by water (300 mL) and concentrated. Ethyl acetate (600 mL) and methanol (50 mL) were added to the resulting compound followed by 5% Pd/C (50% wet; 20 g) in ethyl acetate (100 mL). The reaction mass was maintained under hydrogen gas at 25-35° C. for 7-8 h, filtered. HPLC analysis revealed the content of Tetramethyl impurity of Formula F: about 0.1 to 0.5%; N-Ethyl impurity of Formula G: about 0.2% to 0.5% and Di-hydro impurity of Formula H: about 0.5 to 10%.

Washed the resulting reaction mass with ethyl acetate (200 mL) and distilled the filtrate up to ~5 volumes remain under vacuum while maintaining temperature below 55° C. Gradually n-heptane (600 mL) was added while maintaining temperature at 49-55° C. over a period of 30-90 min and stirred for 90-120 min. Gradually cool to 25-35° C. over a period of 1-2 h, stirred for 2-3 h, filtered, washed with heptane (100 mL) and dried at 25-35° C. for 1-2 h followed by at 57-63° C. Yield=60 gms. HPLC Purity: 99.5%; Tetramethyl impurity of Formula F: about 0.05%; N-Ethyl impurity of Formula G: about 0.06% and Di-hydro impurity of Formula H: about 0.10%.

Example-28: Preparation of Tezacaftor of Formula I

Compound of Formula XIb (50 gms) was charged in to an Autoclave. MeOH (500 mL), methanolic HCl (5 mL) and 5% Pd/C (~50% wet; 7.5 gms) were added to the Autoclave. The autoclave was pressurized with hydrogen gas (4-5 kg/$cm^2$) and the temperature was gradually raised to 50-55° C., maintained for 3 hrs under hydrogen atmosphere. The reaction mass was cooled to ambient temperature and the catalyst was filtered. The filtrate was concentrated under reduced pressure and the obtained residue (foamy solid) was purified by column chromatography eluted with 3-5% v/v MeOH in methylene chloride. The obtained solid material was crystallized from a mixture of isopropyl alcohol and heptane to afford Tezacaftor. Yield=18.5 gins.

Purity by HPLC 98.6%

Example-29: Preparation of Compound of Formula VII'b

Compound of Formula VIb (1.5 gms) was dissolved in methanol (15 mL) in a round bottom flask at 25° C. Raney-nickel (0.3 gms) was added to the resulting mass and maintained for 3 h under hydrogen gas atmosphere at ambient temperature. Filtered the catalyst and washed with methanol. The filtrate was concentrated to afford the title compound. Yield=1.2 gins.

LC/MS m/z: 428 (M+1).

$^1$H NMR (300 MHz, DMSO-$d_6$) δ 7.33-7.25 (m, 6H, Ar—H), 7.17 (d, J=12.6 Hz, 1H, Ar—H), 6.76 (d, J=9 Hz, 1H, Ar—H), 6.05 (s, 1H, Ar—H), 4.48 (s, 4H, $NH_2$, Ph-$CH_2$), 4.36-4.23 (m, 2H, N—$CH_2$), 4.02 (q, J=4.5 Hz, 1H, CH), 3.66-3.52 (m, 4H, BnO—$CH_2$, O—$CH_2$), 1.39 (d, J=2.4 Hz, 9H, 3×$CH_3$), 1.18 (s, 3H, $CH_3$).

Example-30: Preparation of Compound of Formula VIIIb

Compound of Formula VII'b (1 gm) was dissolved in dimethyl formamide (10 mL) in a round bottom flask at 25° C. Tetra-n-butylammonium fluoride (1M solution in 8 mL THF) was added to the resulting solution, stirred for 1 h at 80° C. and then cooled to ambient temperature. Water (10 mL) was added to the reaction mass, stirred for 10 min and extracted with methyl tert-butyl ether. The organic extracts was washed with 10% sodium chloride solution and concentrated under reduced pressure at below 50° C. to afford the title compound as dark colored oil. Yield: 0.8 gins.

Example-31: Preparation of Compound of Formula XIIb

Compound of Formula IVb (25 gms) and acetonitrile (125 mL) were added in to a round bottom flask at 25° C. Bis(acetonitrile)dichloropalladium (II) (1.85 gms) was added to the reaction mass and the temperature of the mixture was raised to mild reflux at 80-82° C. and maintained for 3 hrs. The reaction mass was cooled to room temperature and the undissolved material was filtered. The filtrate was concentrated under reduced pressure. Methyl tert-butyl ether (125 mL) was added to the resulting residue, washed with 5% aq EDTA solution (75 mL) and the layers were separated. The organic layer was partially concentrated and temperature was adjusted to 45-50° C. N-hexane was added to the resulting reaction mass, stirred for 1 h at 45-50° C., cooled to 16-20° C. and aged for additional 3 h. The precipitated material was filtered and the obtained wet compound was dried under vacuum at 40-45° C. to afford title compound. Yield=20 gins.

Purity by HPLC 97.0%;

LC-MS m/z: 343.3 (M+1).

$^1$H NMR (300 MHz, DMSO-$d_6$) δ 11.64 (s, 1H, NH), 8.35 (d, J=7.5 Hz, 1H, Ar—H), 7.33-7.21 (m, 6H, Ar—H), 6.44 (d, J=1.5 Hz, 1H, Ar—H), 4.48 (s, 2H, Ph-$CH_2$), 3.52 (s, 2H, BnO—$CH_2$), 1.35 (s, 6H, $CH_3$).

Example-32: Preparation of Compound of Formula XIIb

The procedure described in example 24 was repeated by using mixture of IPA-water as isolation solvent instead cyclohexane to yield 23 gms of the title compound.

Example-33: Preparation of Compound of Formula XIIb

Compound of Formula IVb (5 gms) and dimethyl formamide (100 mL) were added in to a round bottom flask at 25° C. Tetra-butyl ammonium fluoride (1M solution in 42 mL of THF) was added to the reaction mass and the temperature of the mixture was raised to 70-73° C. and maintained for 3 hrs. The reaction mass was cooled to room temperature, quenched into chilled water and extracted with methyl tert-butyl ether. The organic extracts was washed with 10% sodium chloride and concentrated under vacuum to afford the title compound. Yield=4.7 gms.

Example-34: Preparation of Compound of Formula VIIb

Compound of Formula XIIb (2 gms), cesium carbonate (7.6 gms) and (S)-1-O-tosyl-2,3-O-isopropylideneglycerol (2 gms) in DMF (23 mL) were added in to a round bottom flask at 25° C. The temperature of the reaction mass was raised to 88-90° C. and maintained for 24 hrs. Second lot of cesium carbonate (3.8 gms) and (S)-1-O-tosyl-2,3-O-isopropylideneglycerol (2 gms) were added and the reaction mass was aged for additional 24 h. The mixture was cooled to ambient temperature and then partitioned between water (30 mL) and EtOAc (20 mL) and the layers were separated. The aqueous layer was extracted with ethyl acetate (10 mL) and combined the organic layers. The organic phase was concentrated under reduced pressure and the residue obtained was purified on flash chromatography to afford title compound. Yield=1.5 gms.

Example-35: Preparation of Compound of Formula VIIb

The procedure described in example 28 was repeated by using DMSO solvent instead DMF to yield 1 gm of the title compound.

Example-36: Preparation of Compound of Formula XIIIa

Compound of Formula IIa (5 gms) and trifluoroacetic acid (6.5 mL) were added in to a round bottom flask and allowed to cool to −12° C. to −16° C. (4S)-2,2-dimethyl-1,3-dioxolane-4-carbaldehyde of formula Va solution (4.15 gms in 35 mL of methylene chloride was added to the reaction mass, stirred for 15 min and sodium triacetoxyborohydride (6.8 gms) was added in 3 equal lots. The reaction mass was stirred for 1 hr at −12 to −16° C. and poured into 5% aq $NaHCO_3$ (50 mL). The layers were separated and the aqueous layer was with methylene chloride (20 mL). The combined organic layer was washed with 5% aq $NaHCO_3$ (25 mL) and water (25 mL) and concentrated to dryness. The residue obtained was purified by silica gel column chromatography using a gradient of 5-8% v/v ethyl acetate and n-hexane to afford title compound. Yield=4.2 gms.

LC-MS m/z: 349(M+1).

$^1$H NMR (300 MHz, $CDCl_3$) δ 8.29 (q, J=7.8 Hz, 1H, Ar—H), 6.38 (d, J=13.8 Hz, 1H, Ar—H), 5.53 (brs, 1H, NH), 4.49-4.42 (m, 1H, CH), 4.16 (dd, J1=6.6 Hz, J2=6.3 Hz, 1H, $NCH_2$), 3.82 (dd, J1=5.7 Hz, J2=5.7 Hz, 1H, $NCH_2$), 3.49-3.42 (m, 1H, O—$CH_2$), 3.36-3.25 (m, 1H, O—$CH_2$), 1.51 (s, 3H, $CH_3$), 1.40 (s, 3H, $CH_3$).

Example-37: Preparation of Compound of Formula XIIIa

Cesium carbonate (20.7 gms) was added to a compound of Formula IIa (5 gms) in dimethylformamide (15 mL) in a round bottom flask at 25° C. (S)-1-O-Tosyl-2,3-O-isopropylidene-glycerol of formula Vb (12.2 gms) was added to the reaction mass, stirred for 24 hrs at 87° C. to 93° C. TLC analysis revealed significant amount of unreacted starting material.

Example-38: Preparation of Compound of Formula VIb

Potassium carbonate (1.2 gms) in acetonitrile (20 mL), palladium acetate (6 mg), 1,4-bis(diphenylphosphino)butane (0.018 gms) and CuI (8 mg) were added in to a round bottom flask at 25° C. [(2,2-dimethylbut-3-yn-1-yl)oxymethyl]benzene of Formula IIIb (3.5 gms) and compound of Formula XIIIa (1 gm) were added to the reaction mass, stirred for 15 min at ambient temperature. The temperature of the reaction mass was raised to mild reflux at 80-82° C. and aged for 2 hrs. The mixture was cooled gradually to room temperature and filtered off the undissolved material under suction. The filtrate was concentrated under vacuum and the residue obtained was dissolved in ethyl acetate (15 mL), washed with 5% aq EDTA solution (10 mL) and evaporated to dryness. The resulting residue was purified by silica gel column chromatography using a gradient of 5-10% v/v ethyl acetate and n-hexane to afford title compound. Yield=0.8 gms.

Example 39: Characterization of Impurities of Formula A, Formula B, Formula C, Formula D, Formula E, Formula F, Formula G, Formula H and Formula I by $^1$H-NMR and Mass

| | |
|---|---|
| 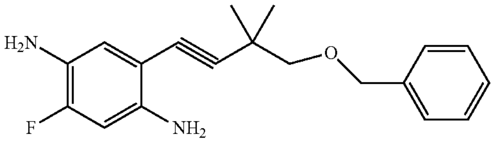<br>Diamino impurity of Formula A | 1H NMR (MHz, DMSO-d6)<br>δ = 7.37 (s, 4H), 7.35 (s, 5H), 6.64 (d, 1H,), 6.44 (d, 1H), 4.58 (s, 2H), 3.39 (s, 2H), 1.26 (s, 6H)<br>Mass: ES (+ve) m/z: 313.3 |
| 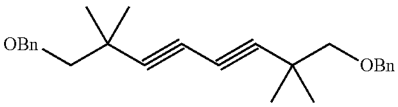<br>Dimethyl butyne dimer impurity of Formula B | 1H NMR (MHz, DMSO-d6)<br>δ = 7.38-7.25 (m, 10H), 4.53 (s, 4H), 3.31 (s, 4H), 1.18 (s, 12H)<br>Mass: m/z: 392.2 (M+$H_2O$) |
| 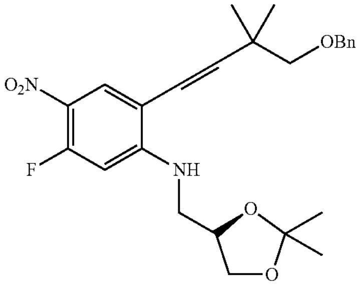<br>Ene impurity of Formula C | 1H NMR (MHz, DMSO-d6)<br>δ = 7.71 (d, 1H), 7.37-7.25 (m, 5H), 6.66 (d, 1H), 6.20 (t, 1H), 6.06 (d, 1H), 5.86 (d, 1H), 4.31 (s, 2H), 4.25 (p, 1H), 3.98 (t, 1H), 3.67 (t, 1H), 3.44-3.27 (m, 2H), 3.17 (s, 2H), 1.31 (s, 3H), 1.25 (s, 3H), 0.93 (s, 6H)<br>Mass: ES (−ve) m/z: 457 |
| 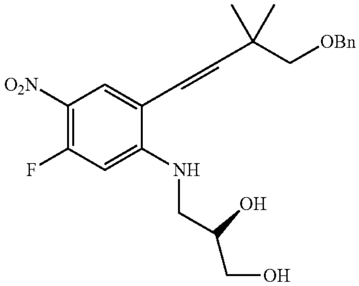<br>Dioxalane-Diol impurity of Formula D | 1H NMR (MHz, DMSO-d6)<br>δ = 7.91 (d, 1H), 7.39-7.27 (m, 5H), 6.70 (d, 1H), 6.44 (t, 1H), 5.14 (d, 1H), 4.83 (t, 1H), 4.60 (s, 2H), 3.72-3.65 (m, 1H), 3.49-3.32 (m, 5H), 3.26-3.17 (m, 1H), 1.30 (s, 6H)<br>Mass: ES (+ve) m/z: 417.2 |

-continued

| | |
|---|---|
| 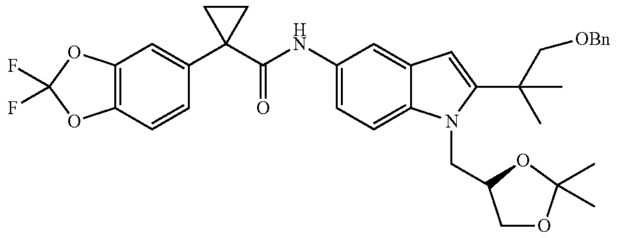 Des fluoro impurity of Formula E | Mass: ES (+ve) m/z: 633.4 |
| 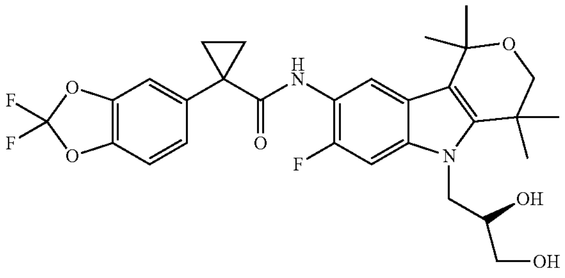 Tetramethyl impurity of Formula F | 1H NMR (MHz, DMSO-d6) δ = 8.30 (broad s, 1H), 7.53 (s, 1H), 7.42-7.31 (m, 4H), 5.00 (d, 1H), 4.93 (t, 1H), 4.36-4.31 (m, 1H), 4.00-3.92 (m, 1H), 3.85-3.80 (m, 1H), 3.54-3.36 (m, 4H), 1.51-1.48 (m, 2H), 1.48 (s, 6H), 1.34 (s, 3H), 1.31 (s, 3H), 1.15-1.11 (m, 2H) Mass: ES (+ve) m/z: 561.2 |
| 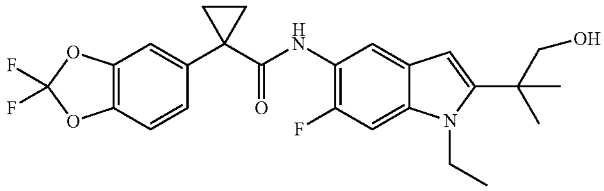 N-Ethyl impurity of Formula G | 1H NMR (MHz, DMSO-d6) δ = 8.30 (s, 1H), 7.52 (s, 1H), 7.52-7.39 (m, 2H), 7.34-7.25 (m, 1H), 7.23 (d, 1H), 6.18 (s, 1H), 4.82 (t, 1H), 4.30 (q, 2H), 3.58 (d, 2H), 1.49-1.44 (m, 2H), 1.33 (s, 6H), 1.25 (t, 3H), 1.15-1.11 (m, 2H) Mass: ES (+ve) m/z: 475.31 |
| 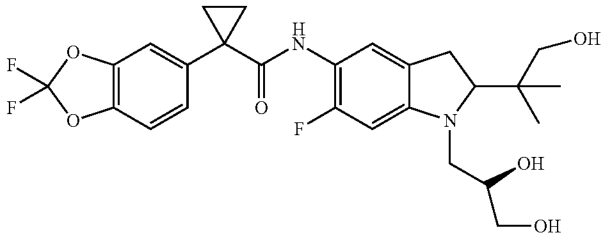 Di-hydro impurity of Formula H | Mass: ES (+ve) m/z: .523.14 |

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for preparation of tezacaftor of Formula I,

Formula I

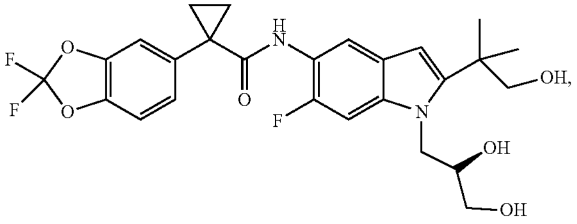

comprising:

a) reacting a compound of Formula II with an alkyne of Formula III to obtain a compound of Formula IV, Formula II

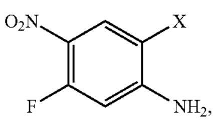

Formula III

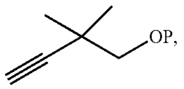

Formula IV

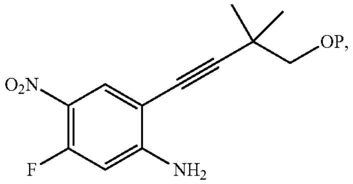

wherein “X” represents a suitable leaving group and “P” represents hydrogen or a suitable hydroxyl protecting group;

b) treating the compound of Formula IV with a compound of Formula V to obtain a compound of formula VI, Formula V

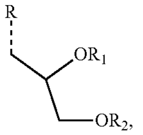

Formula VI

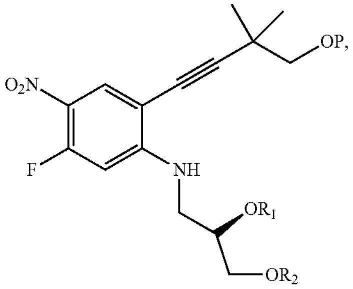

wherein “P” represents hydrogen or a suitable hydroxyl protecting group, “R” represents an oxygen atom or a suitable leaving group and dotted line represents a single bond or a double bond, and “R1” and “R2” may be same or different and represents a hydrogen or an alcoholic protecting group or “R1” and “R2” are taken together to form a diol protecting group;

c) cyclizing the compound of Formula VI to obtain a compound of Formula VII followed by reduction with a suitable reducing agent to obtain an amine compound of Formula VIII or a salt thereof; or, reducing the compound of Formula VI with a suitable reducing agent to obtain a compound of Formula VII' followed by cyclization to obtain an amine compound of Formula VIII or a salt thereof, Formula VII

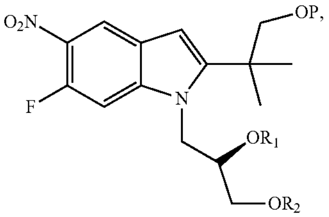

Formula VII'

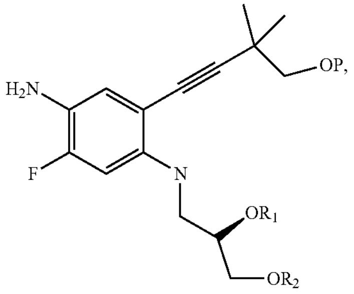

Formula VIII

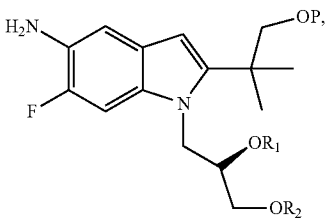

wherein “P”, “R1”, and “R2” are defined as above;

d) coupling the amine compound of formula VIII or a salt thereof with an acid compound of Formula IX or a reactive derivative thereof to obtain a compound of Formula X, Formula IX

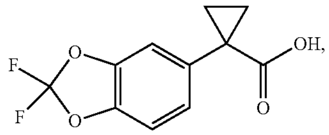

Formula X

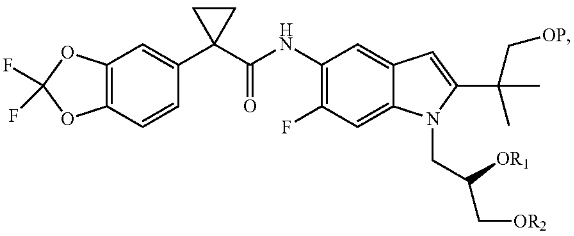

wherein “P” “R1” and “R2” are defined as above; and e) optionally deprotecting the compound of Formula X with a suitable deprotecting agent to obtain the tezacaftor of Formula I.

2. The process as claimed in claim 1, wherein the “X” represents a suitable leaving group selected from one of fluorine, chlorine, bromine, or iodine, wherein the “P” represents hydrogen or a suitable hydroxyl protecting group selected from the group consisting of alkyl, allyl, pivaloyl, acetyl, tosyl, mesyl, trimethylsilyl, tertiary butyldimethylsilyl, benzyl, para-methoxybenzyl, trityl, para-bromobenzoyl, para-nitrobenzoyl, benzoyl, triethylsilyl, triisopropylsilyl, benzyloxymethyl, p-methoxybenzyloxymethyl, [(3,4-dimethoxybenzyl)oxy]methyl, methoxymethyl, 2-methoxyethoxymethyl, methylthiomethyl, and 2-(trimethylsilyl) ethoxymethyl, wherein the "R" represents an oxygen atom or a suitable leaving group selected from the group consisting of fluorine, chlorine, bromine, iodine, methanesulfonyloxy, p-toluenesulfonyloxy, trifluoromethanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene) sulfonyloxy, (4-tertbutyl-benzene)sulfonyloxy, benzenesulfonyloxy, and (4-methoxy-benzene)sulfonyloxy, wherein the dotted line represents a single bond or a double bond, and wherein the "R1" and "R2" may be same or different and represents a hydrogen or an alcoholic protecting group selected from the group consisting of tetrahydropyranyl, benzyl, methyl, trimethylsilyl, triethylsilyl, triisopropylsilyl, tertiarybutyldipropyl silyl, t-butyldimethylsilyl, and t-butyldiphenyl group, or the "R1" and "R2" are taken together to form a diol protecting group selected from the group consisting of

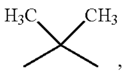
,
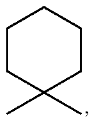
,
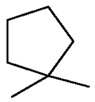
and
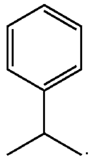

3. The process as claimed in claim 2, wherein the "X" represents bromine, wherein the "P" represents hydrogen or benzyl, wherein the "R" represents an oxygen atom when the dotted line represents a double bond, and methanesulfonyloxy or p-toluenesulfonyloxy when the dotted line represents single bond, and wherein the "R1" and "R2" taken together to form a diol protecting group of the formula

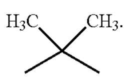

4. The process as claimed in claim 1, wherein the step a) reaction is carried out in the presence of a suitable catalyst, a suitable ligand, a suitable base, and a suitable solvent.

5. The process as claimed in claim 4, wherein the suitable catalyst is selected from one or more of the group consisting of bis(dibenzylideneacetone) palladium [Pd(dba)2], tris (dibenzylideneacetone) dipalladium [Pd2(dba)3], Palladium (II) chloride [$PdCl_2$], palladium (II) acetate [Pd(OAc)2], bis(triphenylphosphine) palladium (II) dichloride [$PdCl_2(PPh_3)_2$], [1,1'-bis(diphenylphosphino) ferrocene] dichloropalladium (II) [Pd(dppf)$Cl_2$], tetrakis (triphenylphosphine) palladium [Pd (PPh3)4], copper, cuprous bromide, cuprous iodide, 2,2'-bis-diphenylphosphanyl[1,1'] binaphtalenyl or allylpalladium(II) chloride dimer {[PdCl ($C_3H_5$)]$_2$}, and mixtures thereof, wherein the suitable ligand is selected from one or more of the group consisting of 1,2-bis(diphenylphosphino) ethane (dppe), 1,4-bis(diphenylphosphino)-butane (dppb), Triphenylphosphine ($PPh_3$), 4,5-bis(diphenylphosphino)-9,9-dimethylxanthene [xantphos], 2,2'-bis(diphenylphosphino)-1,1'-binaphthalene [BINAP], 1,1'-bis (diphenyl phosphine) ferrocene [DPPF], 2-(diphenyl phosphine phenyl) ether [DPEphos], tri-t-butyl phosphine [Fu's salt], 2-dicyclohexylphosphino-2'-(N,N-dimethylamino) biphenyl [DavePhos], 2-di-tert-butylphosphino-2'-(N,N-dimethylamino) biphenyl [t-BuDavePhos], trialkyl phosphines, and mixtures thereof, wherein the suitable base is selected from one or more of the group consisting of lithium hydroxide, sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, pyridine, and mixtures thereof, and wherein the suitable solvent is selected from one or more of the group consisting of acetonitrile, propionitrile, tetrahydrofuran, dimethyl ether, diisopropyl ether, methyl tertiary butyl ether, 1,4-dioxane, methylene chloride, ethylene chloride, chloroform, dimethylsulfoxide, diethyl sulfoxide, acetone, methyl isobutyl ketone, methyl ethyl ketone, dimethyl formamide, dimethyl acetamide, N-methyl pyrrolidinone, and mixtures thereof.

6. The process as claimed in claim 1, wherein the step b) reaction is carried out in the presence of an acid, a reducing agent, and a solvent.

7. The process as claimed in claim 6, wherein the acid is selected from one or more of the group consisting of formic acid, acetic acid, trichloroacetic acid, trifluoroacetic acid, 2,2,2-trifluoroethanol, tin chloride, thiourea, titanium isopropoxide, indium chloride, indium bromide, boric acid, p-toluenesulfonic acid monohydrate, benzoic acid, and mixtures thereof, wherein the reducing agent is selected from one or more of the group consisting of triethylsilane, tri-iso-propylsilane, polymethylhydrosiloxane, phenylsilane, diphenyl silane, triphenyl silane, sodium borohydride ($NaBH_4$), sodium cyanoborohydride, sodium triacetoxyborohydride, 2-picolineborane, α-picoline-borane, decaborane, boric acid, metal catalysts of nickel, copper, iron, cobalt, ruthenium, rhodium, palladium, osmium, iridium or platinum in the presence of hydrogen gas or hydrogen donor, and mixtures thereof, and wherein the solvent is selected from one or more of the group consisting of methanol, ethanol, isopropanol, toluene, xylene, chlorobenzene, heptane, hexane, dichloromethane, chloroform, ethylene dichloride, methyl acetate, ethyl acetate, n-propyl acetate, isopropyl acetate, tert-butyl acetate, dimethyl ether, diethyl ether, diisopropyl ether, tert-butyl methyl ether, tetrahydrofuran, dioxane, and mixtures thereof.

8. A process for the purification of a compound of Formula VI,

Formula VI

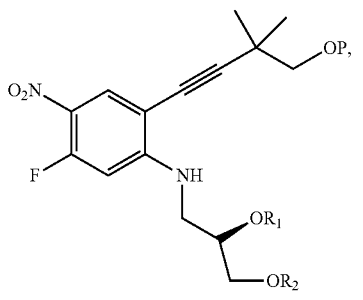

wherein the "P" represents hydrogen or a suitable hydroxyl protecting group, and "R1" and "R2" may be same or different and represents a hydrogen or an alcoholic protecting group or "R1" and "R2" are taken together to form a diol protecting group; comprising:

a) treating a compound of Formula VI with a suitable solvent, and b) isolating the purified compound of Formula VI.

9. The process as claimed in claim 8, wherein the "P" represents hydrogen or benzyl (Bn), and wherein the "R1" and "R2" taken together to form a diol protecting group of the formula

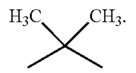

10. The process as claimed in claim 8, wherein the suitable solvent is selected from one or more of the group consisting of water, an alcohol selected from methanol, ethanol, isopropanol, n-propanol, n-butanol, and isobutanol, an aromatic hydrocarbon selected from toluene and xylene, an aliphatic or cyclic hydrocarbon selected from n-hexane, n-heptane, cyclohexane, and cycloheptane, and mixtures thereof.

11. The process as claimed in claim 8, wherein the compound of Formula VI obtained in step b) contains less than 0.5% as measured by HPLC of one or more of the impurities of a compound of Formula A, a compound of Formula B, a compound of Formula C, or a compound of Formula D, Formula A

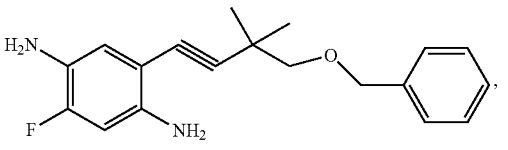

Formula B

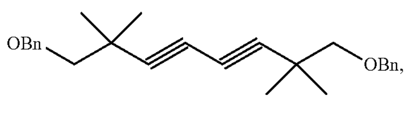

-continued

Formula C

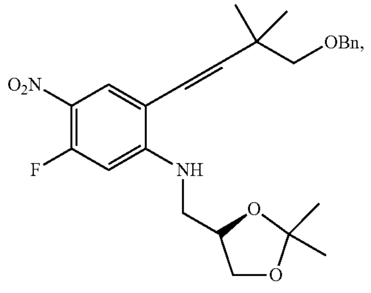

Formula D

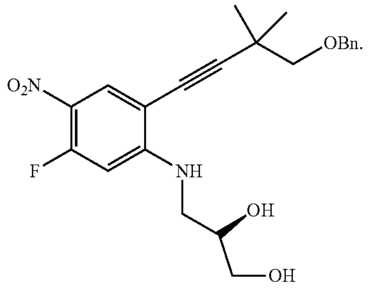

12. The process as claimed in claim 1, wherein the cyclization of the compound of Formula VI and the cyclization of the compound of Formula VII' are carried out in the presence of a suitable base, a suitable solvent, and a suitable catalyst.

13. The process as claimed in claim 12, wherein the suitable catalyst is selected from one or more of the group consisting of Tetra-n-butylammonium fluoride, bis(dibenzylideneacetone) palladium [Pd(dba)2], tris (dibenzylideneacetone) dipalladium [Pd2(dba)3], palladium (II) acetate [Pd(OAc)2], bis(triphenylphosphine) palladium (II) dichloride [PdCl2($PPh_3$)$_2$], [1,1'-bis(diphenylphosphino) ferrocene] dichloropalladium (II) [Pd (dppf)$Cl_2$], tetrakis (triphenylphosphine) palladium [Pd(PPh3)4], copper, cuprous bromide, cuprous iodide, 2,2'-bis-diphenylphosphanyl [1,1'] binaphtalenyl, allylpalladium (II) chloride dimer {[PdCl ($C_3H_5$)]$_2$}, disodium tetrachloropalladate [$Na_2PdCl_4$], palladium (II) chloride [$PdCl_2$], bis(acetonitrile)dichloropalladium (II) [$PdCl_2$(MeCN) 2], and mixtures thereof, wherein the suitable solvent is selected from one or more of the group consisting of tetrahydrofuran, 2-methyl tetrahydrofuran, dimethyl ether, methyl tertiary butyl ether, methanol, ethanol, isopropanol, toluene, xylene, dimethylformamide, dimethyl acetamide, N-methyl pyrrolidinone, dimethylsulfoxide, sulfolane, acetonitrile, propionitrile, and mixtures thereof, and wherein the suitable base is selected from one or more of the group consisting of triethylamine, potassium tertiary butoxide, sodium ethoxide, potassium carbonate, sodium carbonate, cesium carbonate, sodium acetate, potassium acetate, diisopropyl ethyl amine, and mixtures thereof.

14. The process as claimed in claim 1, wherein the reduction of the compound of Formula VI and the reduction of the compound of Formula VII are carried out in the presence of a suitable reducing agent and a suitable solvent.

15. The process as claimed in claim 14, wherein the suitable reducing agent is selected from the group consisting of sodium borohydride, lithium aluminium hydride, and a metal catalyst under hydrogen source, wherein the metal catalyst is selected from the group consisting of palladium on carbon, $PtO_2$, Raney Nickel, nickel (II) chloride, iridium, ruthenium, rhodium, iron, zinc, and mixtures thereof, and wherein the hydrogen source is selected from one or more of the group consisting of ammonium formate, hydrogen gas, acetic acid, formic acid, sodium formate, and mixtures thereof, wherein the suitable solvent is selected from one or more of the group consisting of an ether selected from one of tetrahydrofuran, 2-methyltetrahydrofuran, dimethyl ether, and methyl tertiary butyl ether an alcohol selected from one of methanol, ethanol and isopropanol an amide selected from one of dimethylformamide, dimethyl acetamide, and N-methyl pyrrolidinone a sulfoxide selected from one or more of dimethylsulfoxide and sulfolane, water, and mixtures thereof.

16. The process as claimed in claim 1, wherein the coupling reaction of step d) is carried out in the presence of a base and a suitable solvent.

17. The process as claimed in claim 16, wherein the base is selected from one or more of the group consisting of triethylamine, diisopropylethylamine, N-methylmorpholine, 4-dimethylaminopyridine, pyridine; 2,6-lutidine, 1,4-diazabicyclo [2.2.2] octane, trimethylamine, 1,8-Diazabicyclo [5.4.0] undec-7-ene (DBU), 2,6-Di-tert-butyl-4-methylpyridine, di-tert butyl pyridine, 4-dimethylaminopyridine, and mixtures thereof, and wherein the suitable solvent selected from one or more of the group consisting of dichloromethane, chloroform, ethylene dichloride, methyl acetate, ethyl acetate, n-propyl acetate, isopropyl acetate, tert-butyl acetate, toluene, xylene, chlorobenzene, heptane, hexane, methanol, ethanol, 1-propanol, 2-propanol, 1-butanol, 2-butanol, 1-pentanol, 1-octanol, cetonitrile; dimethyl formamide; dimethyl sulfoxide; dimethyl acetamide, water, and mixtures thereof.

18. The process as claimed in claim 1, wherein the deprotection of step e) is carried out in presence of a suitable deprotecting agent in a suitable solvent.

19. The process as claimed in claim 18, wherein the suitable deprotecting agent is selected from one or more of the group consisting of p-toluene sulphonic acid, hydrochloric acid, palladium on carbon in the presence of a hydrogen source selected from the group consisting of hydrogen gas, hydrochloric acid, ammonium formate, and mixtures thereof, and wherein the suitable solvent selected from one or more of the group consisting of ethylacetate, tetrahydrofuran, methanol, isopropanol, ethanol, water, and mixtures thereof.

20. The process as claimed in claim 1, further comprising:

f) forming a pharmaceutical composition comprising the tezacaftor obtained in step e) and at least one pharmaceutically acceptable excipient.

* * * * *